United States Patent
Bayley et al.

(10) Patent No.: US 11,624,047 B2
(45) Date of Patent: Apr. 11, 2023

(54) 3D PRINTING OF GEL NETWORKS

(71) Applicant: Oxford University Innovation Limited, Oxford (GB)

(72) Inventors: John Hagan Pryce Bayley, Oxford (GB); Shaohua Ma, Oxford (GB)

(73) Assignee: Oxford University Innovation Limited, Botley (GB)

( * ) Notice: Subject to any disclaimer, the term of this patent is extended or adjusted under 35 U.S.C. 154(b) by 693 days.

(21) Appl. No.: 16/305,655

(22) PCT Filed: Jun. 2, 2017

(86) PCT No.: PCT/GB2017/051598
§ 371 (c)(1),
(2) Date: Nov. 29, 2018

(87) PCT Pub. No.: WO2017/208020
PCT Pub. Date: Dec. 7, 2017

(65) Prior Publication Data
US 2020/0115665 A1    Apr. 16, 2020

(30) Foreign Application Priority Data
Jun. 3, 2016    (GB) .................................... 1609764

(51) Int. Cl.
*C12M 3/00*    (2006.01)
*B81C 99/00*    (2010.01)
(Continued)

(52) U.S. Cl.
CPC ......... *C12M 21/08* (2013.01); *B81C 99/0095* (2013.01); *C12M 25/14* (2013.01);
(Continued)

(58) Field of Classification Search
None
See application file for complete search history.

(56) References Cited

U.S. PATENT DOCUMENTS

2010/0060875 A1    3/2010    Kwon et al.
2016/0130543 A1    5/2016    Daniele et al.
(Continued)

FOREIGN PATENT DOCUMENTS

CN    103820880 A    5/2014
CN    104582747 A    4/2015
(Continued)

OTHER PUBLICATIONS

Yuet et al., Langmuir 26(6): 4281-4287 (2010).*
(Continued)

*Primary Examiner* — Erin M. Bowers
(74) *Attorney, Agent, or Firm* — Hamilton, Brook, Smith & Reynolds, P.C.

(57) ABSTRACT

The invention provides a process for producing a gel network, which gel network comprises a plurality of joined gel objects, which process comprises: forming a plurality of gel objects in one or more microfluidic channels; dispensing the gel objects from the one or more microfluidic channels into a region for producing the network; and contacting each gel object with at least one other gel object in said region to join each gel object to at least one other gel object at a region of contact between the gel objects. The invention also provides a network of joined gel objects, comprising a plurality of gel objects, wherein each gel object is joined to an adjacent gel object at a region of contact between the gel objects. Also provided are various possible uses of the gel network.

16 Claims, 39 Drawing Sheets

(51) Int. Cl.
    C12M 1/12      (2006.01)
    C12N 11/04     (2006.01)
    C12N 11/087    (2020.01)
    C12N 11/084    (2020.01)
(52) U.S. Cl.
    CPC ............ *C12N 11/04* (2013.01); *C12N 11/084* (2020.01); *C12N 11/087* (2020.01); *B81C 2900/02* (2013.01)

(56) References Cited

U.S. PATENT DOCUMENTS

| | | |
|---|---|---|
| 2019/0105279 A1 | 4/2019 | Lipke et al. |
| 2020/0199514 A1 | 6/2020 | Hauser et al. |
| 2021/0031434 A1 | 2/2021 | Martinez et al. |
| 2021/0403649 A1 | 12/2021 | Sheikhi et al. |

FOREIGN PATENT DOCUMENTS

| | | | |
|---|---|---|---|
| CN | 107930542 A | | 4/2018 |
| CN | 108327263 A | | 7/2018 |
| WO | WO 2005/103106 | * | 11/2005 |
| WO | 2014025312 A1 | | 2/2014 |
| WO | WO 2014/064459 | | 5/2014 |
| WO | WO 2014/197999 | | 12/2014 |

OTHER PUBLICATIONS

Bhaskar, S., et al. "Multicompartmental Microcylinders", (2009), Angewandte Chemie 121, 4659-4663.
Chen, Y., et al., "Robust bioengineered 3D functional human intestinal epithelium" (2015), Sci Rep 5, 13708.
Cheng, Y., et al., "Anisotropic colloidal crystal particles from microfluidics", (2014), J. Colloid and Interface Science 421, 64-70.
DeMello, A., "Control and detection of chemical reactions in microfluidic systems", (2006) Nature 442, 394-402.
Dendukuri, D., et al., "Continuous-flow lithography for high-throughput microparticle synthesis", (2006), Nature Materials 5, 365-369,.
Dickinson, E., et al., "Time-Dependent Surface Pressures of Adsorbed Films of Caseinate + Gelatine at the Oil—Water Interface", Colloids Surfaces, 1985, 14, 135-141.
Donaldson, G.P., et al., "Gut biogeography of the bacterial microbiota", (2016) Nature Reviews Microbiology 14(1): 20-32.
Du, Y., et al., "Directed assembly of cell-laden microgels for fabrication of 3D tissue constructs", (2008) PNAS 105(28), 9522-9527.
Guarner, F., et al., "Gut flora in health and disease", (2003), The Lancet 361, 512-519.
Gustafsson, E.,et al "Role of Collagen Type II and Perlecan in Skeletal Development", (2003), Ann N Y Acad Sci. 995, 140-150.
International Preliminary Report for Patentability for International Application No. PCT/GB2017/051598, "3D Printing of Gel Networks", dated Dec. 4, 2018.
International Search Report for International Application No. PCT/GB2017/051598, "3D Printing of Gel Networks", dated Dec. 19, 2017.
Jin, B-J., et al., "Droplet marging in a straight microchannel using droplet size or viscosity difference", (2010), J, Micromech. Microeng. 20, 035003.
Kolesky, D.B., et al., "Three-dimensional bioprinting of thick vascularized tissues", (2016) PNAS, 113(12): 3179-3184.
Lee, K.J., et al., "Spontaneous shape reconfigurations in multicompartmental microcylinders", (2012) PNAS 109(40), 16057-16062.
Lindemans, C.A., et al., "Interleukin-22 promotes intestinal-stem-cell-mediated epithelial regeneration", (2015), Nature 528, 560-564.
Ma, Z., et al. "Self-organizing human cardiac microchambers mediated by geometric confinement", (2015), Nature Communications, 6, 7413.
MacRitchie, Chemistry at Interfaces, Academic Press, 2012, 1st ed, p. 16.
Moon, S., et al., "Layer by Layer Three Dimensional Tissue Epitaxy by Cell-Laden Hydrogel Droplets", (2010) Tissue Engineering Part C: Methods 16(1), 157-166.
Murphy and Atala, "3D bioprinting of tissues and organs", (2014) Nature Biotech 32, 773-785.
Nichol et al. "Cell-laden microengineered gelatin methacrylate hydrogels", (2010) Biomaterials 31(21): 5536-5544.
Nie, Z., et al. "Janus and Ternary Particles Generated by Microfluidic Synthesis: Design, Synthesis, and Self-Assembly", (2006) J. Am. Chem. Soc. 2006, 128(29) 9408-9412.
Peterson, L. W., et al. "Intestinal epithelial cells: regulators of barrier function and immune homeostasis", (2014), Nature Reviews Immunology 14, 141-153.
Pregibon, D.C., et al., "Multifunctional Encoded Particles for High-Throughput Biomolecule Analysis", (2007) Science, 315 1393-1396.
Sato, T., et al., "Single Lgr5 stem cells build crypt-villis structures in vitro without mesenchymal niche" (2009), Nature, 459, 262-266.
Schelero, N., et al., "Pickering emulsions stabilized by stacked catanionic micro-crystals controlled by charge regulation", (2011), Soft Matter. 7, 10694-10700.
Search Report for GB Application No. 1609764.4, "3D Printing of Gel Networks", dated Jan. 9, 2017.
Shyer, A.E., et al., "Villification: How the Gut Gets Its Villi", (2013), Science, 342(6155), 212-218.
Sierra-Martin, B., et al. "Bulk modulus of poly (N-isopropylacrylamide) microgels through the swelling transition", (2011) Phys. Rev. E 84(1), 011406.
Spence, J.R., "Directed differentiation of human pluripotent stem cells into intestinal tissue in vitro" et al (2011), Nature 470, 105-110.
Sung J.H., et al. "Microscale 3-D hydrogel scaffold for biomimetic gastrointestinal (GI) tract model", (2011) Lab chip, 11, 389-392.
Thiel, J., et al. "25th Anniversary Article: Designer Hydrogels for Cell Cultures: A Materials Selection Guide", (2014) Advanced Materials 26(1), 125-148.
Trivedi, V., et al. "A modular approach for the generation, storage, mixing, and detection of droplet libraries for high throughput screening", (2010) Lab Chip 10(18) 2433-2442.
Urbant, P., et al., "On the forced convective heat transport in a droplet-laden flow in microchannels", (2008), Microfluid Nanofluid 4, 533-542.
Walther, A., et al. "Janus Particles" Synthesis, Self-Assembly, Physical Properties, and Applications, (2013) Chem. Rev. 113 (7), 5194-5261.
Watson, C.L., "An in vivo model of human small intestine using pluripotent stem cells" et al (2014),Nat Med 20, 1310-1314.
Written Opinion for International Application No. PCT/GB2017/051598, "3D Printing of Gel Networks", dated Dec. 19, 2017.
Wu, Z.L., et al. "Three-dimensional shape transformations of hydrogel sheets induced by small-scal modulation of internal stresses", (2013) Nat. Comm. 4, 1586.
Xu, S., et al. "Generation of Monodisperse Particles by Using Microfluidics: Control over Size, Shape and Composition", (2005) Angew. Chem. Int. Ed., 44 724-728.
Yuet, K. P., et al., "Multifunctional Superparamagnetic Janus Particles", (2010) Langmuir 26(6), 4281-4287.
Yui, S., et al., "Functional engraftment of colon epithelium expanded in vitro from a single adult Lgr5+ stem cell" (2012), Nat Med 18, 618-623.
Ghorbanian, S., et al., "Microfluidic direct writer with interated declogging mechanism for fabricating cell-laden hydrogel constructs", Biomed Microdevices, (2014), 10 pages.
Zhe, L., "Microfluidic Fabrication of Bioinspired Hydrogel Microfibers", Dissertation submitted to Tsinghua University, Apr. 2018.

* cited by examiner

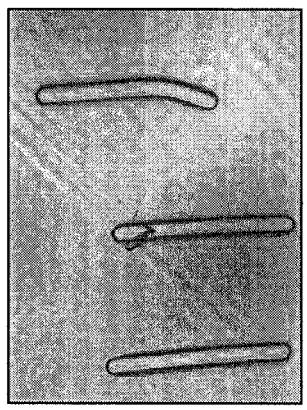
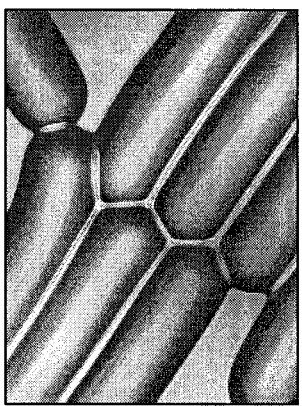
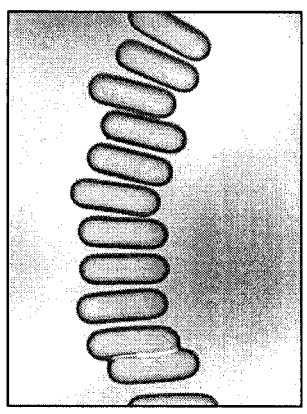
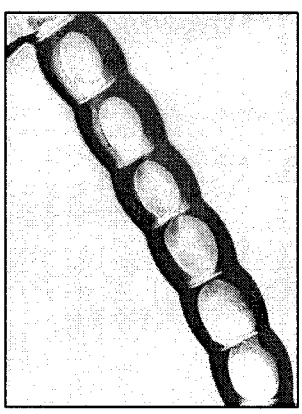
Fig. 1e
Fig. 1F
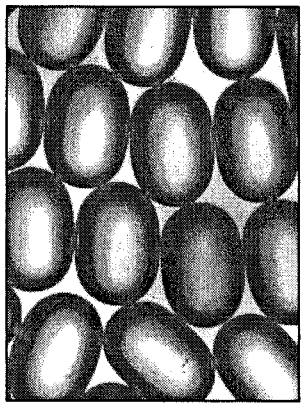
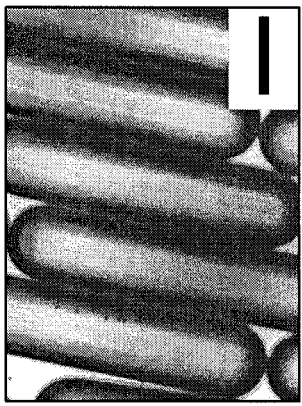
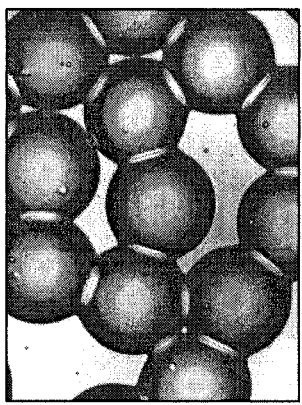
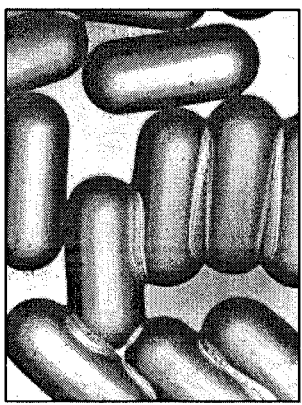
Fig. 1d

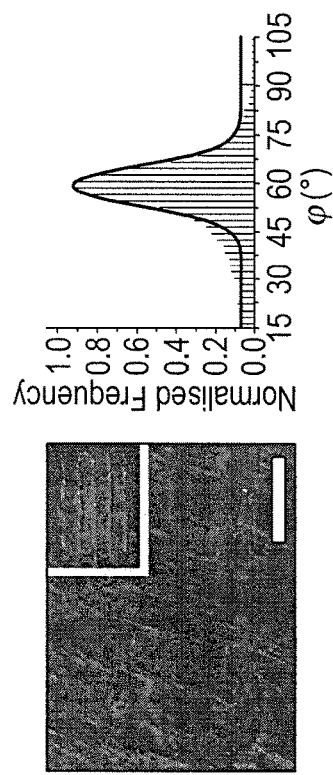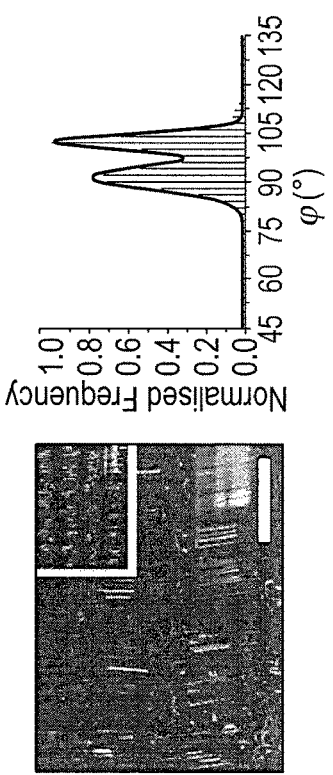
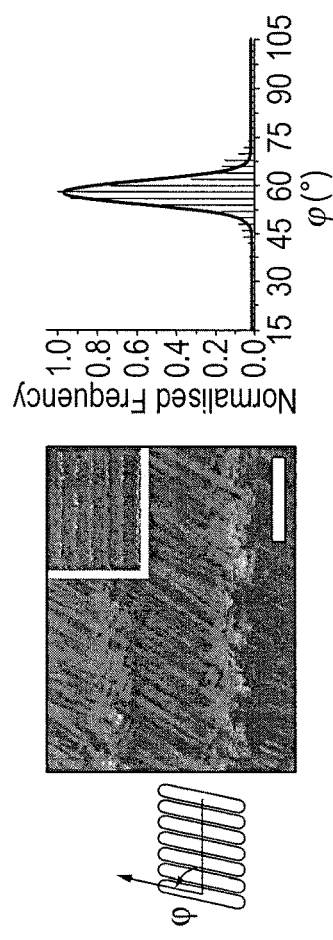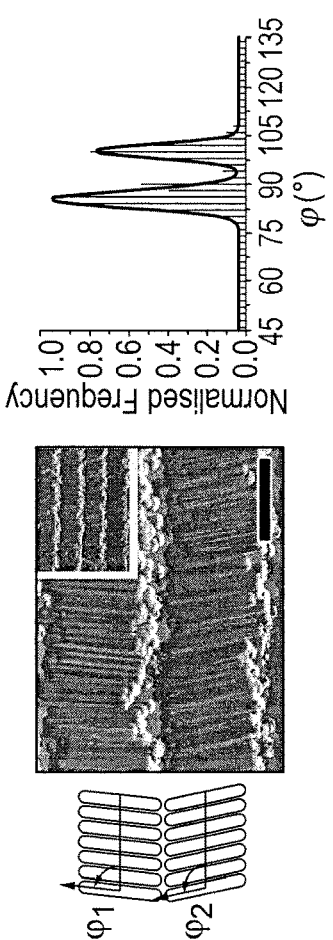

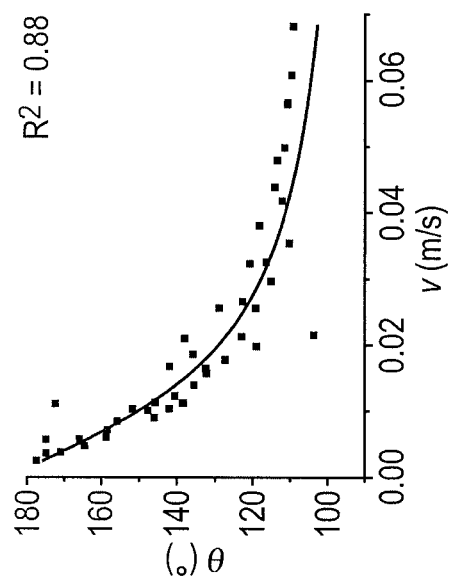
Fig. 3a
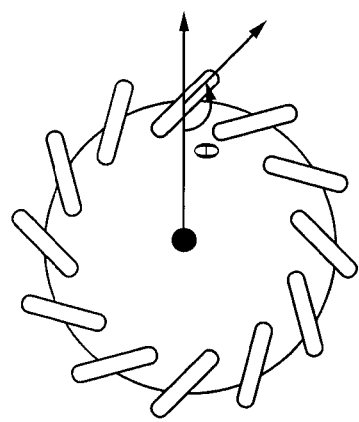
Fig. 3b
Fig. 3c
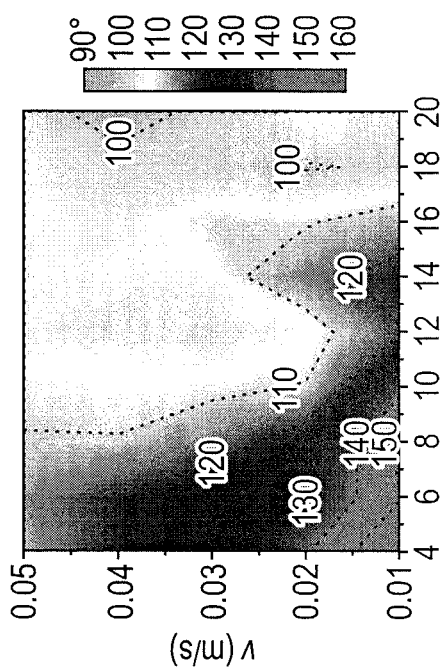
Fig. 3d
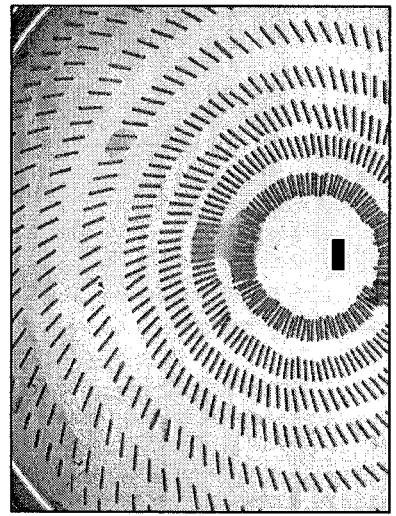
Fig. 3e

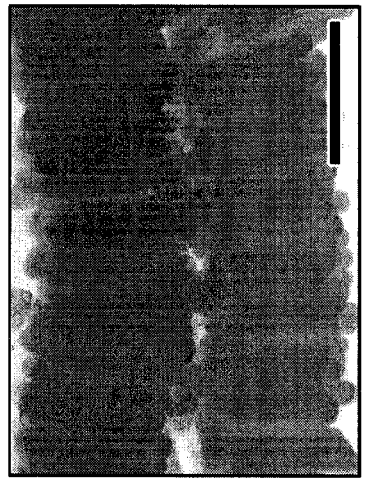
Fig. 4e
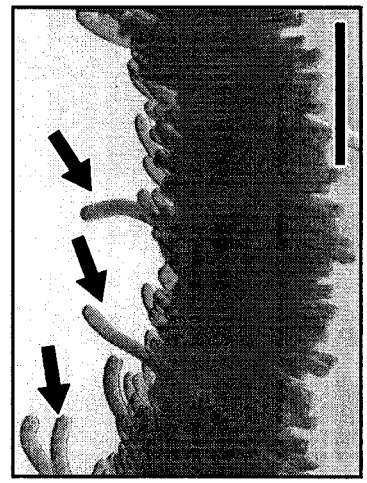
Fig. 4g
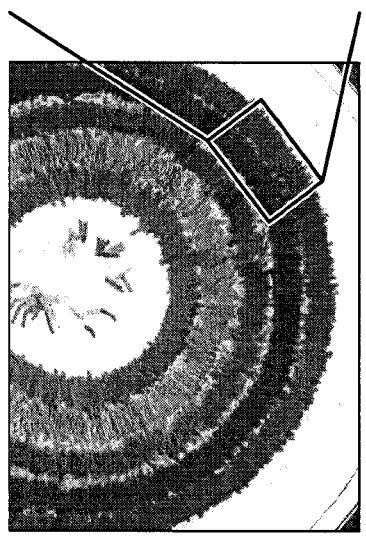
Fig. 4d
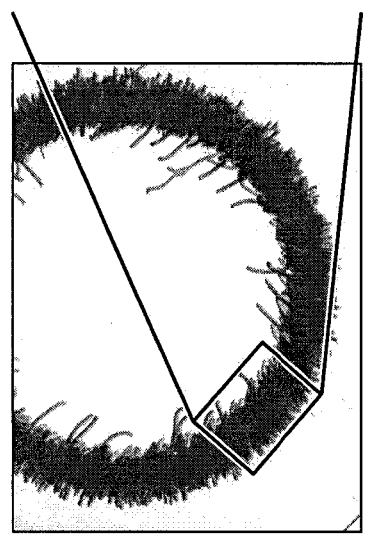
Fig. 4f
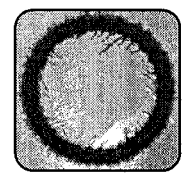

8°C

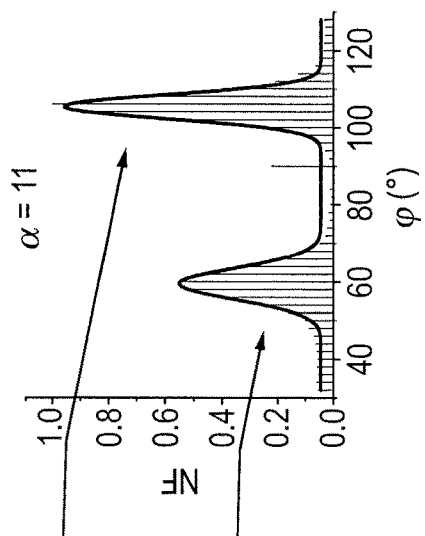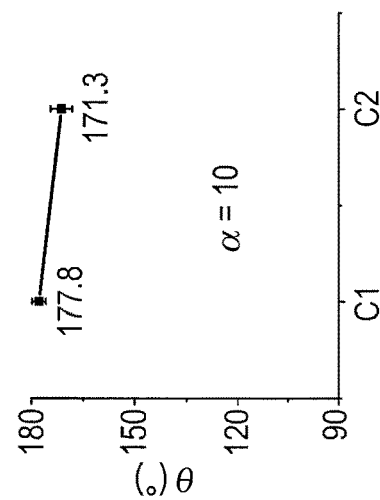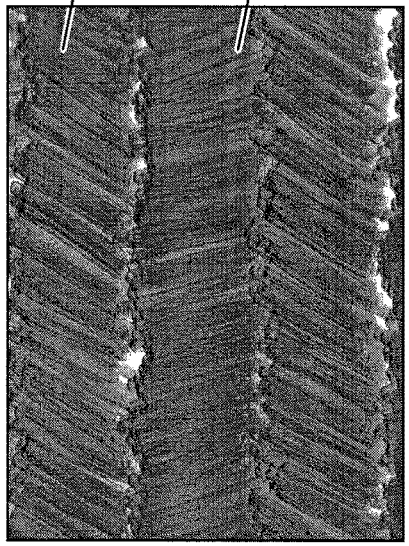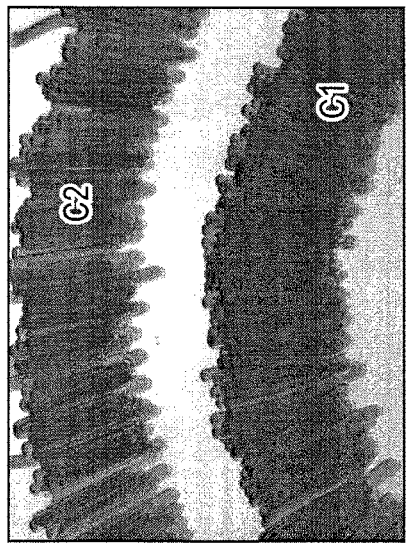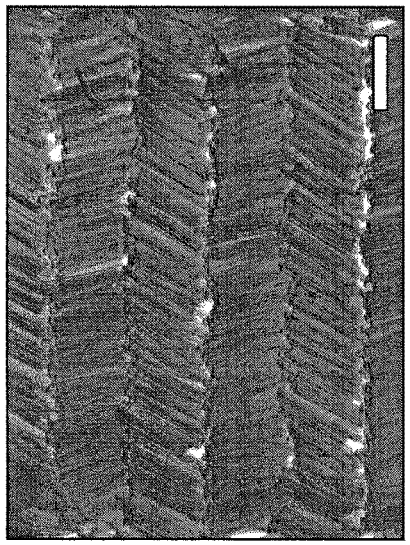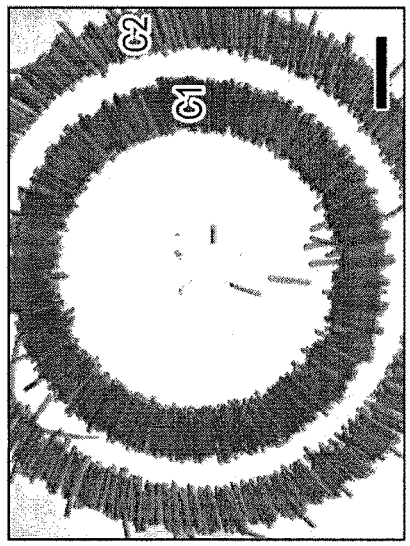

$\alpha = 7$
$\alpha = 5$

| | |
|---|---|
| Compression modulus (E', kPa) | 3.62 ± 0.04 |
| Loss modulus (E", kPa) | 0.88 ± 0.03 |
| E"/E' | 0.24 ± 0.01 |

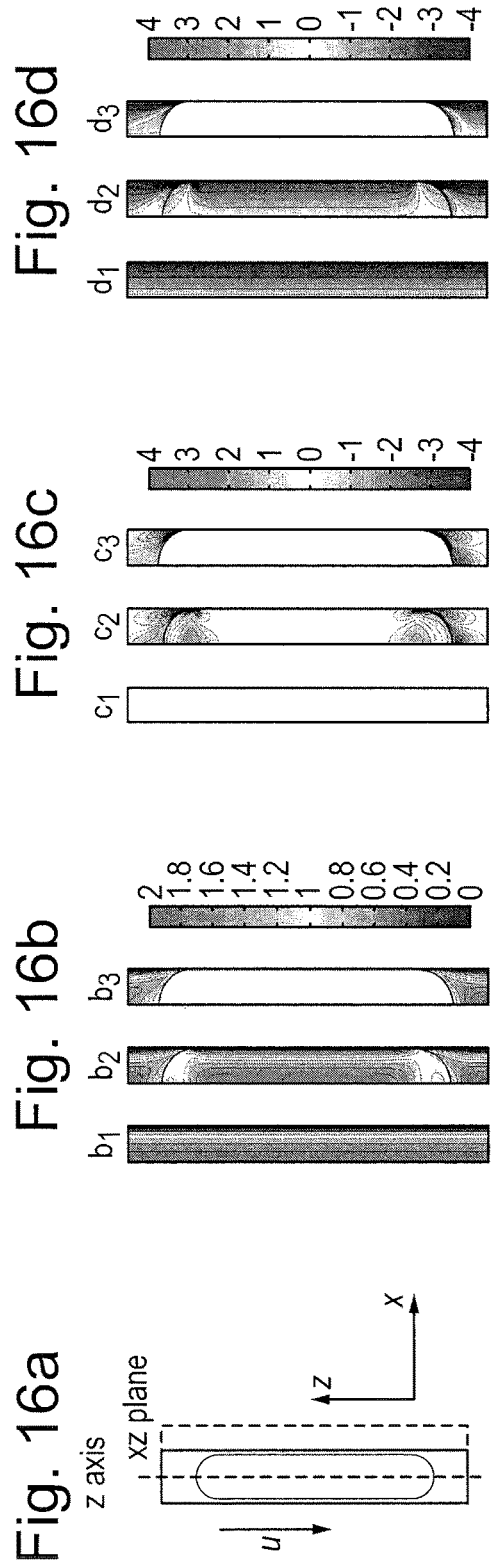
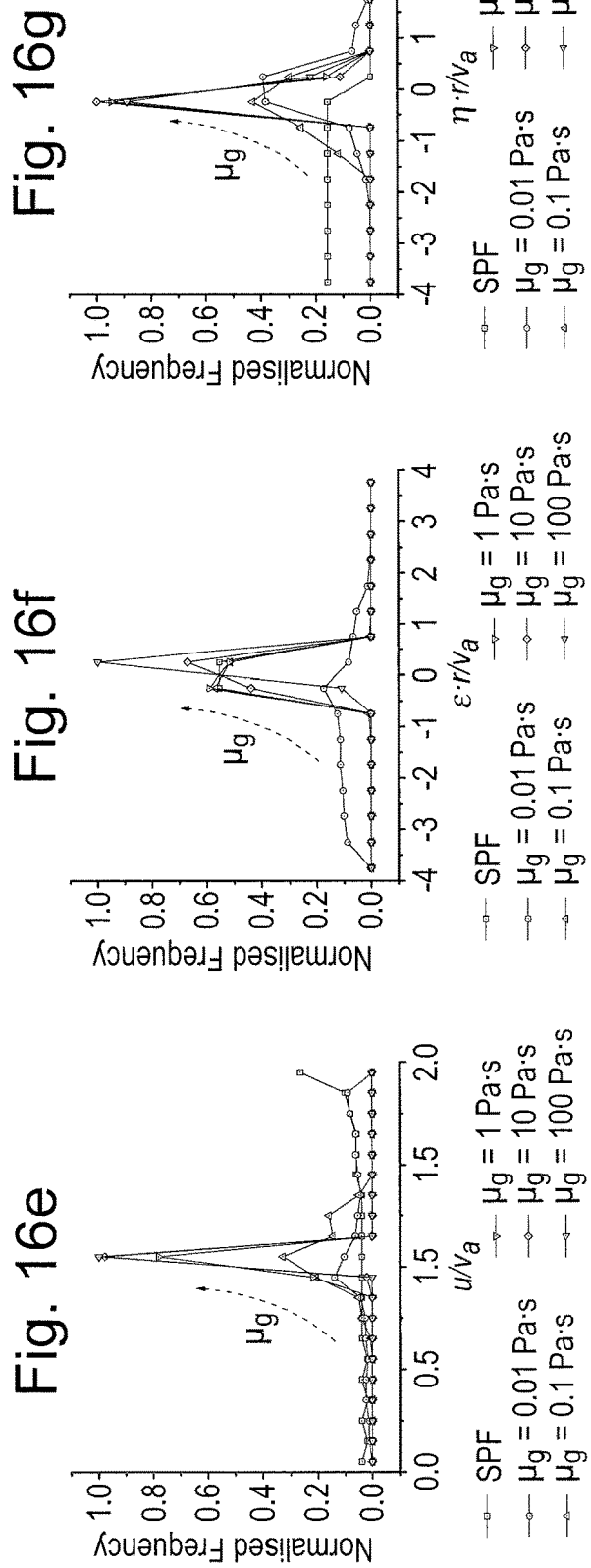

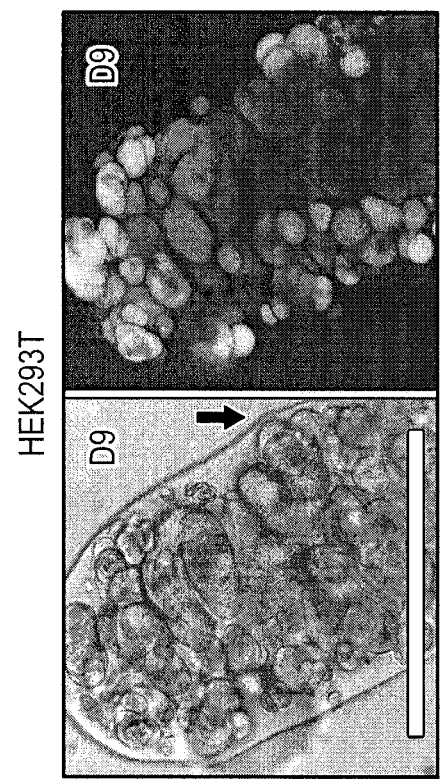
Fig. 19a HEK293T
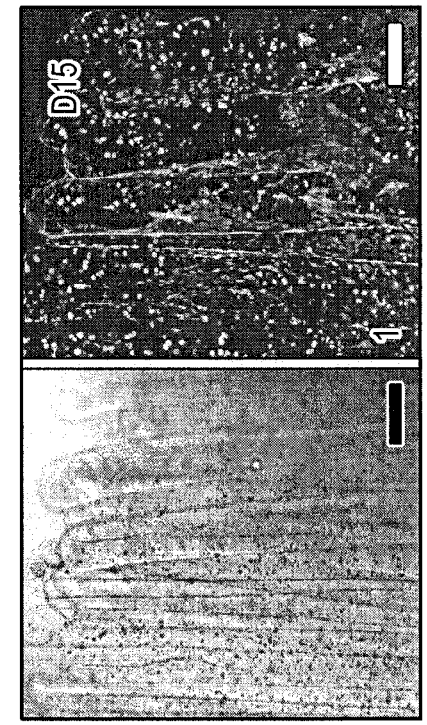
Fig. 19b HEK293T
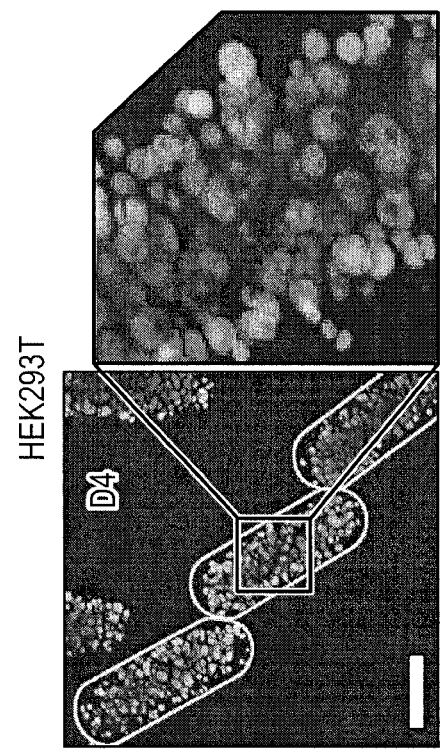
Fig. 19c NIH3T3/GFP
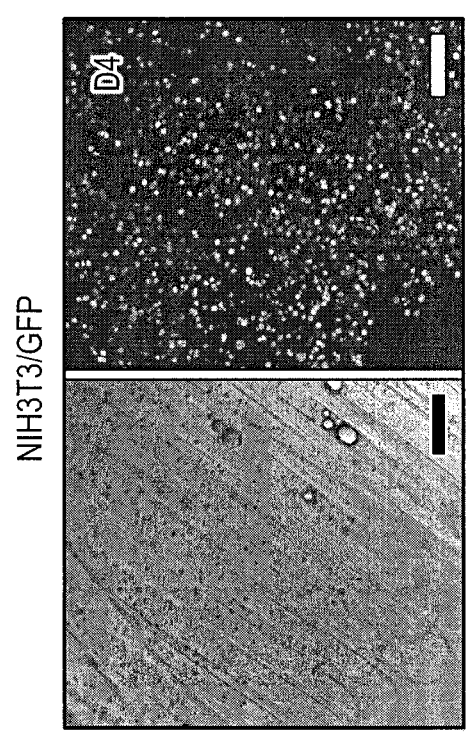
Fig. 19d NIH3T3/GFP

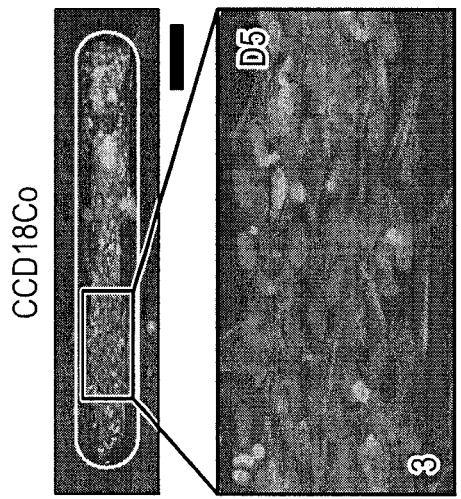
Fig. 19f
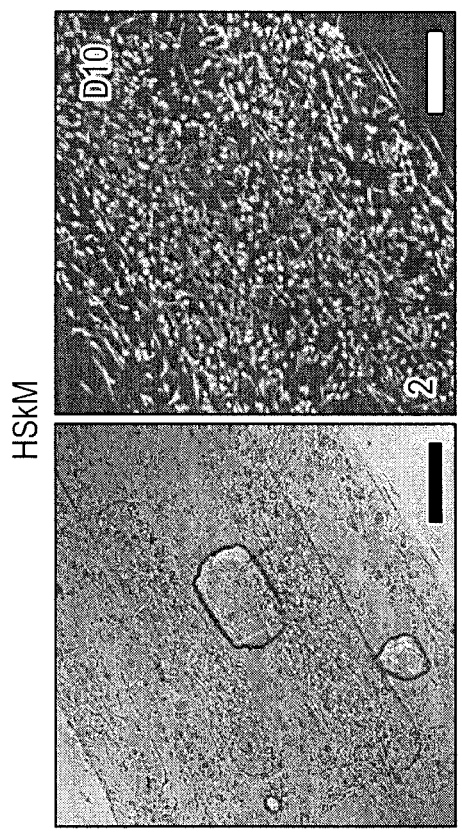
Fig. 19e
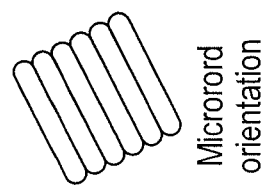
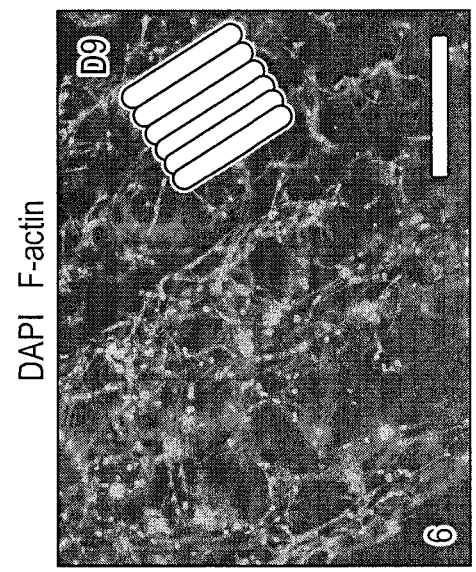
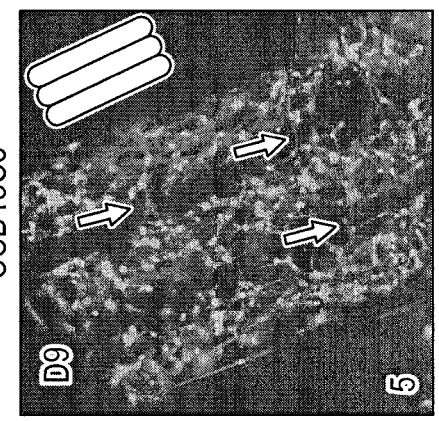
Fig. 19g
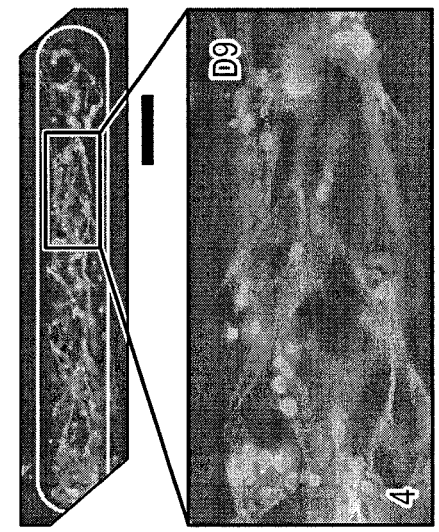

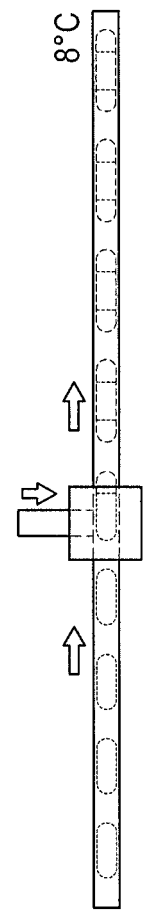
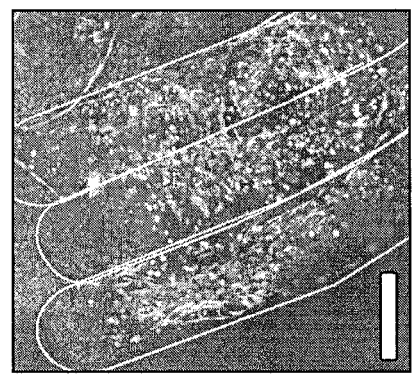
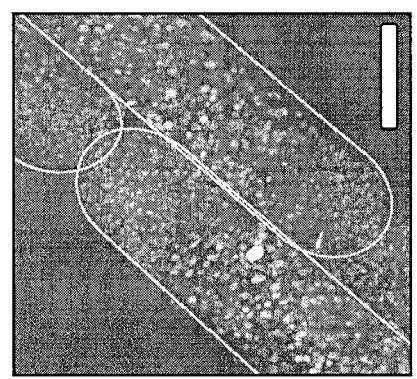
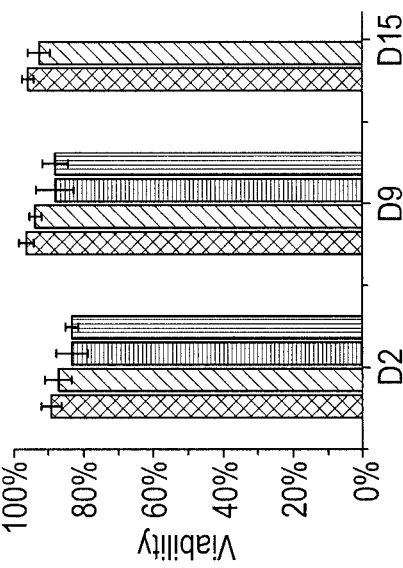
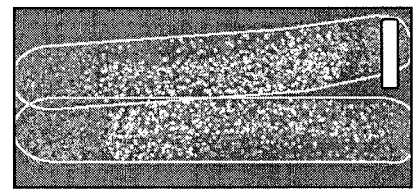

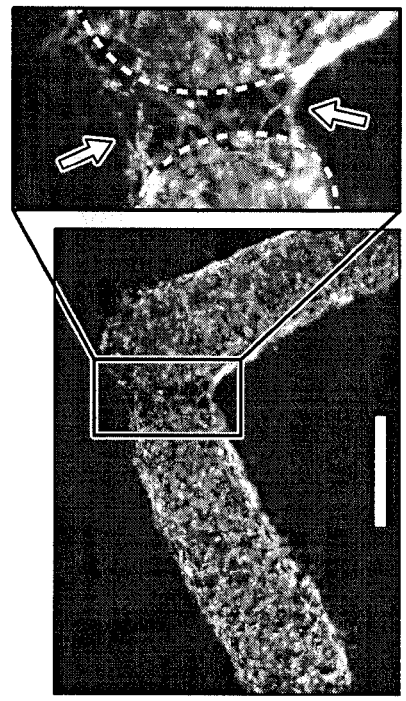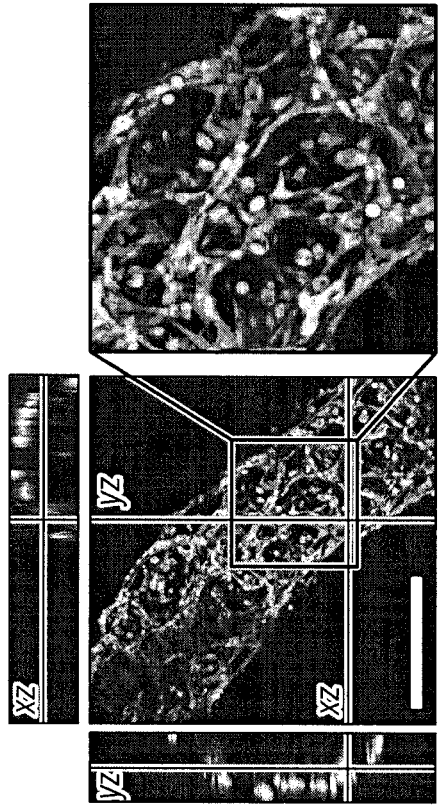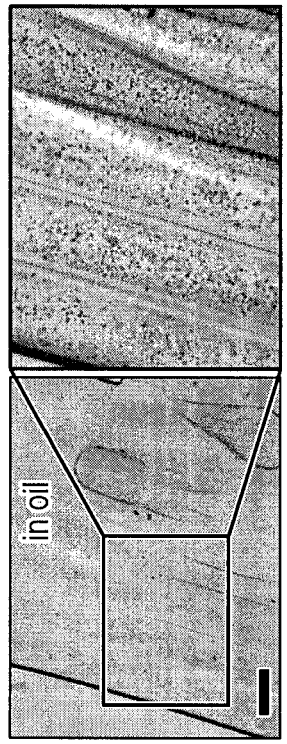

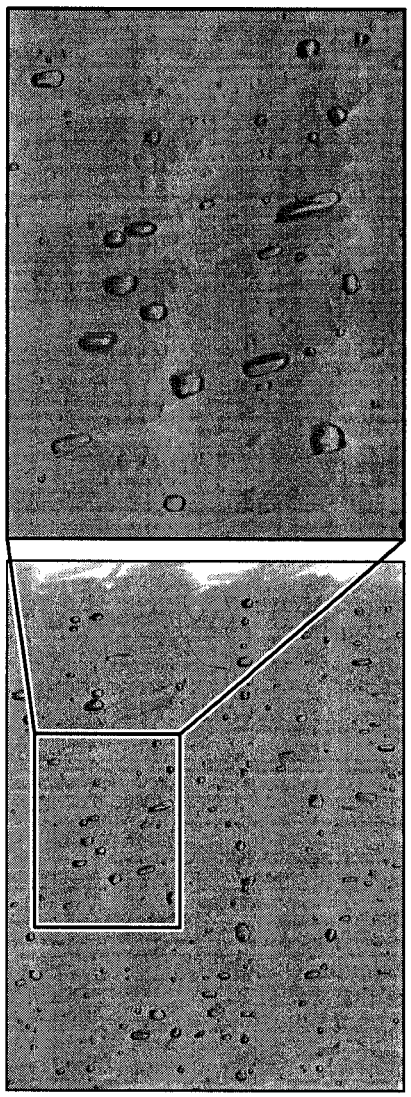
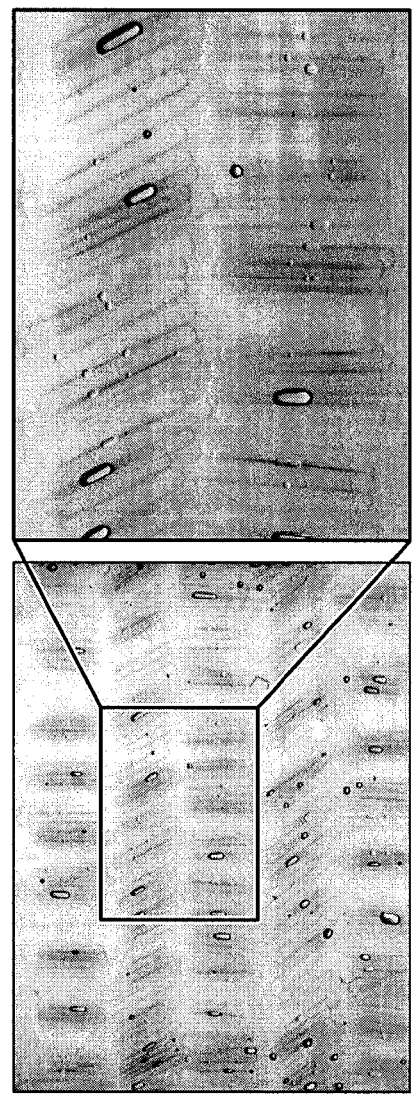
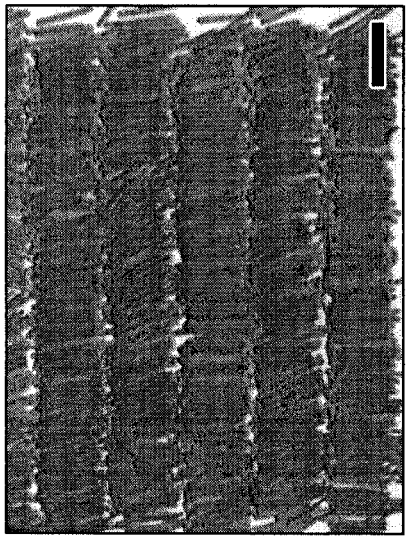
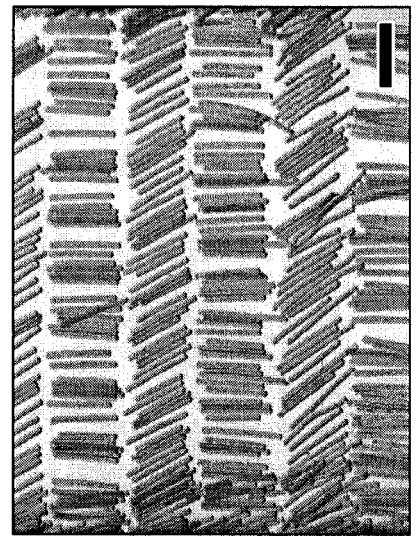

Fig. 24a
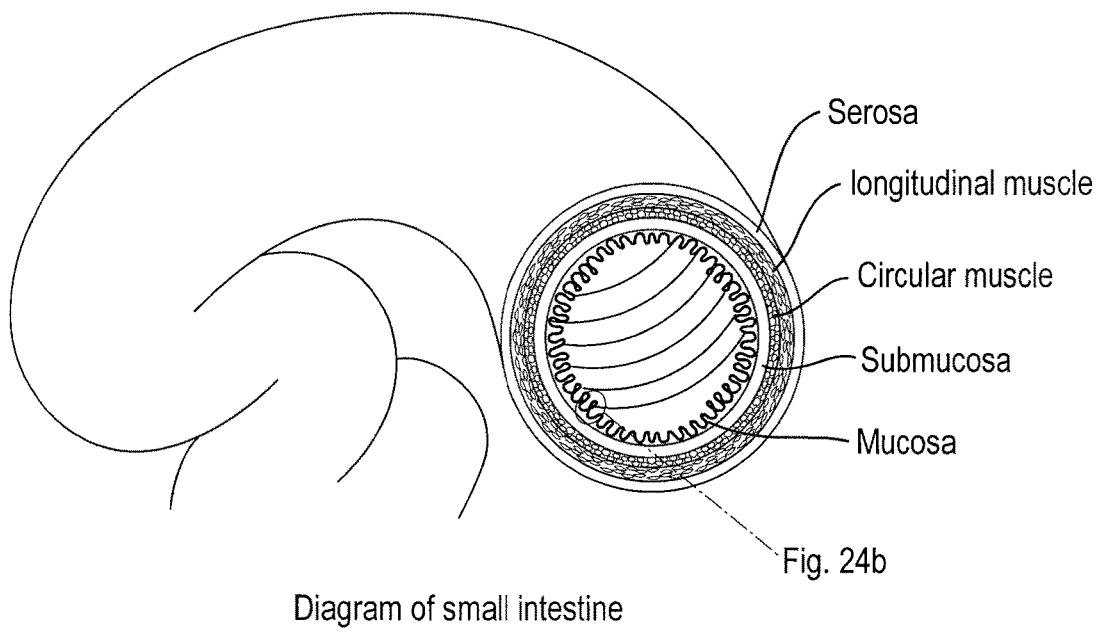
Diagram of small intestine
Fig. 24b
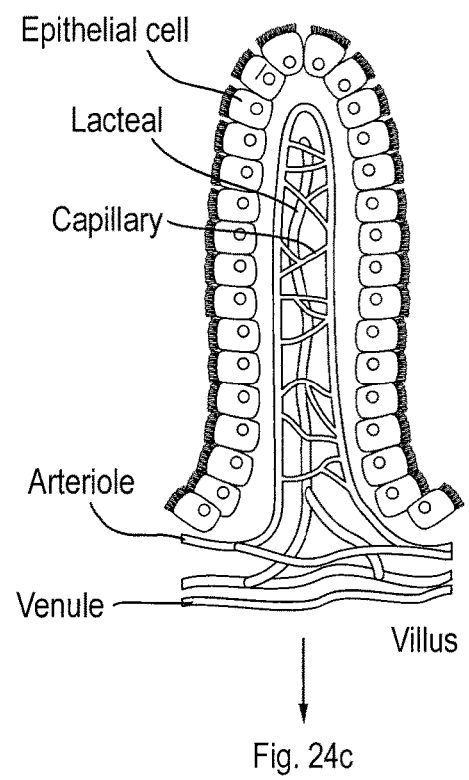
Fig. 24c

Fig. 24d ←

Microrod array

Lumen

3D PRINTING OF GEL NETWORKS

This application is the U.S. National Stage of International Application No. PCT/GB2017/051598, filed Jun. 2, 2017, which designates the U.S., published in English, and claims priority under 35 U.S.C. § 119 or 365(c) to GB Application No. 1609764.4, filed Jun. 3, 2016. The entire teachings of the above applications are incorporated herein by reference.

FIELD OF THE INVENTION

The invention relates to networks comprising a plurality of gel objects which are joined to one another. The objects in the network may be arranged in a two- or three-dimensional design. The invention also provides a microfluidic process suitable for producing a network according to the invention. Various possible uses of the network are described herein.

BACKGROUND TO THE INVENTION

It is thought that gel objects may provide useful building blocks in a diverse range of fields such as optical devices, novel materials and even in bio-engineering.

Various techniques for producing individual gel objects have been suggested. Gel objects have been produced by flow lithography (Dendukuri et al., Nature Materials, 5, 365-369 (2006)), by photopolymerising a gel flow to produce objects within a gel flow. This technique wastes a large amount of material and requires costly high-precision equipment. Furthermore, the size of the objects which may be produced is limited by the penetration depth of the laser used to photopolymerise the material. Another technique which has been used to create gel objects is cryosectioning (Bhaskar et al., Angewandte Chemie, 121, 4659-4663 (2009)). However, this technique is not compatible with the encapsulation of cells within the gel objects, or with the subsequent addition of biological cells. Cryosectioned gel objects must be functionalised before they can support living cells. Individual gel objects have also been produced by photopolymerisation of gel in a microfluidic channel to produce a hardened object (Cheng et al., J. Colloid and Interface Science, 421, 64-70 (2014)). Again, this technique requires UV light and is limited by light penetration and crosslinking efficiency. All these approaches lack spatial control of individual gel objects, and thus are not compatible with positioning such gel objects into networks. Moreover, these techniques produce gel objects with hardened surfaces which are challenging to form into gel networks.

Networks of gel objects are described in WO 2014/064459. This patent application describes the formation of individual hydrogel objects in an oil-based medium, which causes the objects to become coated in a bilayer of non-polymeric amphipathic molecules. The bilayer-coated objects may be squeezed together to form a network of adjacent objects.

The aforementioned techniques and networks leave room for improvement, particularly in the field of engineered small tissues. Engineered small tissues are promising in organ therapy and as in vitro tissue models to accelerate drug discovery at considerably reduced cost. Engineering suitable three-dimensional scaffolds as models of organs has been a major challenge, but a crucial one to meet due to the fact that scaffold geometry at the microscale steers cell behaviour (Ma et al., Nature Communications, 6, 1-10 (2015)). In order to provide a synthetic tissue or organ which accurately models the behaviour of living tissue, it is therefore vital to provide a 3D scaffold which mimics the hierarchical architecture of the living tissue. However, reconstitution of the intricate architectures of natural organs has been a major challenge for the in vitro fabrication of tissues. Most tissues comprise repeating units on the scale of tens to hundreds of microns. Important examples are tissues comprising oriented elongated (rodlike) repeating units, such as the gastrointestinal tract, muscle tissue, ligament and tendon, and there is a demand for in vitro engineered versions of these structures.

Directed assembly of cuboid cell-laden microgel fragments has produced ordered structures driven by the hydrophobic effect, DNA hybridization and molecular recognition. However, these approaches can only accommodate a few microgel fragments, and therefore scalability is an issue. Acoustic force can assemble large number of cuboids but lacks the control on orientation of elongated gel fragments. The patterning of hundreds to tens of thousands of elongated microgel shapes in programmed orientations remains challenging. The various existing 3D-printing techniques, including microextrusion printing, inkjet printing, laser-assisted printing and water-in-oil droplet printing, cannot order elongated microgel shapes as repeating units.

One example of an organ system with a complex functional structure is the gastrointestinal tract. The interior surface layer or epithelium is lined with villi, which increases the surface area and promotes absorption efficiency. The distinctive geometry of the epithelium plays a crucial role in the interactions of gut microbiota with the host in metabolic activities, immunity, and pathological disorders such as inflammatory bowel disease, as well as in host-bacteria mutualism (Guarner et al., The Lancet, 361, 512-519 (2003)). For instance, intestinal epithelial cells build physical barriers and segregate commensal bacteria (Artis et al., Nature Reviews Immunology, 13, 141-153 (2014)) and the geometry of the gut regulates the spatial distribution of bacterial microbiota (Donaldson et al., 14, 20-32 (2016)). Additionally, the development of the epithelium and migration of epithelial cells is steered by the geometry of the matrix on which they sit (Sung 24 al., 11, 3890392 (2011)).

There remains a need for a network of gel objects which is strong and flexible, and which is capable of supporting cells, and wherein the orientation of individual anisotropic elements is precisely controlled. Moreover there remains a need for a process for producing such an object in any medium, and which process is rapid and does not rely on expensive precision equipment.

SUMMARY OF THE INVENTION

The inventors have now provided a process for producing a network of gel objects, which network has a remarkable strength. The orientation of each gel object within the network may be precisely controlled, allowing the creation of a network with a complex three-dimensional architecture. Individual gel objects may be referred to herein as elements or elements of the network.

The process of the invention is a three-dimensional printing process. The process involves forming individual gel objects in microfluidic channels and then dispensing the gel objects at a precisely-chosen location. In some embodiments, the orientation of each gel object is also tailored. The gel objects are then brought into contact and joined at a region of contact between the gel objects. The gel objects are often incompletely gelled when they are brought into contact, to facilitate fusion of the objects together at the regions of contact, and further gelling within those fused regions, in order to form strong joins between the gel objects.

According to the invention, the fabrication of gel objects occurs in a microfluidic channel. Portions of gel and plugs of a medium which does not mix with the gel are alternated within the channel. At this stage the gel objects are usually incompletely gelled. The gel objects do not come into contact with one another in the channel and therefore the need for surfactant is removed. The dispensing of gel objects from a microfluidic channel is synchronised with the formation of a pattern. Therefore each gel object may be dispensed at a location which is pre-determined, for example by a computer programme, and which determines the location of the individual gel object within the network. The gel objects are typically incompletely gelled when they are dispensed. This allows further gelling to occur at a region of contact between two gel objects. The gel objects may be said to be fused at a point of contact. The further gelling at a region of contact between two gel objects creates strong adhesion between the adjacent objects. This may be described as the formation of a gel bond between the adjacent gel objects. As mentioned above this creates a strong adhesive bond and imparts great strength to the network as a whole. The strength of the bond between gel objects allows surprisingly large networks to be supported. It also fixes the position, and the orientation, of gel objects within the network.

The process is compatible with any gel. This feature of the process is advantageous in that it means that the process is very flexible. Additionally, the process may be used to produce a network comprising multiple kinds of gel object. As will be appreciated, the ability to build up a network of different objects allows the creation of complex objects. For instance, the process of the invention can build up a network having layers with differing properties in order to mimic the multilayered structure of human tissue or an optical device.

The process allows the network to be formed in any medium. The process may therefore reduce the number of steps in a process for forming a network in a medium. For instance, a network of gel objects comprising a hydrophilic gel may be produced directly in an aqueous medium according to the method of the invention. If such a network is intended to be used in an aqueous medium, the process of the invention therefore avoids the need to produce the network in a hydrophobic medium and then transfer it to a hydrophilic medium. The process of the invention can therefore be used to produce networks in-situ. This is a very particular advantage in biomedical applications where a network according to the invention can be produced in vivo during surgery.

Although the process itself is compatible with the formation of the network in any medium, it should be noted that not all gel objects are compatible with all media. Thus it may be desirable to print the network in one medium and transfer it to another medium. However, the network of the present invention is very strongly-bound and may therefore be easily transferred from, for example, an oil-based medium to an aqueous medium without damaging or breaking the network.

The size of the gel objects produced by the process of the invention is not particularly limited. Many of the methods of the prior art, by contrast, rely on photopolymerisation of gel in order to produce an object and are therefore limited to producing objects no larger than the penetration depth of the laser or other light sources (e.g. other UV light or, for instance, blue light sources). Similarly, the shape of the objects produced by the process of the invention is not particularly limited. The properties of the network of the invention may therefore be tuned using the size and shape of the gel objects which form part of the invention.

Additionally, the process can provide a network of gel objects wherein the composition of each gel object may be complex, for instance containing multiple regions of differing compositions. This has previously been possible by initiating polymerisation across the interface of a laminar flow. However, laminar flows can often cause clogging, and providing gel objects having multiple such regions using multiple laminar flows is difficult. The process of the invention is advantageous as it can conveniently produce gel objects having multiple differing regions of gel.

The process of the invention allows a large network to be rapidly built up; it is a high-throughput process. In some embodiments of the invention, the process of the invention is controlled by a computer programme and so can be automated to occur rapidly. Additionally, multiple gel objects can be formed simultaneously by employing multiple microfluidic channels, which allows the network to grow rapidly.

The process of the invention can create networks of gel objects having a wide variety of shapes and made from a wide range of materials. Moreover, the networks of the invention can be functionalised in order to be made suitable for a particular purpose. The flexibility of the process means that the networks of the invention can be designed to be suitable for a wide variety of purposes. For example, the networks of the invention may be used in bio-engineering, in optical devices, or as novel materials. For instance, the gel may be, and typically is, biocompatible such that the gel networks produced support biological cells and may be used as cell scaffolds.

Accordingly, the invention provides a process for producing a gel network, which gel network comprises a plurality of joined gel objects, which process comprises:
forming a plurality of gel objects in one or more microfluidic channels;
dispensing the gel objects from the one or more microfluidic channels into a region for producing the network; and
contacting each gel object with at least one other gel object in said region to join each gel object to at least one other gel object at a region of contact between the gel objects.

The inventors have also provided a network of gel objects, obtainable by the process of the invention. The network has remarkable strength and the orientation of each individual gel object may be precisely controlled. The network of gel objects may be obtained by the process of the invention.

In a further aspect, the invention provides a network of joined gel objects, which network comprises a plurality of gel objects, wherein each gel object is joined to an adjacent gel object at a region of contact between the gel objects.

The invention also provides the use of a network of joined gel objects according to the invention as a model of biological tissue; as an in vivo implant; in a method of drug delivery; in tissue bonding, for example in the repair of damaged tissue; in an optical device; or in an electronic device.

Figure 1A:
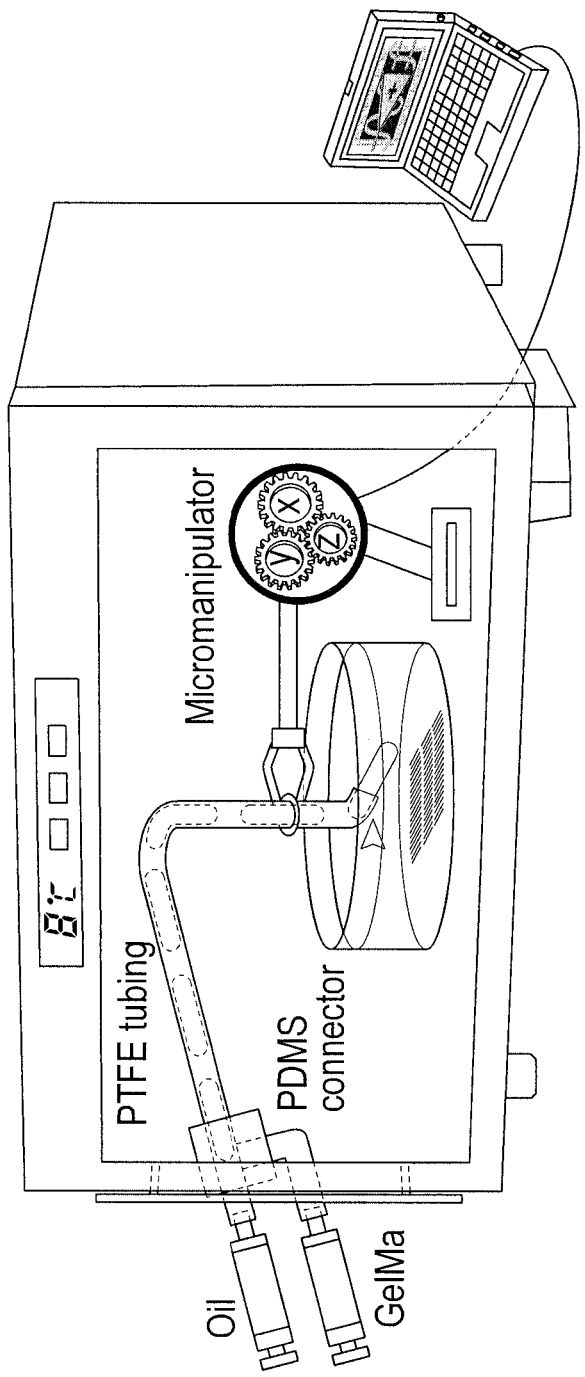
FIG. 1 illustrates the mechanism of 3D printing of gel microrods. Image (a) is an illustration of printing microrods using droplet-based microfluidic tubing (DMT). The tubing outlet, indicated by the arrowhead, is tilted to orient the microrods which are dispensed from the tube. It is tilted at a 30° to 45° angle with the substrate. (b) shows bright-field and zoomed-in images of gelatin-methacrylate (GelMa) droplets of varying sizes in microfluidics tubings (ID=200 μm). (c) shows the dependence of the droplet aspect ratio α on the volumetric flow rate ratio of oil to GelMa phases ($Q_o/Q_g$). (d) shows microspheres, ellipsoids and rods templated from GelMa droplets. (e) shows microrods formed in tubings with internal diameters of 100 μm and 50 μm, respectively. (f) shows fusion induced formation of a microsphere chain and a microrod network. Scale bar: 200 μm.

Images (a-d) show 3D arrays of parallel microrods wherein the rods are oriented at different angles ((a, b) α=10 (c, d) α=8) to the printing path (which corresponds approximately to the line formed by the rods' centres). The arrays shown in images (a, c) are in oil and arrays (b, d) are in water after phase-transfer. The network height, which in this case corresponds roughly to the length of the rods, is h=2.0 mm approximately.

Images (a'-d') show the normalised frequency of microrod direction φ in images (a-d) obtained by Fourier analysis. φ is defined as the angle between the longitudinal axis of each rod with the printing path. All networks were photocrosslinked after being transferred to water and maintained at 37° C. for 20 min and restored at room temperature.

Images (e, f) show the handling of microrod arrays using a tweezer. In (e) one end of the array (indicated by the arrow pointing upwards) is levelled up on a tubing (indicated by the arrow pointing downwards) in oil suspension. In (f) the array is rolled up in oil, picked up by a tweezer and resuspended in water.

Images (g-k) show shape transformations of gel sheets influenced by the directionality of microrods they contain. Diagram (g) illustrates a process for fabricating a thermoresponsive sheet and (h) shows a side-view and top-view of the thermoresponsive sheets of PNIPAM enclosing GelMa microrods arrayed at δ=45° (left) or 90° (right).

Images (i-k) show the reversible shape transformations of thermoresponsive sheets. (i) is an image series of the sheet (δ=45°) configuration (1) in hot water (45° C.), and (2) when transferred to cold water (20° C.), (3) reconfiguring and (4) reconfigured in hot water. The sheets adopted a helical/twisted configuration in hot water and relaxed in cold water. (j) Image series of the sheet (δ=90°) configuration (1) in hot water, and (2) when transferred to cold water and (3) when transferred back to hot water. The sheet arced along the longitudinal/transversal axis when configured in hot/cold water, but the transformation was insignificant. Image (k) shows a thermoresponsive sheet enclosing symmetrically arrayed microrods (δ=45°) in hot water; the shape reconfiguration was insignificant. Scale bar: 2 mm.

FIG. 3 illustrates that the process of the invention may be used to create circular microrod arrays while maintaining control over the directionality of the objects therein. Image (a) shows a 2D circular pattern of microrods (α=7), created in a petri dish full of oil by rotating the petri dish at constant angular velocity. Image (b) illustrates the definition of microrod direction represented by angle θ. (c) shows the dependence of the direction θ on the tangential velocity (also referred to as the hydrodynamic velocity) v: experimental data (dots) and the fitted equation (solid line curve). (d) is a contour map of dependence of the direction θ on the tangential velocity v and microrod aspect ratio α.

(e-f) are bright field images of a 3D circular pattern of microrods (α=12) in (e) oil and (f) in water after phase-transfer. h=3.0 mm.

Graph (g) demonstrates microrod direction θ of the first (h=0.1 mm) and top layer (h=3.0 mm) of the network. θ changed insignificantly (<5%) from the bottom layer to the top layer, and was identical in both oil and water.

Images (h-j) show a circular network in water after being scraped off the substrate: (h) leaning against the beaker wall; (i) deformed by a tip; (j) having regained the circular shape when free floating in water. All networks were photocrosslinked after being transferred to water and maintained at 37° C. for 20 min and restored at room temp. Scale bar: 2 mm.

Figure 4C:
Figure 4B:
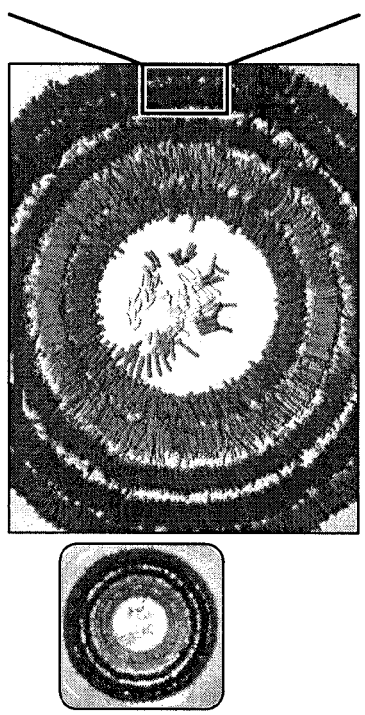
Figure 4A:
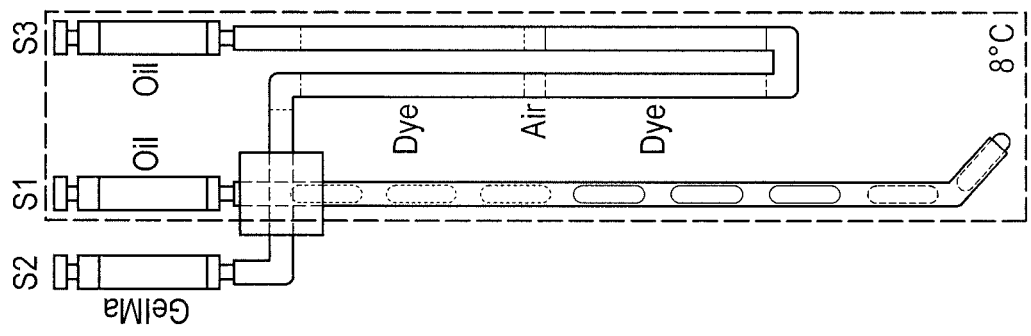

FIG. 4 illustrates the ability of the process to produce patterning of different microrod types. Image (a) is a diagram of a method by which different microrod types may be produced in a programmed pattern. Concentrated plugs of four different dyes (8 cm long) are partitioned in a conducting tubing (emerging from S3) by short air plugs (1 mm long). Syringe S3 is used to inject these dye plugs sequentially into the microfluidic channel in which the microrods are produced. Syringe S2 injects GelMa into the microfluidic channel, and the dyes mix with GelMa at a volume ratio of 1:10. This volume ratio is controlled by synchronically pumping the syringes S2 and S3, forming coloured plugs after being emulsified by oil from the syringe S1.

Images (b-e) show a concentric circular network (α=6) (b, c) in oil and (d, e) in water by sequentially patterning the inner to outer circles. Each ring is formed by an objects of a different colour.

Images (f, g) show a lamellar circular network (α=10) formed by sequentially patterning two different colours of microrods into one circle. Arrows in (c, g) indicate the occasional ill-shaped rods formed when the air plugs were injected into the tubing.

The network in images (d, e) was photocrosslinked after being transferred to water and incubated at 37° C. water for 20 min and restored at room temp. Scale bar: 2 mm.

FIG. 5 illustrates the process of fabricating and patterning Janus microrods.

Image (a) is a diagram of fabricating Janus microrods in DMT, by sequentially injecting two different colours (red and green) of GelMa into the emulsification tubing wetted by oil at the beginning and the half-way, respectively. Red gel is injected into the far end of the microfluidic tube, along with oil, forming red gel objects interspaced with oil plugs. Further down the tube, portions of green gel are injected. The time at which the green gel is injected is synchronised with the motion of the red gel objects down the microfluidic tube and controlled such that the green gel objects are injected directly adjacent to a red gel object to form a single gel object having two different-coloured regions.

Image (b) shows monodisperse red/green Janus microrods (α=5) in oil; image (b') contains RGB profile taken along the black line drawn along a rod in image (b). The upper line in (b') corresponds to the red profile; this is much higher at one end of the rod that the blue and green profiles. The green (middle line) and blue (lower line) profiles are low at one end of the rod and high at the other. This shows that the gel has not mixed; there is a "colour gradient" along the rod and it is therefore described as a Janus particle, having two different ends.

Image (c) shows circularly patterned red/blue Janus microrods (α=10) in oil. Graph (c') shows a RGB profile along the black line in the zoom-in image of a rod above graph (c').

The red profile, which is the upper profile at the left of the graph, is high at the left-hand end of the rod while the blue and green profiles have low intensity there. At the right-hand end of the rod, the red profile drops to zero and the blue and green profiles (which lie almost on top of one another) become more intense than the red profile.

Image (d) shows circularly patterned red/green Janus microrods ($\alpha$=14) in oil loaded with 0.2 wt % span 80 surfactant. Scale bar: 2 mm.

FIG. 6 illustrates the printing of a 3D structure resembling small intestine model.

Images (a-d) show a network of gel microrods in the form of a tube ($\alpha$=11) printed in a beaker in oil from (a) a top-view and (b) a side view, and suspended in water after being poured to a larger beaker from (c) a top-view and (d) a side-view. Images (e-g) show the shape transformation of the tube after being stored for 2 days in water at room temperature. (e) is a top top-view and (f) is a side-view of the tube out of water; (g) shows the tube resuspended in water.

Image (h) is a cross-sectional diagram of human small intestine. Regions from 1-4 represent the thick smooth muscle layer, the transition layer of muscle layer and epithelium, the intestinal villi and the intestinal lumen respectively.

Images (i-l) show a hybrid tube comprising the printed microrod tube (blue, $\alpha$=12) and the moulded GelMa periphery (red, the outer layer). Image (i) shows the whole tube; images (j, k) are zoomed-in of regions indicated by the arrows in (i). The zoom-in image shows four identical regions: (i) the red GelMa ring; (ii) the mixed region of blue microrods rooted in red GelMa; (iii) the circular array of microrods; and (iiii) the tube lumen. The height/length of the tubes was 2 cm, which was identical to the positioning range of the z axis of the micromanipulator. All networks were photocrosslinked after being transferred to water and incubated at 37° C. for 20 min and restored at room temperature. Image (1) is a top-view of the hybrid tube standing out of water after being stored for 2 days in water at room temp. Scale bar: 2 cm.

FIG. 7 illustrates the phase-transfer of a circular network from oil to water. Image (a) shows a tubular GelMa microrod network (coloured in blue in oil). Image (b) shows water (coloured red) inside the tube starting to penetrate the blue network and spill outwards, forming pools around the outside of the network. Images (c, d) show the blue network being (c) partially and (d) completely immersed in red water; image (e) the blue network having been removed from the red water being retaining the red colour as it is remains saturated with red water.

Figure 8A:
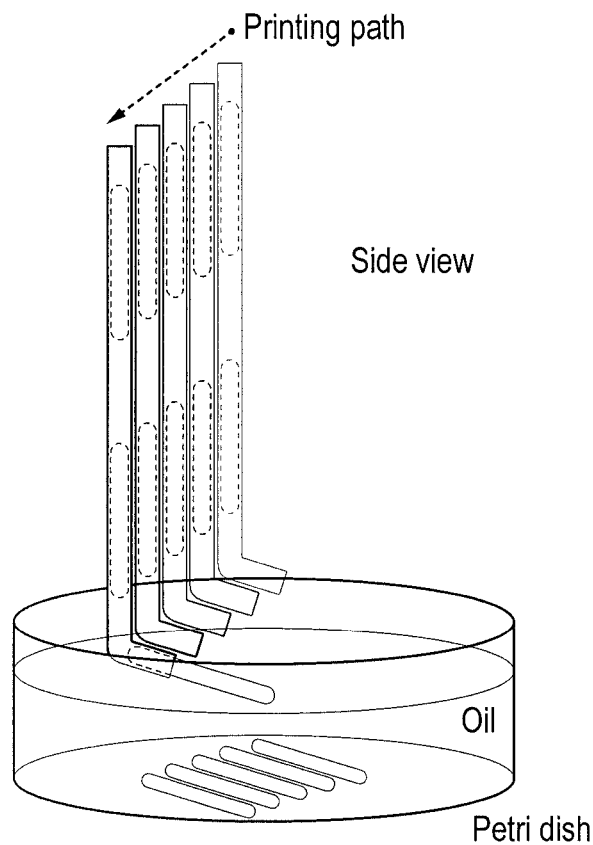
Figure 8B:
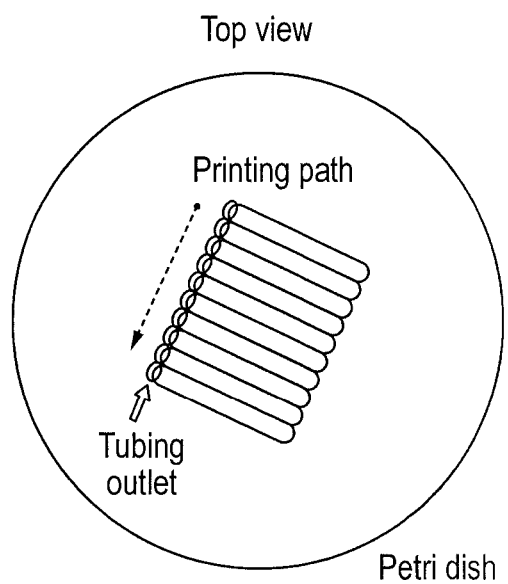
Figure 8C:
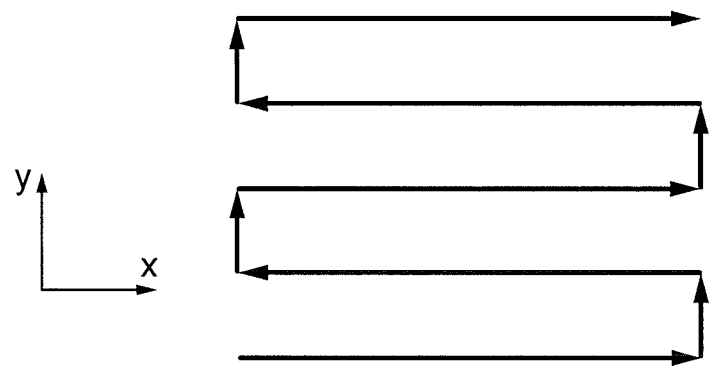

FIG. 8 contains diagrams showing how a network comprising a pattern of parallel microrods is produced. (a) is a side view of the network being printed and (b) is a top view, and (c) is the full layer printing path. The tilted tubing end (outlet) orients the microrods as they exit the tubing; parallel rods were arranged in rows along the printing path, and perpendicularly oriented to the printing path (diagram (b)).

Figure 9I:
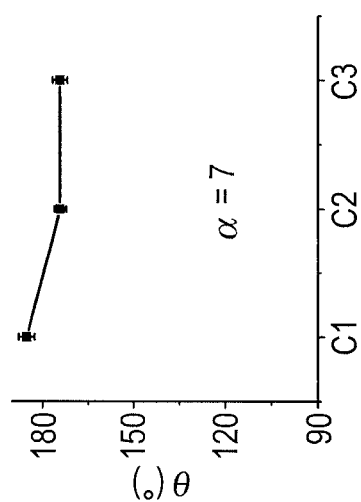
Figure 9H:
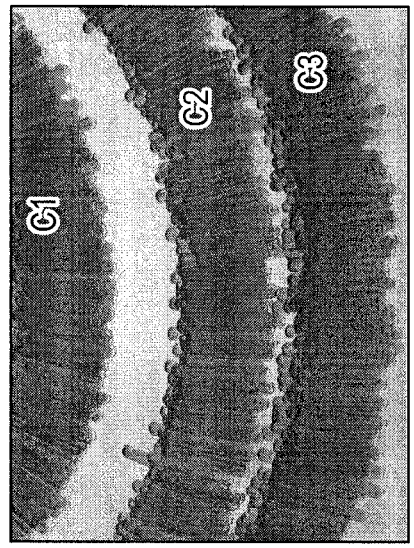
Figure 9G:
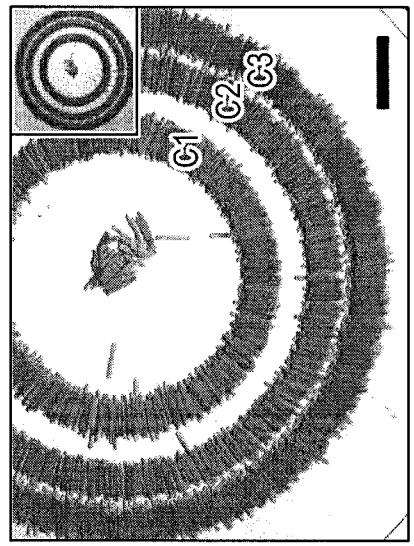
Figure 10A:
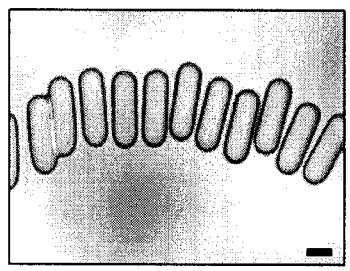
Figure 10B:
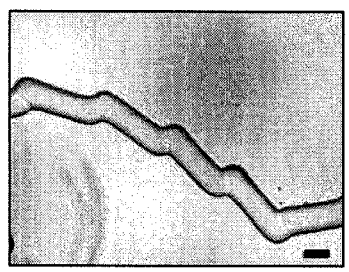
Figure 10C:
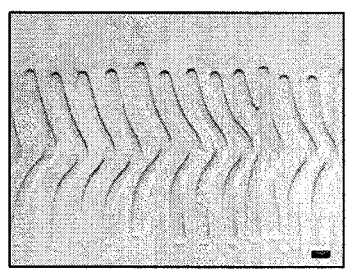
Figure 10D:
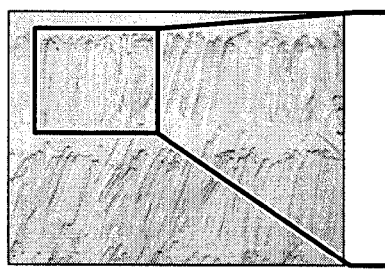
Figure 10E:
Figure 10F:
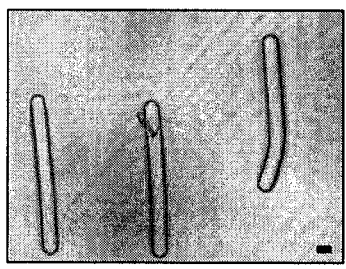
Figures 10G, 10H:

FIG. 9 shows various printed patterns of microrods, including a herringbone and a circular pattern. This figure shows that the gel objects within a network (such as rods) need not all be oriented in the same direction. For instance, herringbone patterning is shows in images a and b and circular patterning is shown in d, e, g and h. (a), (d) and (g) are bright field images of patterns in oil and (b), (e), and (h) are zoom-in images. (c) shows a Fourier analysis of directionality in (b). Image (f) shows the directionality of dual circular patterns (C1 and C2) in (d); (i) shows the directionality of tricircular patterns (C1, C2 and C3) in (g). Scale bar: 2 mm.

FIG. 10 shows DMT fabricated and patterned microrods of various shapes in high resolution. Images (a-e) show GelMa microrods (D=100 m) fabricated in the emulsification tubing of 100 μm in diameter. (a) shows monodisperse microrods and (b) shows a microrod chain, $\alpha$=3. Images (c-e) show curved and non-curved microrods ($\alpha$=20) patterned in parallel. Curved microrods were fabricated with a shorter incubation time in the tubing. Images (f-h) show GelMa microrods (D=50 μm) fabricated in the emulsification tubing of 50 μm in diameter. (f) Monodisperse microrods. $\alpha$=11. (g, h) Microrods ($\alpha$=30) patterned in parallel.

Figure 11:
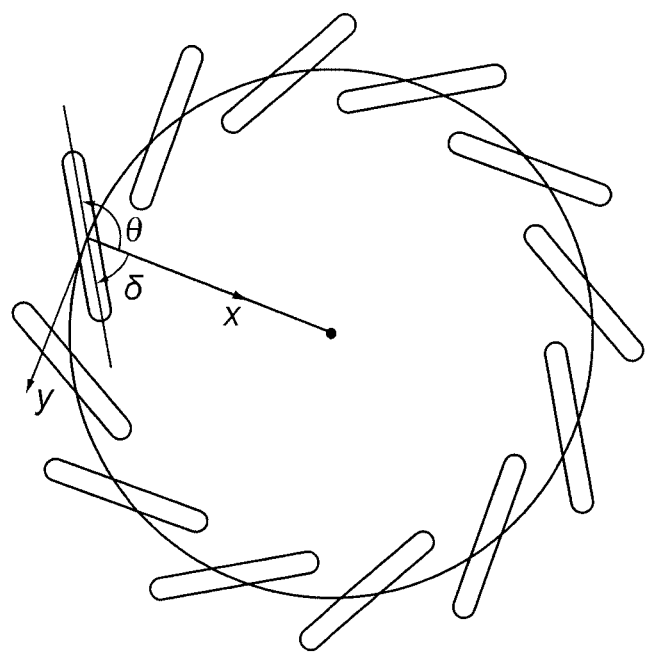
Figure 12A:
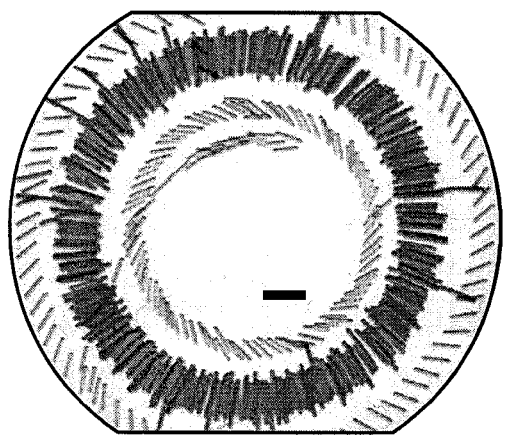
Figure 12B:
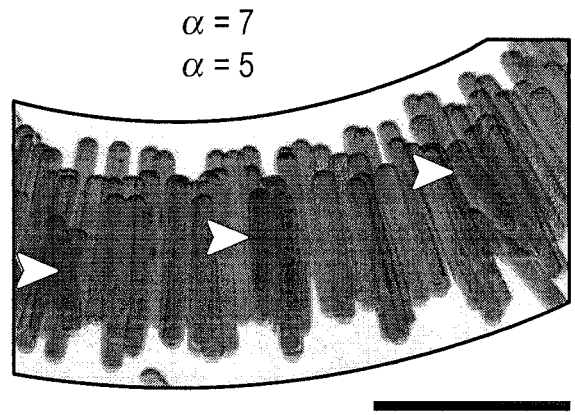
Figure 12C:
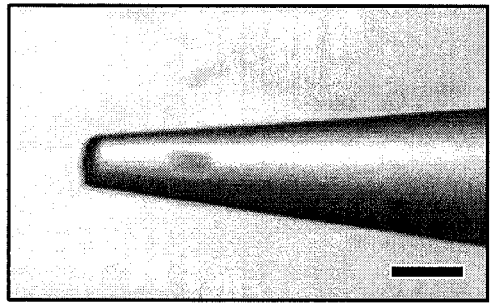
Figure 12D:
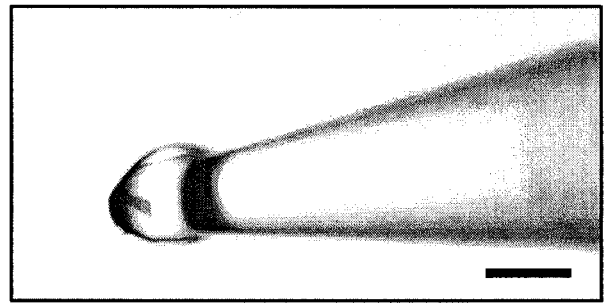
Figure 13D:
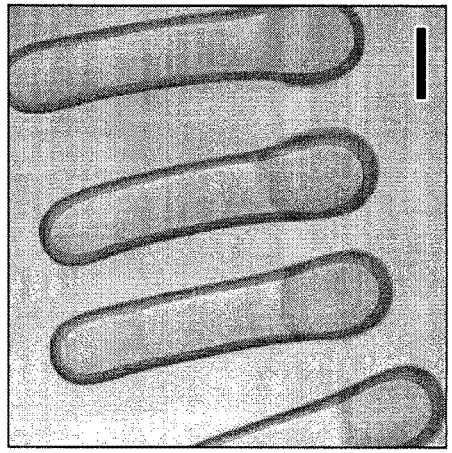
Figure 13E:
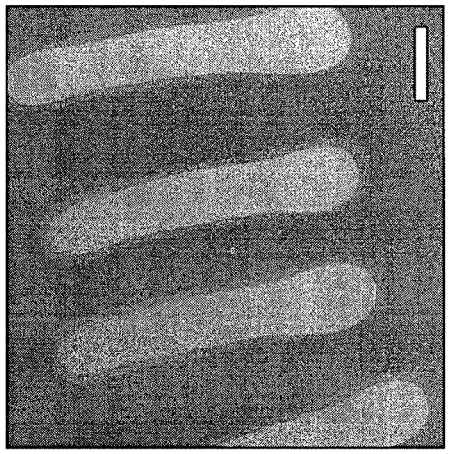
Figure 13C:
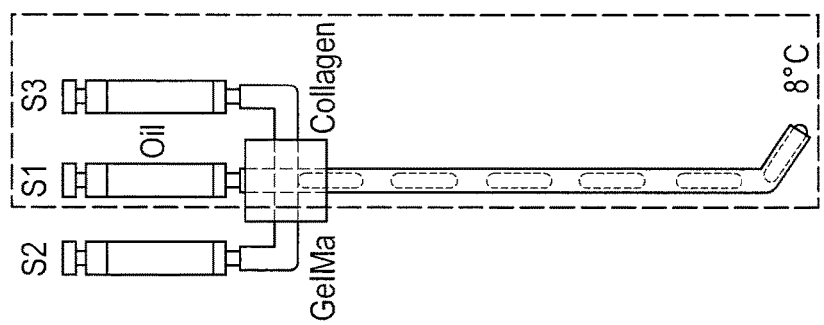
Figure 13A:
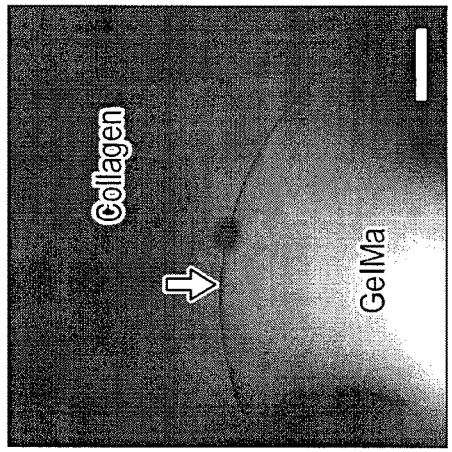
Figure 13B:
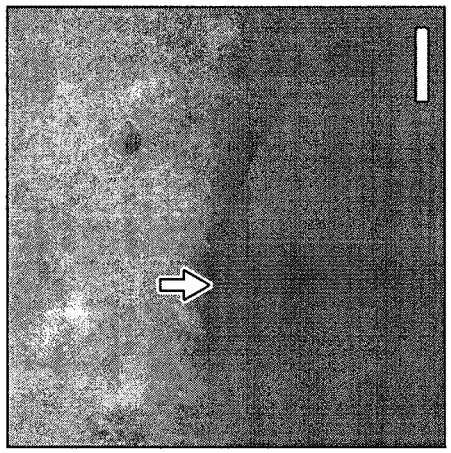
Figure 14B:
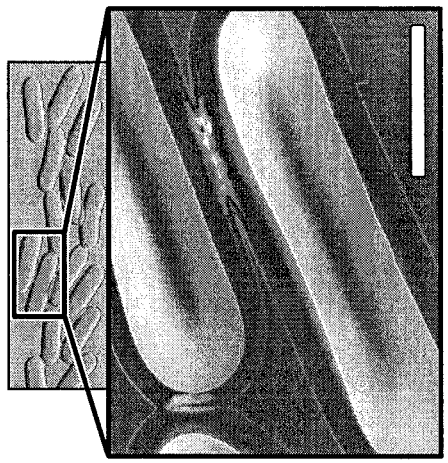
Figure 14A:
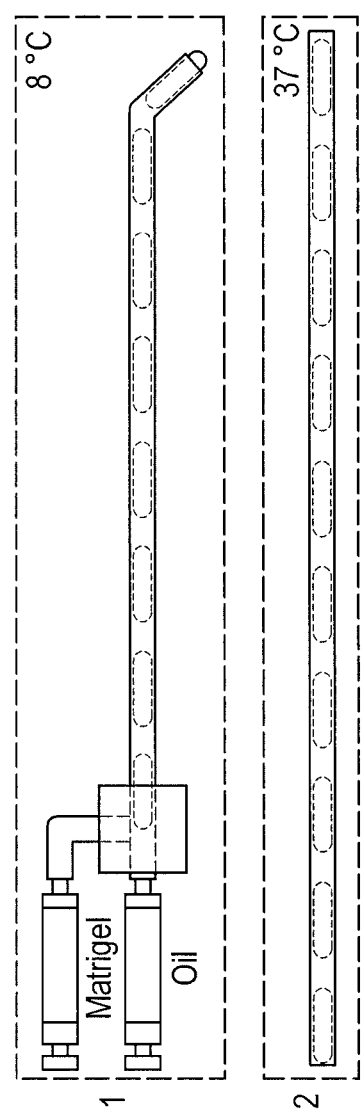
Figure 14D:
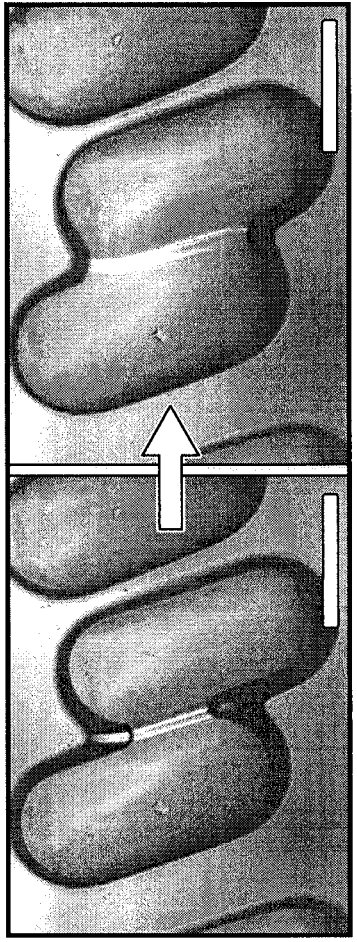
Figure 14C:
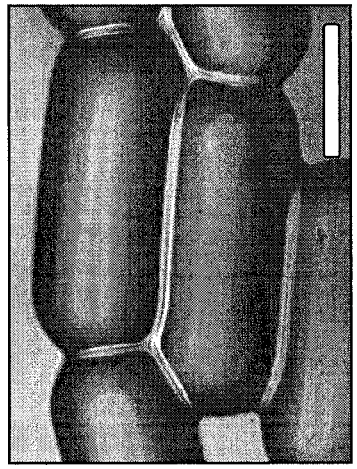
Figure 14E:
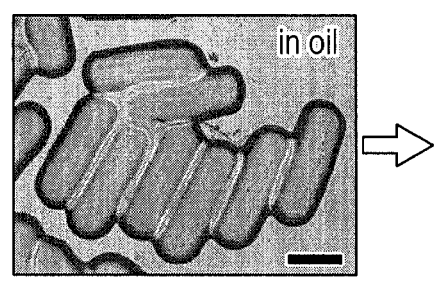
Figure 14F:
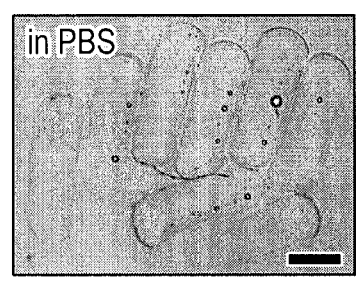
Figure 14G:
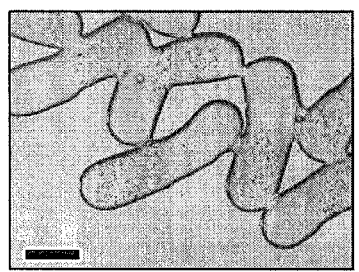

FIG. 11 illustrates the coordinate system used in the circular patterning by illustrating the variation of microrod direction $\theta$ with microrod rotation angle $\delta$.

According to the Jeffery's equation that applies in rigid microrods suspended in Newtonian fluids at low Reynolds number, the rotation angle $$\tan\delta = \frac{1}{\alpha}\tan\left[\frac{-\dot{\gamma}\cdot i\cdot\alpha}{\alpha^2+1} + \tan^{-1}(\alpha\cdot\tan\delta_0)\right]$$

$\delta_0$ is the value of $\delta$ at t=0, which is identical to the horizontal direction of the tilted end; $\alpha$ is the aspect ratio of the microrod; $\dot{\gamma}$ is the strain rate, and $$\dot{\gamma} \propto v.$$

As the tubing position is constant, we assume t is a constant value, $$\tan\delta = a\cdot\tan(-b\cdot v + c)$$

thus $$\theta = \frac{\pi}{2} - \delta = \frac{\pi}{2} - \arctan(a\cdot\tan(b\cdot v + c))$$

And $\theta$ (°) 90°−$\delta$=90°−57° ·$\tan^{-1}$(0.15 tan(10v−1.6)) after fitting the experimental data in FIG. 3c.

FIG. 12 shows the manipulation of a single microrod in oil. (a) Circular patterns of red microrods ($\alpha$=7, the middle of the three rings) and green microrods ($\alpha$=5, the outer and inner rings). (b) is a zoomed-in image of the red circular pattern doped with three green rods marked by white arrowheads. Images (c, d) show single pieces of (c) green and (d) red microrods aspirated into pipette tips. Scale bar: 2 mm.

FIG. 13 illustrates the formation of rods comprising two components, GelMa and collagen. The first step comprises homogeneously blending collagen I into GelMa microrods by DMT mixing (mixing in a microfluidic tube). Collagen I was the equal volume mixture of 3.6 mg/ml neutralised collagen (collagen type I, rat tail, Thermo Fisher Scientific, UK) and 1.0 mg/ml fluorescein conjugated collagen (D12060, Thermo Fisher Scientific, UK). The GelMa was 6.0 wt % in DPBS. Images (a, b) show separate regions of GelMa and collagen I, formed by depositing collagen beside gelled GelMa in a petri dish. The arrowheads indicate boundaries between collagen and GelMa. Fluorescence image shows clear separation of the two phases. Image (c) illustrates homogeneous mixing of GelMa and collagen I in DMT tubing. The GelMa and collagen phases were stocked at 40° C. and 8° C., respectively and instantaneously mixed at emulsification. Images (d, e) show microrods composed of a homogeneous blend of collagen I and GelMa formed at the volume flow rate ratio of 1:2. Scale bar: 200 μm.

FIG. 14 shows the fabrication of Matrigel microrods using the DMT system.

Image (a) Matrigel microrods formed in a PTFE tubing by replacing the GelMa phase in FIG. 1a with Matrigel. The solutions and tubings were stored at 8° C. The tubing was then detached from syringes, sealed and incubated at 37° C. for 2 hrs. After incubation, the tubing was connected to a syringe filled with oil and Matrigel microrods were pumped out of the tubing at controlled flow rate.

Images (b, c) are bright-field images of Matrigel microrods of different sizes in oil. Image (d) shows two time lapse images of microrods, the first taken at 2 minutes after being deposited in oil (left) and the second after 30 min incubation at 37° C. in oil (right).

The tubing was 1.2 m long and 300 μm in internal diameter (ID), and stored 100 μl solution.

Images (e-g) show bright-field and fluorescent images of (e) Janus rods, (f) ternary Matrigel rods and (g) chained Janus rods. The Janus rods in (e) were fabricated following the scheme in FIG. 5a, but replacing the red GelMa phase with Matrigel loaded with FluoSpheres® Polystyrene Microspheres, 10 μm, orange fluorescent (F8833, ThermoFisher Scientific, UK) at $7 \times 10^6$/ml and the green GelMa with pure Matrigel. The tubing was incubated at 37° C. for 2 hrs after emulsifying the particles-loaded Matrigel before proceeding to the secondary emulsification. Scale bar: 300 μm.

Figures 15A, 15B, 15C:
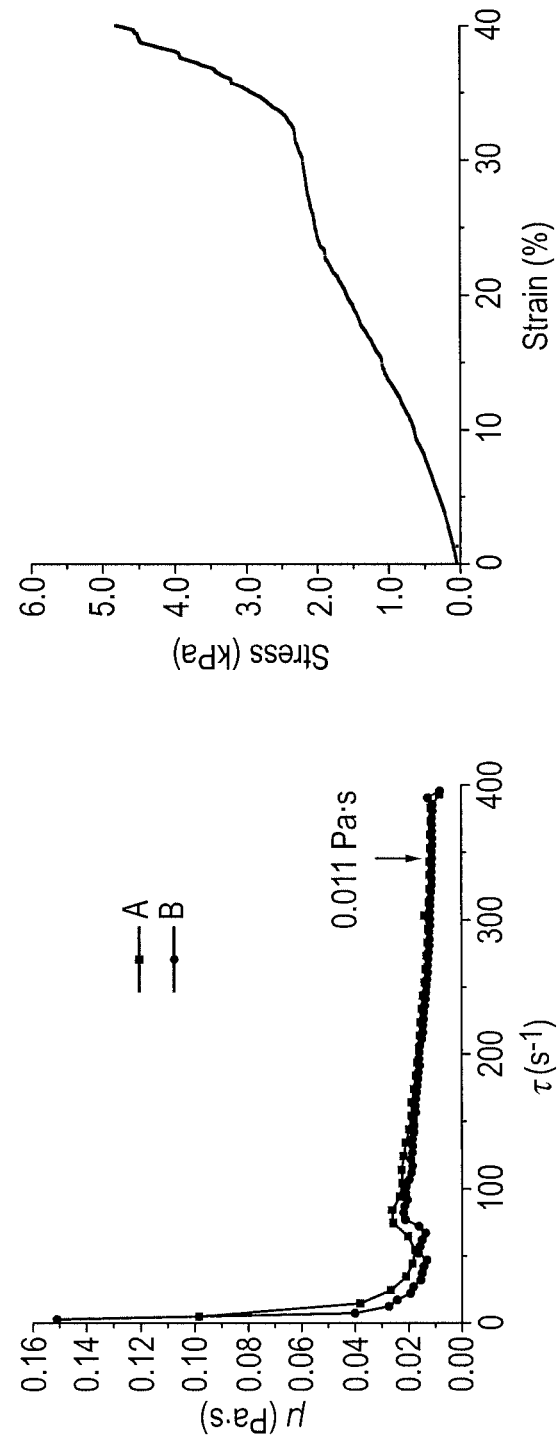
Figure 17E:
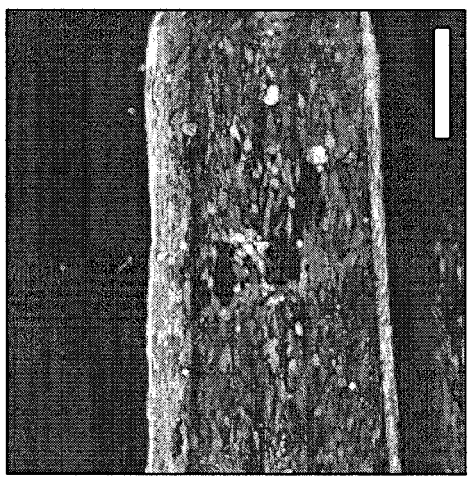
Figure 17F:
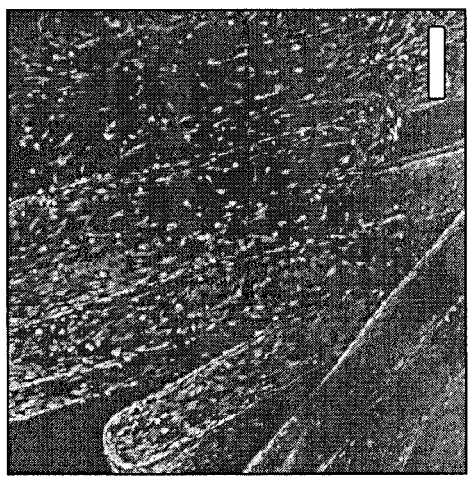
Figure 17C:
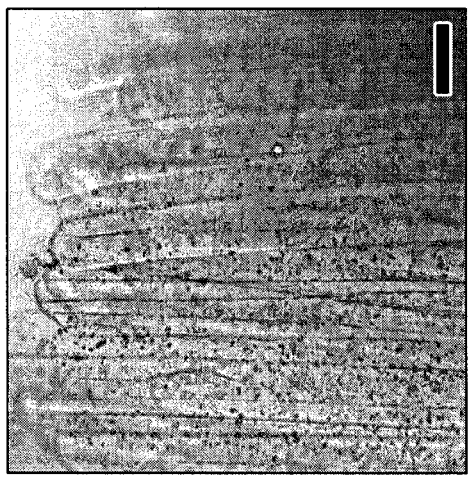
Figure 17D:
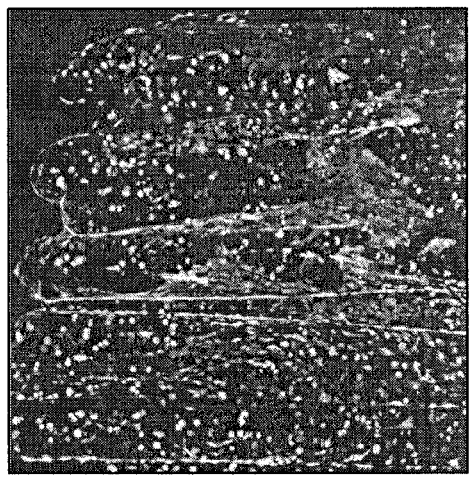
Figure 17A:
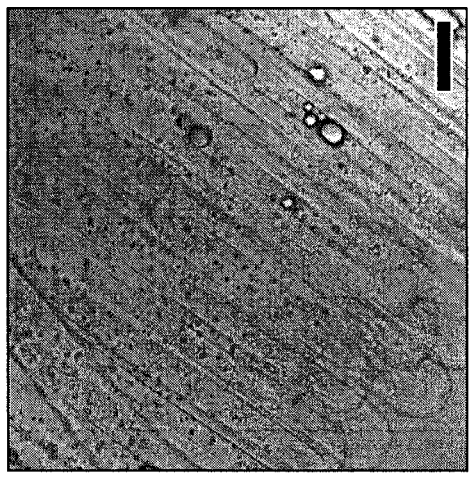
Figure 17B:
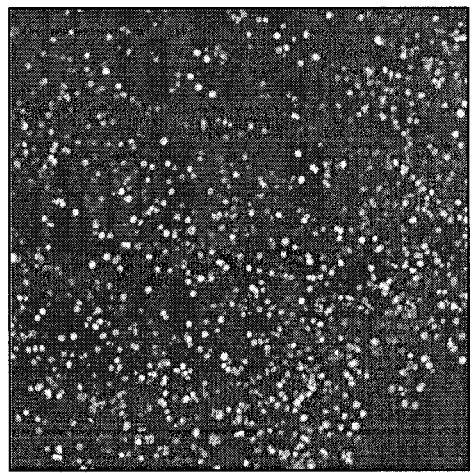

FIG. 15 shows the viscoelastic properties of 6.0 wt % GelMA in DPBS: (a) viscosity as a function of shear rate τ; (b) stress-strain curve, (c) list of viscoelastic moduli. The curve A (the upper curve in graph (a)) represents the initial viscosity and the curve B (the lower curve in graph (a)) is the viscosity after structure recovery for 10 min, taken on a strain-controlled rheometer (Gemini Advanced Rheometer, Bohlin Instruments, UK) at 37° C. The mechanical measurements were performed using a dynamic mechanical analyzer (DMA Q800, TA Instrument, UK) at 22° C. after UV crosslinking.

FIG. 16 shows a simulation of the hydrodynamic environment in tubing using Comsol Multiphysics. Diagram (a) shows the 2D axisymmetric model of a gel object in tubing. Images (b-d) are the contours of normalised (b) velocity magnitude, (c) in-plane shear ε and (d) extensional strain q derived from the velocity field in tubing: (b1) Single phase flow (SPF) of GelMa; (b2) low viscosity GelMa plug ($\mu_g$=0.01 Pa·s) in oil ($\mu_o$=0.002 Pa·s); (b3) high viscosity GelMa plug ($\mu_g$=100 Pa·s) in oil. In-plane shear and extensional strain rates were calculated from $\varepsilon=\partial \bar{u}/\partial z+\partial \bar{v}/\partial x$ and $\eta=\partial \bar{u}/\partial x+\partial \bar{v}/\partial z$, respectively. $\bar{u}$ and $\bar{v}$ are the longitudinal and transverse velocity components, respectively. Velocity magnitude u was normalised by $v_a$, i.e. $u/v_a$; shear components were normalised by $v_a/r$, i.e. $\varepsilon \cdot r/v_a$ and $\eta \cdot r/v_a$. Images (e-g) show the normalised frequency of (e) $u/v_a$ (f) $\varepsilon \cdot r/v_a$ (g) $\eta \cdot r/v_a$ in SPF and plugs of varying viscosities.

FIG. 17 illustrates the incorporation of NIH3T3 cells into gel objects. An NIH3T3 cell line stably expressing GFP (NIH-3T3/GFP) was cultured in and on GelMa rods. Images (a-d) show GelMa rods having cells therein. Cells were initially loaded into 6.0 wt % GelMa at $5 \times 10^6$/ml, and imaged at (a, b) day 4 and (c, d) day 15 in culture. Images (e-f) show GelMa rods having cells thereon. Cells were seeded onto photocrosslinked 6.0 wt % GelMa network at $1 \times 10^7$/ml in culture medium, supplemented with 10% v/v Matrigel, and cultured for 2 days. Scale bar: 200 μm.

FIG. 18 is a diagram showing how gel objects may be formed from gel precursor materials which undergo a sol-gel transition upon contact with a chelating agent.

FIG. 19 shows 3D cell culture in oriented GelMa microrods. Cells were loaded at $7.0 \times 10^6$ cells mL$^{-1}$ in 6.0% (w/v) GelMa in PBS, unless otherwise noted. (a, b) HEK293T cells in microrods after (a) 4 days (D4) and (b) 9 days (D9) in culture. Fluorescence images show live cells stained with calcein-AM (green) and dead cells stained with propidium iodide (red, almost no red spots visible in image). $Q_o$=250 μL h$^{-1}$; $Q_g$=450 μL h$^{-1}$. (c, d) NIH3T3/GFP cultured in a parallel microrod array. The cells were imaged both in bright field and GFP fluorescence at (c) day 4 and (d) day 15 in culture. $Q_o$=150 μL h$^{-1}$; $Q_g$=450 μL h$^{-1}$. (e) Human skeletal myoblasts (HSkM) cultured in a parallel microrod array for 10 days and stained with calcein AM (green). $Q_o$=180 μL h$^{-1}$; $Q_g$=450 μL h$^{-1}$. (f) Human colon myofibroblasts (CCD18Co) cultured for 5 days in a softer microrod (4.0% (w/v) GelMa). (g) CCD18Co cells cultured for 9 days in a stiffer microrod and microrod arrays (6.0% (w/v) GelMa). Corresponding bright-field images of the two microrod arrays are in FIG. 21. $Q_o$=180 μL h$^{-1}$; $Q_g$=450 μL h$^{-1}$. F-actin was labelled with phalloidin tagged with Alexa Fluor® 647 (magenta). Nuclei were labelled with DAPI (blue). Microrods in (a, f, g) are outlined in white. Yellow arrows in (g) indicate cells spread and migrated across adjacent rods.

Quantification of cell elongation and actin filament alignment in (d-g) was performed by anisotropic analysis of the green and magenta fluorescence signals with an ImageJ plug-in, FibrilTool. Anisotropy of the numbered images: (1) 0.19, (2) 0.11, (3) 0.36, (4) 0.17, (5) 0.07, (6) 0.04. Cells with scores above 0.07 show alignment discernible by eye. (h) Viability of different cell types over the course of 15 days by staining with calcein AM (live) and propidium iodide (dead). Data is shown at Day 2 and Day 9 for (columns left to right) HEK293T cells, NIH3T3/GFP cells, HSkM cells and CCD18Co cells. Data is shown at Day 15 for (columns left to right) HEK293T cells and NIH3T3/GFP cells. (i-l) Schematic (i) and fluorescence images (j-l) of 3D co-cultures of two different cell types in ternary GelMa microrods. HEK293T cells stained with CellTracker™ Red and NIH3T3/GFP fibroblasts (green) were suspended in GelMa (6% (w/v) in PBS) at $1.0 \times 10^7$ cells mL$^{-1}$ prior to plug formation in the tubing. The red-stained cells appear at either end of each rod while the green-stained cells appear in the middle section of each rod. (i) Ternary GelMa rods were formed by adjusting the flow rate ratio of the second (red)-to-first (green) phases to 2:3. Images 19 (j), (k) and (l) show 3D co-cultures of two different cell types in ternary rods (that is, rods containing three gel regions). Image 19 (j) shows ternary rods in oil (tetradecane) at 2 h after printing. (k, l) Ternary rods in medium after 1 day and 2 days in culture respectively. Microrods are outlined in white. $Q_o$=250 μL h$^{-1}$; $Q_g$=300–450 μL h$^{-1}$. Cell-laden microrods in all panels except (j) were photocrosslinked after being transferred to medium. Scale bars in all panels: 200 μm.

FIG. 20 shows Matrigel microrods and cells therein. (a) Schematic illustrating Matrigel microrod formation. The Matrigel, oil (tetradecane) and tubing were at 8° C. and Matrigel plugs were formed in the collection tubing. The collection tubing was detached from the syringe, sealed and incubated at 37° C. for 1 h. The tubing was 1.2 m long and of 300 μm ID, and could store approximately 100 μL of solution. After incubation, the tubing was reconnected to the syringe filled with oil and Matrigel microrods were extruded out of the tubing at a controlled flow rate ($Q_m$=500 μL h$^{-1}$)

at room temperature. (b) Bright-field images of Matrigel microrods (α=4) in oil. (c) Images of microrods at 2 min after deposition in oil at 37° C. (left) and after 30 min incubation at 37° C. (right). (d) Matrigel microrod network imaged in oil (left) and after transfer to PBS (right). (e) The Janus Matrigel rods were fabricated in the following steps: 1. Form Matrigel plugs (red) loaded with fluorescent polystyrene microspheres (FluoSpheres®, D=10 µm, orange) at $7.0\times10^6$ particles mL$^{-1}$ at 8° C.; 2. Incubate the plugs at 37° C. for 1 h; 3. Inject the second Matrigel phase (pure Matrigel, blue) at 8° C.; 4. Incubate the Janus plugs at 37° C. for 1 h; 5. Extrude the Janus rods from the tubing. (f, g) Bright-field (left) and fluorescence (right) images of (f) Janus and (g) ternary Matrigel rods. Ternary Matrigel rods were formed by increasing the flow rate ratio of the pure Matrigel to the particle-containing Matrigel by 50%. (h, i) 3D cell culture in a Matrigel microrod. NIH3T3/GFP cells were initially suspended in Matrigel at $1.0\times10^7$ cells mL$^{-1}$. Matrigel rods containing the cells were cultured in medium for 3 days. (h) z-Projection GFP fluorescence image of the cells in a rod and zoom-in image of a region. (top, left) Orthogonal views are shown of the xz and yz cross-sections across half the thickness of the rod. The arc of GFP fluorescence indicates that the cells were distributed primarily at the periphery of the microrods. (i) Fluorescence images of cells bridging two microrods, as indicated by the arrows. (j-l) 3D cell culture in a Matrigel microrod array. NIH3T3/GFP cells were initially suspended in Matrigel at $1.0\times10^7$ cells mL$^{-1}$. (j) Bright-field images of a cell-bearing Matrigel rod array deposited in oil for 1 h. (k, l) GFP fluorescence of the Matrigel rod array at (k) 1 h (D0) and (l) 3 days (D3) after transfer to medium. All imaging was performed at room temperature. $Q_o$=500 µL h$^{-1}$; volumetric flow rate of Matrigel, $Q_m$=300–1500 µL h$^{-1}$. Scale bars in all panels: 300 µm.

Figure 21:
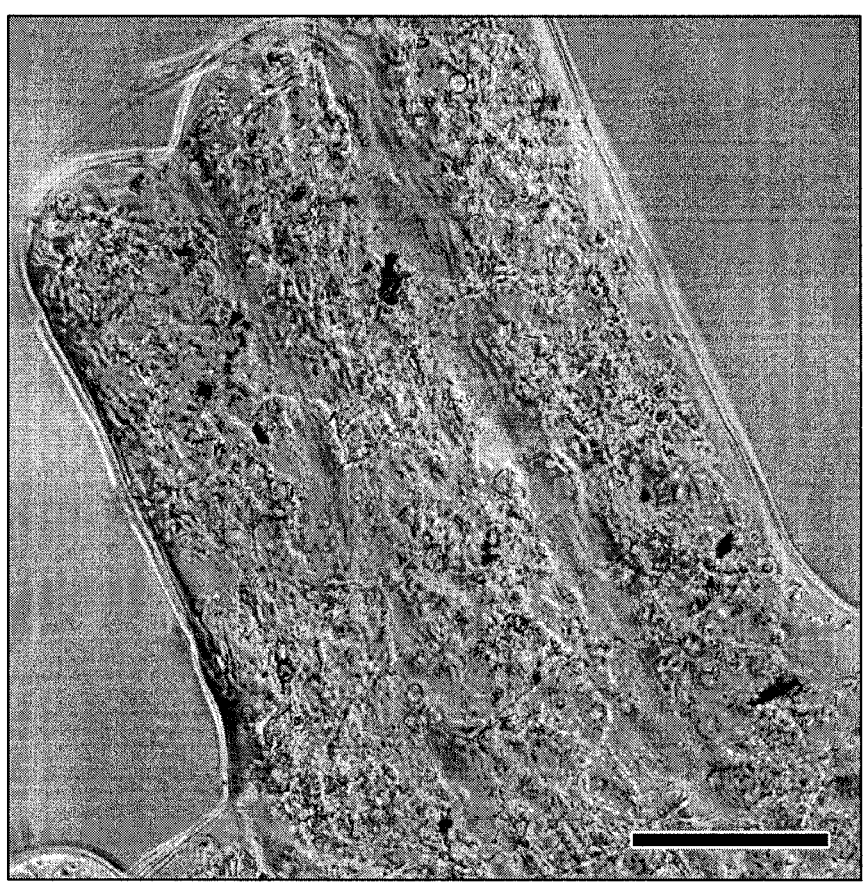
Figure 22A:
Figure 22B:
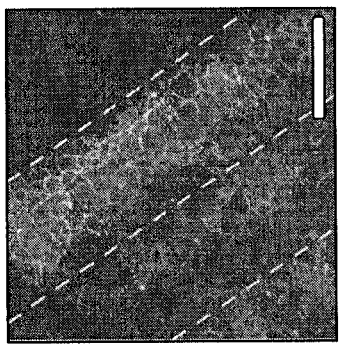
Figure 22C:
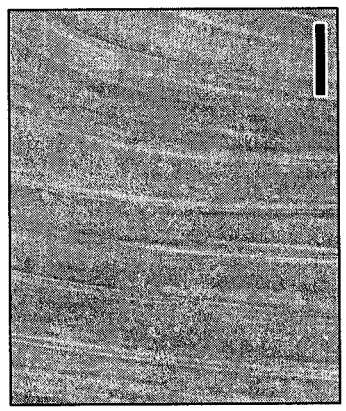
Figure 22F:
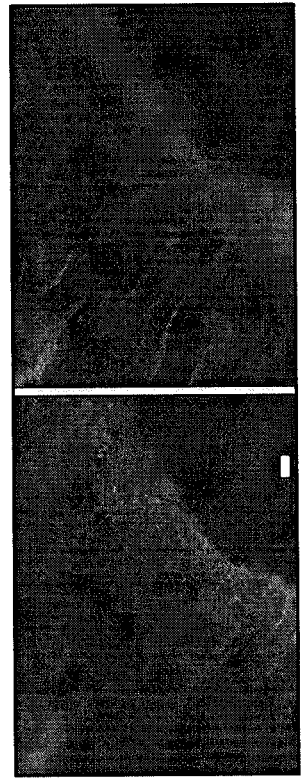
Figure 22E:
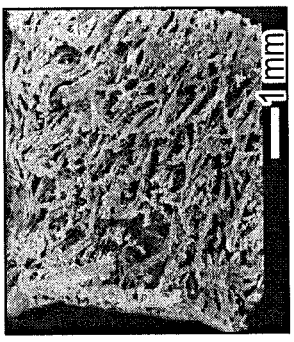
Figure 22D:
Figure 22G:
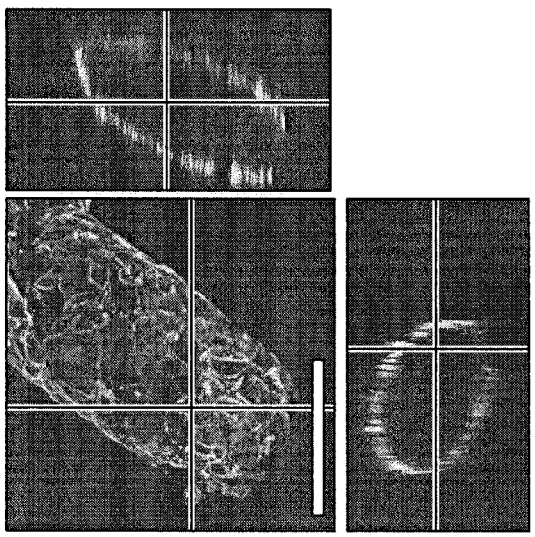
Figure 22H:
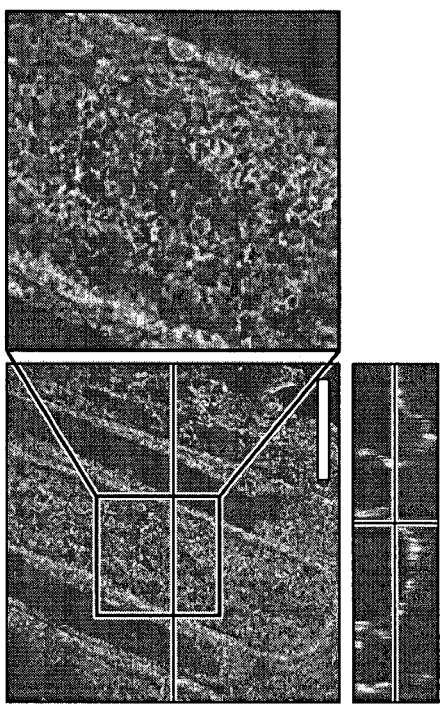
Figure 22I:

FIG. 21 is a bright-field image of a GelMa microrod array loaded with CCD18-Co cells. This image corresponds to the fluorescent image of the microrod array in FIG. 19g. Scale bar: 200 µm.

FIG. 22 shows human intestinal Caco-2 cells grown on GelMa microrods and rod arrays imaged after 3 weeks in culture. (a) Bright-field image of a GelMa microrod array grown with Caco-2. (b) Fluorescence image of Caco-2 cells immunostained with ZO-1 (tight junction protein-1) and conjugated to FITC after fixation. The dashed lines mark the interfaces between microrods. (c) Fluorescence image of Caco-2 cells stained with 2 µM calcium-AM prior to fixation. (d, e) A tube array after being lyophilised: (d) Bright-field imaging; (e) SEM imaging. (f) Fluorescence images of Caco-2 cells stained with DAPI (1:1000 dilution) on the rehydrated tube array, focused on two different heights. (g) Bright-field and (h) z-projection fluorescence images of a GelMa microrod array after fixation, immunostained with Alexa Fluor® 647 Phalloidin. (i) z-projection image of an isolated microrod from the rod array, stained with Alexa Fluor® 647 Phalloidin. Rectangular images in (h, i) show the fluorescence profiles along the yellow lines in the associated images across the thickness of the rods. Scale bars in all panels except noted otherwise: 200 µm.

FIG. 23 shows phase-transfer of a network by washing with a volatile and low-viscosity oil. Images (a) and (c) show two different networks printed in tetradecane. Images (b) and (d) show the two networks in PBS after phase transfer. Scale bars in all panels: 2 mm.

Figure 24C:
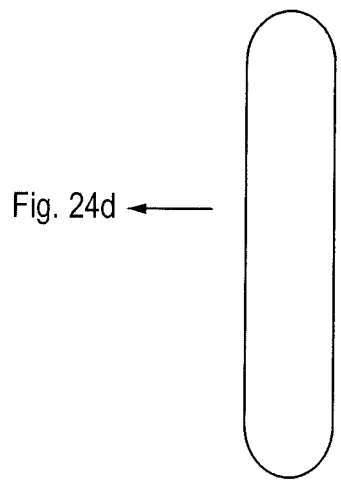
Figure 24D:
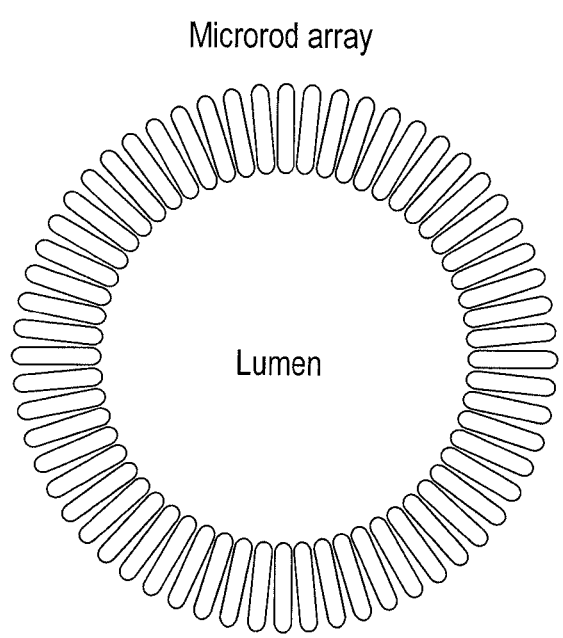

FIG. 24 illustrates how a tubular microrod array according to the invention mimics the structure of the intestine. Image (a) is a diagram of the small intestine. The lumen of the intestine tube is aligned with villus, which is illustrated in (b). The villus has a microrod-like morphology (c), thus the inner layer of the small intestine might be reconstituted by a tubular array of gel microrods (d). Images (a, b) were purchased from Can Stock Photo Inc., Canada and reedited.

DETAILED DESCRIPTION OF THE INVENTION

The invention provides a process for producing a gel network, which network comprises a plurality of joined gel objects, which process comprises:
   forming a plurality of gel objects in one or more microfluidic channels;
   dispensing the gel objects from the one or more microfluidic channels into a region for producing the network; and
   contacting each gel object with at least one other gel object in said region for producing the network, to join each gel object to at least one other gel object at a region of contact between the gel objects.

The invention further provides a network of joined gel objects comprising a plurality of gel objects wherein each gel object is joined to an adjacent gel object at a region of contact between the gel objects. Various embodiments of the process and the gel network of the invention will be discussed below.

Gel Objects

The term "gel object" as used herein refers to a volume of a material comprising a gel, and which is at least partially gelled. The gel object may therefore have a fixed shape depending on the extent of gelling that has occurred. At the point of formation in the one or more microfluidic channels, the gel objects may not have gelled enough yet to have a fixed shape. However, at this point, the walls of the microfluidic channel will impose a shape on the gel object. Typically, as the gel objects progress through the microfluidic channels, more and more gelling occurs such that, by the time the gel objects are in contact with one another in the region for producing the network they are fully gelled, or nearly fully gelled and will have their own fixed shapes. The shape of the gel object is not particularly limited. The gel object may be, for example, a sphere or elongated into a rod. An approximately spherical gel object may be referred to herein as a droplet. The cross-section of the gel objects, whether they have an elongated shape or not, is not particularly limited in its shape. By "cross-section" is meant the cross-section taken perpendicular to the longest dimension of the gel object. The cross-section of the gel objects is typically a circle, square or rectangle; or any other polygon, for instance a hexagon. A particular cross-section may be achieved by employing a microfluidic channel having that cross-section. Preferably the gel object has a circular cross-section; more preferably the gel object is a rod.

The term rod as used herein is taken to mean an object having a length greater than its diameter. The length of an object is taken to be the largest dimension of the object and the diameter of an object is the largest dimension of a cross-section of the object taken perpendicular to the axis lying along the length of the object. The length of a rod is typically at least 10% greater than its diameter, for example at least 50% or 100% greater than its diameter. Typically, a rod has a substantially cylindrical shape. It may for instance have a cylindrical shape.

The gel objects are not particularly limited as to their size. They are typically from 10 to 2000 µm or 10 to 1000 µm in diameter, for example from 10 to 500 µm in diameter or 25 to 250 μm in diameter. A particular diameter of gel object may be achieved by employing a microfluidic channel having that same diameter. The gel objects are typically from 1 μm to 10 mm in length or from 10 μm to 10 mm in length, for example from 10 μm to 5 mm in length or from 100 μm to 2.5 mm in length. A particular length may be achieved by controlling the amount of gel precursor material employed for forming a particular gel object in a microfluidic channel. The gel objects typically have a volume of from $1.0 \times 10^{-7}$ μl to 10 μl, for instance from $1.0 \times 10^{-5}$ to 1.0 μl, or for example from $1.0 \times 10^{-3}$ μl to 1 μl or from $1.0 \times 10^{-3}$ μl to 0.1 μl. The gel objects may for instance have a volume of from 0.005 μl to 0.05 μl, for example from 0.01 to 0.03 μl.

The gel objects comprise a gel. A gel may be defined as a "nonfluid colloidal network or polymer network that is expanded throughout its whole volume by a fluid". The nonfluid component of a gel, which is capable of forming the gel when expanded with a fluid, is referred to herein as a gel-forming agent. The gel-forming agent may, for instance, be polymeric or colloidal. A gel therefore comprises a network of the gel-forming agent which is expanded throughout its volume (i.e. swelled) by the fluid. The process of forming a gel from the fluid and the gel-forming material is referred to as "gelling".

A gel object is at least partially gelled. It may be fully gelled, or partially gelled. Thus, in addition to the gel, a gel object may further comprise a gel precursor material. A gel precursor material is a flowable (typically liquid) medium that has not yet gelled, comprising the gel-forming agent and the fluid. Gel is formed by the gelling of a gel precursor material. When a gel object comprises both gel and gel precursor material, the gel object is only partially gelled. Such a gel object may be described as "incompletely gelled". When a gel object does not comprise (i.e. no longer comprises) gel precursor material it is "fully gelled".

Typically, in the process of the invention, the plurality of gel objects that are formed in the one or more microfluidic channels are incompletely gelled. This has the advantage that, when the gel objects are subsequently contacted with one another in the region for producing the network, the gel objects join very efficiently to one another at the regions of contact between the gel objects. Indeed, if the gel objects are incompletely gelled, they fuse together at the regions of contact between the gel objects and further gelling occurs at those regions, to join the gel objects together.

The nature of the gel, and of the gel particles from which a gel may be formed, is not particularly limited. An exemplary gel which may be used is a hydrogel, for instance agarose gel, a gelatin hydrogel or a gelatin methacrylate hydrogel. A hydrogel may be defined as "a gel in which the swelling agent (i.e. the fluid) is water". A hydrogel is produced by the gelling of an aqueous solution of a gel-forming agent. In the case of a hydrogel, the gel-forming agent may be referred to herein as a hydrogel compound. Any suitable hydrogel compound may be employed. The hydrogel compound is typically polymeric. For instance, the hydrogel compound may be a polysaccharide, a polyvinyl alcohol, a polyacrylate, a polymer comprising a number of hydrophobic groups or a derivative thereof. The hydrogel compound is typically a polysaccharide. Examples of hydrogel compounds include agarose, methylcellulose and hyaluronan. Preferably, the hydrogel compound is agarose, gelatin or gelatin methacrylate. More preferably, it is gelatin or gelatin methacrylate. The gel-forming agent may therefore be a gel-forming agent which comprises gelatin. The gel-forming agent which comprises gelatin may, for instance, be gelatin or gelatin methacrylate.

The concentration of the gel-forming agent (for example a hydrogel compound) in the fluid (which may, for example, be an aqueous medium, such as water or cell-growth medium) is typically from 0.01 mg/L to 500.0 mg/L. For instance, the concentration of the gel-forming agent in the fluid may be from 0.1 mg/L to 100.0 mg/L, or from 0.5 mg/L to 30.0 mg/L.

Another example of a gel is a matrix of crosslinked colloids. In this instance, the gel-forming agent which is used to form the gel comprises crosslinkable colloid particles, and the gel precursor material from which the gel is formed is a suspension comprising crosslinkable colloid particles. Other examples of gels include gels comprising polymers which may be cross-linked by photoinitiated polymerisation, or by thermally-induced polymerisation.

Another example of a gel is a polymer matrix cross-linked by the chelation of ions. An example of a gel formed by ion chelation is an alginate gel. An alginate gel comprises polymers which are cross-linked by ion chelation. In this instance the gel-forming agent which is used to form the gel comprises crosslinkable polymers, and the gel precursor material from which the gel is formed is a suspension or solution comprising crosslinkable polymers. Cross-linking between polymers is initiated in the gel precursor material by the addition of a chelating agent. A chelating agent in this context is typically an ion, for instance a cation. The ion is typically a metal ion, for instance a metal cation. A chelating agent in this context is usually a divalent ion, for example a divalent metal cation, e.g. an alkaline earth metal dication, for instance a calcium ion.

The gel may be biological in origin. For instance, the gel may comprise collagen derived from animals. Another example of a biologically-derived gel is Matrigel. Biologically-derived gels may be particularly suitable for forming gel networks which support biological cells.

Preferably the gel object comprises a hydrogel. Preferably, the gel precursor material from which the gel is formed therefore comprises the gel-forming agent (which may be referred to as a hydrogel compound) and water. The flowable gel precursor material from which the gel is formed may therefore be an aqueous medium. The aqueous medium typically comprises at least 80% water by weight, for example at least 90% water by weight.

Another exemplary gel is a polymer which is covalently cross-linked. Covalent cross-linking is typically photoinitiated, e.g. by ultraviolet light, or thermally initiated, e.g. by heating. In this instance, the gel-forming agent comprises non-cross-linked polymer, and the flowable, gel precursor material comprising the gel-forming agent may be any liquid comprising non-cross-linked polymer.

In addition to gel (and, when present, gel precursor material), a gel object may comprise other materials, compounds or substances. For instance, the gel object may contain at least one small molecule, such as a dye, or a magnet. Suitable dyes include, but are not limited to, fluorescein and 5-cTAMRA (5-carboxytetramethylrhodamine). Alternatively, the gel object may contain at least one sensor molecule, for instance a sensor molecule that it sensitive to a particular chemical or is a light-sensitive molecule.

In some embodiments, gel objects comprise a therapeutic agent, such as a prodrug, or a diagnostic agent, such as a contrast agent. For instance, a therapeutic agent or diagnostic agent may be present in the gel objects, and hence in the hydrogel network of the invention.

In some embodiments, gel objects comprise biological compounds, or a mixture of biological compounds. By "biological compound" is meant a compound which may be found in vivo, for example in the human body. Examples of biological compounds include proteins, e.g. enzymes. Mixtures of biological compounds include, for example, gastric juices.

In another embodiment, gel objects may comprise biological cells. The term "biological cell", as used herein, is well known and refers to a cell comprising a cytoplasm (typically comprising organelles such as a nucleus or a ribosome) enclosed within a membrane. The biological cells used in the process of the invention may be prokaryotic or eukaryotic. The biological cells are typically eukaryotic. The biological cells may be naturally occurring or genetically (or otherwise) modified. Often, the biological cells are mammalian cells derived from mammalian tissue, for instance mouse, rat, sheep or human tissue. For instance, the biological cells may be derived from primate tissue such as human or chimpanzee tissue.

In some embodiments, the one or more biological cells are selected from two or more different types of biological cells.

The invention therefore provides a gel network according to the invention wherein the gel objects comprise biological cells. A type of a biological cell refers to the cell type of a biological cell taken from a particular species. For instance, typical examples of mammalian biological cell types include human embryonic kidney (HEK) cells, osteoblast cells, chrondrocyte cells and mesenchymal stem cells. Usually, the said biological cells are mammalian cells, in particular human cells. In some embodiments, the said biological cells are primary cells. For example, the biological cells may be selected from one or more of human embryonic cells, stem cells, fibroblasts, myoblasts, myofibroblasts and human intestinal cells such as human colon cells. The biological cells may in particular be selected from HEK293T cells, NIH3T3 cells, NIH3T3/GFP cells, human skeletal myoblasts (HskM), human colon myofibroblasts (CCD18-Co), and human intestinal Caco-2 cells.

The biological cells are typically living cells. Typically, the biological cells are present in the gel objects at a concentration of 0.7 to $1.0 \times 10^7$ cells $mL^{-1}$.

In some embodiments of the process of the invention, the process is a process for producing a network of joined gel objects wherein one or more of the gel objects comprise biological cells. In some embodiments, the cells are incorporated into the gel objects as they are formed. For instance, where the process comprises forming the gel objects in the one or more microfluidic channels from a flowable gel precursor material, which gel precursor material comprises a gel-forming agent and a fluid, the flowable gel precursor material comprises biological cells. In other embodiments, the process of the invention may comprise a step of inserting biological cells into one or more gel objects after they are formed. For example, biological cells may be inserted into one or more gel objects which form part of a network.

The said biological cells employed in the process of the invention are usually mammalian cells, in particular human cells. In some embodiments, the said biological cells are primary cells. For example, the biological cells may be selected from one or more of human embryonic cells, stem cells, fibroblasts, myoblasts, myofibroblasts and human intestinal cells such as human colon cells. The biological cells may in particular be selected from HEK293T cells, NIH3T3 cells, NIH3T3/GFP cells, human skeletal myoblasts (HskM), human colon myofibroblasts (CCD18-Co), and human intestinal Caco-2 cells.

In some embodiments, gel objects may comprise bacteria. Typically, the bacteria are bacteria which are commonly found in or on the human body, for instance gut bacteria. In one aspect of this embodiment of the invention, the gel network may comprise different regions containing different types of gut bacteria.

In some embodiments of the invention, the composition of the gel objects may be chosen to give them a particular optical property, for instance a particular colour, refractive index, or transparency. For example, the colour, refractive index, or transparency of the gel objects may be varied by varying their composition. Variation of the optical properties of the gel objects within a network may have uses in, for example, liquid crystal displays.

In some embodiments of the invention, the composition of the gel objects may be chosen to give them temperature-dependent properties. For instance, the gel objects may comprise substances which deform, for example which shrink or expand, when heated and/or cooled. The gel network of the invention may have very useful applications when designed in this way, for example as a temperature-dependent switch. Alternatively, the gel network of the invention may achieve temperature-dependent deformation by virtue of the orientation of the objects within it. An example of such behaviour is illustrated in FIG. 2, images (i), (j) and (k), wherein sheets of microrods adopt a particular shape in hot water and a different shape in cold water.

In some embodiments of the invention, one or more of the gel objects, for instance at least some of the gel objects, or for example all of the gel objects, comprise regions of differing composition. Thus, in some embodiments of the invention, the gel objects comprise gel objects which have regions of differing composition.

Typically, the regions of differing composition in each such gel object comprise a first region and a second region, the first region having a composition which is different from that of the second region.

The first region may for instance comprise a material, for instance a compound, which is absent from the second region, and/or the second region may comprise a material, for instance a compound, which is absent from the first region. Additionally or alternatively, the first and second regions may both comprise a particular material, for instance a particular compound, but at different concentrations. For instance, the concentration of the material (e.g. compound), in the first region may be at least twice the concentration of the material (e.g. compound) in the second region. The concentration of the material (e.g. compound), in the first region may for instance be at least ten times, for example at least 100 times, at least 1,000 times, or at least 1,000,000 times, the concentration of the material (e.g. compound) in the second region.

As will be described further below, the material (or compound) in question may for instance be a particular gel, a particular gel-forming agent, biological cells, a particular type of biological cell, or a particular small molecule compound. The material may for instance be a therapeutic agent, diagnostic agent, biological compound (for instance a protein or enzyme or nucleic acid, for instance a membrane protein, e.g. a membrane pore protein) or biological cells (e.g. mammalian cells, for example mammalian cells selected from human embryonic kidney (HEK) cells, osteoblast cells, chrondrocyte cells and mesenchymal stem cells; or for instance bacteria, for example bacteria which are commonly found in or on the human body, for instance gut bacteria).

The regions of differing composition may further comprise a third region, the third region having a composition which is different from that of the first region and also different from that of the second region. The composition of the third region may differ from that of the first or second region as defined above for difference between the first and second regions.

In each such gel object, the regions of differing composition may be located adjacent one another.

Often, regions of differing composition (which may be first and second regions, as defined above) are arranged at either end of a gel object, which may for example be a rod-shaped gel object.

In some embodiments, first and second regions of differing composition, as defined above, are located adjacent one another in a rod-shaped gel object, and extend to opposite ends of the gel object.

Alternatively, the regions of differing composition may comprise one region within (i.e. encapsulated by or surrounded by) another region.

For instance, the gel objects may contain gel regions adjacent to one another, e.g. arranged at either end of a rod-shaped gel object, wherein each gel region contains a different type of gel. Alternatively, the gel objects may contain gel regions within one another, wherein the centre of a gel object is encapsulated with a different type of gel.

Typically, the regions of differing composition within a gel object comprise the same kind of gel but differing additional components, for example different kinds of biological cell or small molecule. Alternatively, the differing regions of the gel objects may comprise different kinds of gel, for example different kinds of polymer e.g. different kinds of hydrogel. There are numerous advantages associated with using different kinds of gel. For example, two different kinds of gel may have different responses to a temperature changes and may therefore cause deformation of the gel object (and hence the gel network) upon heating or cooling. Differing gels may be compatible with different components. For instance, a gel formed from a hydrophilic polymer may be unable to carry a salt, but able to carry biological cells, and thus in order to incorporate both components into a single gel object, it may be convenient to create a gel object having regions comprising different kinds of gel.

A further area where gel objects having different regions with different properties may be useful is in tissue bonding, in particular in regenerative medicine, e.g. in tissue repair such as organ repair. The invention therefore provides the use of a network according to the invention in regenerative medicine, for example in organ repair or tissue repair. In some embodiments of the invention, the network of gel objects may be attached to living tissue. According to this embodiment of the invention, therefore, the gel network comprises gel objects which will attach to living tissue. However, it is possible that the network may also be required to have a side which does not stick to tissue but rather releases a chemical into the bloodstream. It is therefore desirable to produce a network comprising gel objects having a region which will attach to the tissue and another region which will not.

Another situation where gel objects having regions of different composition are useful is where it is desired that the gel objects do not join to one another at all regions of contact between the gel objects. For instance, in the formation of a model of the intestine, it is desirable to produce a network of rods which are attached at one end but not at the other, in order to mimic the structure of the endothelium. It is therefore desirable, in situations such as these, to produce networks of gel objects, for instance rods, which are attached at or near one end but not at or near the other end. Gel objects which join to one another at particular regions may be produced by creating objects having regions of different gels, some of which regions are more able than others to interact with other gel objects. This may be achieved by, for instance, forming the gel objects from flowable media which gel at different rates, or forming the gel objects from flowable media which gel to differing extents at the same temperature, or by otherwise controlling the extent to which gelation occurs in the gel objects during their formation.

Preferably, the gel objects having regions of differing composition are Janus rods. A janus rod is a rod-shaped gel object (a rod being as defined above) comprising a first region and a second region, wherein the first region has a composition which is different from that of the second region. Generally, the first region is at one end of the rod and the second region is at the other (opposite) end of the rod. Often, Janus rods have only two regions (i.e. a first region and a second region) of differing composition, one being at one end of the rod and the other being at the other end of the rod. In such cases, the first and second regions will also be adjacent one another and will meet or merge at some point along the length of the rod (typically at or near the middle of the rod's length). Alternatively, however, Janus rods may have multiple regions of differing composition along their length, for instance at least three regions of differing composition. A janus rod may for instance further comprise at least one further region, each further region having a composition which is different from that of the first region and also different from that of the second region. For instance, the first region may be at one end of the rod, the second region may be at the other (opposite) end of the rod, and the at least one further region may be situated in between the first and second regions. The at least one further region may for instance be located at a middle portion of the rod, which middle portion is located in between the two distal ends of the rod. The at least one further region may for instance be one further region, which may be referred to as a third region.

Thus, in some embodiments of the invention, one or more of the gel objects, for instance at least some of the gel objects, or for example all of the gel objects, are janus rods. Thus, in some embodiments of the invention, the gel objects comprise janus rods.

In some embodiments of the invention, one or more of the gel objects, for instance at least some of the gel objects, or for example all of the gel objects, are rod-shaped gel objects, each of which comprises a first region and a second region, the first region having a composition which is different from that of the second region. Typically the first region is at one end of the rod and the second region is at the other end of the rod.

The first region of the janus rod may comprise a material, for instance a compound, which is absent from the second region, and/or the second region of the janus rod may comprise a material, for instance a compound, which is absent from the first region of the janus rod. Additionally or alternatively, the first and second regions of the janus rod may both comprise a particular material, for instance a particular compound, but at different concentrations. For instance, the concentration of the material (e.g. compound), in the first region of the janus rod may be at least twice the concentration of the material (e.g. compound) in the second region of the janus rod. The concentration of the material (e.g. compound), in the first region of the janus rod may for instance be at least ten times, for example at least 100 times, at least 1,000 times, or at least 1,000,000 times, the concentration of the material (e.g. compound) in the second region of the janus rod. The material (or compound) in question may for instance be a particular gel, a particular gel-forming agent, biological cells, a particular type of biological cell, or a particular small molecule compound. The material may for instance be a therapeutic agent, diagnostic agent, biological compound (for instance a protein or enzyme, for instance a membrane protein, e.g. a membrane pore protein) or biological cells (e.g. mammalian cells, for example mammalian cells selected from human embryonic kidney (HEK) cells, osteoblast cells, chrondrocyte cells and mesenchymal stem cells; or for instance bacteria, for example bacteria which are commonly found in or on the human body, for instance gut bacteria).

The first and second regions of the janus rod, as defined above, may be located adjacent one another (e.g. at or near the middle or the rod's length) and extend to opposite ends of the janus rod.

A janus rod may for instance further comprise a third region, the third region having a composition which is different from that of the first region and also different from that of the second region. For instance, the first region may be at one end of the rod, the second region may be at the other (opposite) end of the rod, and the third region may be situated in between the first and second regions. The third region may for instance be located at a middle portion of the rod, which middle portion is located in between the two distal ends of the rod. These rods are referred to as ternary rods.

Gel Networks

The term "gel network" or "network" as used herein typically refers to a two-dimensional (2D) or a three-dimensional (3D) network, typically a three-dimensional network, of gel objects as described above. The gel network typically comprises at least 50 gel objects, for instance at least 100 gel objects or for example at least 1,000 gel objects. It may for instance comprise at least 100,000 gel objects, for instance at least 500,000 gel objects. The gel network typically comprises from 50 to 1,000,000 gel objects, for example from 100 to 500,000 gel objects or from 1,000 to 100,000 gel objects.

The gel network may be any shape or size. For example, the network may be a sheet, a cuboid, a cylinder, or a chain. The network may mimic the shape of tissue, for example the shape of a muscle or a portion of the intestine (as shown in FIG. 24). The network is typically large compared to the size of an individual object. Thus, the largest dimension of the network, e.g. its length, is typically at least 5 mm, for instance at least 1 cm. It may for instance be at least 2 cm, for example at least 4 cm. The largest dimension of the network, for instance its length, may be from 5 mm to 10 cm, and may, for instance be from 1 cm to 10 cm, for instance from 2 cm to 10 cm. However, if the network comprises, for instance, a single layer of joined gel objects then the thickness of the network will be only as thick as an individual gel object, for example from 10 µm to 10 mm.

The volume of the gel network of the invention, or the gel network produced by the process of the invention may be, for instance, at least 1 mm$^3$ or at least 0.2 cm$^3$, for instance at least 0.5 cm$^3$. It may for instance, have a volume of at least 1 cm$^3$, for example at least 2 cm$^3$, or for instance at least 5 cm$^3$, at least 10 cm$^3$, or at least 20 cm$^3$. The volume of the gel network may, for instance, be less than 500 cm$^3$, for instance less than 200 cm$^3$ or less than 100 cm$^3$, for example less than 80 cm$^3$. The volume of the gel network may, for instance, be from 1 mm$^3$ to 500 cm$^3$ for instance from 0.2 cm$^3$ to 200 cm$^3$. The network may for instance, have a volume of from 0.5 cm$^3$ to 100 cm$^3$ for example from 1 cm$^3$ to 80 cm$^3$, or for instance from 3 cm$^3$ to 20 cm$^3$. The volume of the gel network may, for instance, be from 0.2 cm$^3$ to 50 cm$^3$ for instance from 0.5 cm$^3$ to 20 cm$^3$. The network may for instance, have a volume of from 1 cm$^3$ to 17 cm$^3$ for example from 2 cm$^3$ to 14 cm$^3$, or for instance from 5 cm$^3$ to 12 cm$^3$.

The gel objects within the gel network may be closely-packed. In a closely-packed network, a significant fraction of the volume of the network is filled with gel objects. Typically at least 40% of the volume, for example at least 50% or at least 60%, is filled with gel objects in a closely-packed network.

However, the process of the invention allows regions of space to be left unfilled by gel objects. The precise location and orientation of the gel objects is controlled by the process of the invention and thus the location and orientation of holes within the network may also be precisely controlled. For example, holes may be produced at regular intervals within the network, e.g. spaces may be left between layers of gel objects. Alternatively, the location of holes may be randomly placed. The size of the holes is not particularly limited. For instance, a hole may be formed by omitting e.g. 1 to 100 gel objects from within a regular pattern, or by leaving a gap of e.g. 1 µm to 1 mm between gel objects.

The gel network may comprise multiple types of gel object. For instance, a gel network may comprise gel objects having the same chemical composition but having multiple different shapes, and/or multiple different sizes. Similarly, a gel network may comprise gel objects having multiple different chemical compositions, and/or shapes, and/or sizes. The number, location and orientation of these species may be controlled within the network. Thus the macroscale properties of the network may be controlled by controlling the composition, size and shape of the component gel objects. For example, gel objects containing different kinds of gut bacteria may be placed at different locations within the network. Alternatively, layers of different kinds of gel object each mimicking different layers of gut tissue may be positioned on top of one another to form a three-dimensional scaffold for a model of the intestine. Such a structure is illustrated in FIG. 6.

The gel network may comprise multiple orientations of the same type of gel object. For example, where the gel objects are elongated, e.g. rod-shaped gel objects, the network may comprise a region where the axes along the length of the gel objects therein form an angle (a) with a principal axis of the network, and another region where the axes along the length of the gel objects therein form an angle (b) with said principal axis of the network, wherein (a) is not the same as (b). An example of such a network is shown in FIG. 9 which contains gel microrods arranged in a herringbone pattern.

The gel network of the invention comprises gel objects as discussed in the section above. Thus the gel network of the invention may comprise gel objects having a range of shapes and sizes; comprising a range of gels and additional components such as biological cells, biological molecules or small molecules; and even having multiple regions of different compositions as discussed above. Preferably the gel network of the invention comprises gel objects in the shape of rods, where rods are as defined above. More preferably the gel network of the invention comprises Janus rods (also as defined above).

Gel objects within the gel network of the invention are joined to one another at a region of contact between the objects. By "a region of contact between the objects" is meant a location at which one gel object touches another. Typically each gel object within the network is joined to at least one other gel object within the network. For example, each gel object within the network may be joined to each object within the network with which it is in direct contact. Often at least some, and more typically all, of the gel objects in the network are joined to more than one other gel object in the network.

As used herein, the description of gel objects as being "joined" to one another typically means that the gel objects are gelled to one another. The gelling, or joining, does not necessarily occur throughout the entire region or regions of contact between adjacent gel objects. However, gelling can occur throughout the entire region or regions of contact between adjacent gel objects.

At a join between one gel object and another, the gel-forming agent in one gel object typically intermingles with and bonds (e.g. cross-links) to the gel-forming agent in the other to form a network of the gel-forming agent at the join. This network may for instance be a polymer network or a colloidal network, depending on the nature of the gel-forming agent.

The network at the join is expanded throughout its volume by the fluid component of the gel in the one gel object and the other gel object, to form a gel at the join. Thus the bonding between gel objects at a join is typically identical in character to the bonding within the gel in the bulk of the gel objects that are joined. Even if adjacent gel objects comprise different types of gel, the bonding between the gel objects may be identical in character to the bonding within the gel objects. For example, the bonding in two different hydrogels is characterised in the same way, by a combination of hydrogen bonding and interactive forces.

The join between adjacent gel objects may be referred to as a gel bond. This is because, at the join, the two gel objects gel to one another and hence a region of gel forms which adheres, i.e. bonds, the two gel objects together. A gel bond is therefore an adhesive bond, where the adhesive is gel. A gel bond may be formed by contacting incompletely-gelled gel objects, in order to facilitate (i) fusion of the gel objects together at a region of contact therebetween and (ii) further gelling within the fused region. The further gelling within the fused region forms gel which serves to bond (adhere) the gel objects together. In other words, the further gelling within the fused region forms a gel bond.

The region of gel which adheres the gel objects together, i.e. the gel bond, shares many physical characteristics with the bulk gel of the gel objects. At the join between gel objects, the surfaces of the individual gel objects cease to exist at the join and instead the gel objects integrate with one another. The gel objects are fused with and bonded (adhered) to one another at this point.

As a consequence of the full integration of neighbouring gel objects at a joining region, many of the physical characteristics of the gel at the join (referred to herein as the gel bond) between two adjacent gel objects are the same as those in the bulk. For instance, the viscosity of the gel bond is typically very similar to or the same as the viscosity of the gel in the bulk of the object. As will be appreciated, this is usually the case where the adjoining gel objects comprise, or consist of, the same type of gel.

The term "viscosity" as used herein refers to the absolute viscosity, also called the dynamic viscosity. The viscosity of a substance is a measure of its resistance to flow. The viscosity of a gel may be defined as the force required per unit area to move a plane of gel (having a unit area cross-section) relative to a parallel plane of gel while maintaining a unit distance between the planes of gel. Viscosity varies with temperature and hence viscosity is usually be quoted at a reference temperature. For the avoidance of doubt, unless stated otherwise the viscosity herein means the viscosity at room temperature, i.e. the viscosity at 25° C. Typically, the viscosity of gel at a join between adjacent gel objects is at least 50% of the viscosity of gel in the bulk of the gel objects, for example at least 75% or 90% of the viscosity of gel in the bulk of the gel objects. Again, it will be appreciated that this is usually the case where the joined gel objects comprise, or consist of, the same type of gel.

Where joined gel objects comprise different kinds of gel, the properties of gel in the joining region between the joined gel objects will not be identical to the properties of the gel forming either object, and will be determined by the interactions between the two or more kinds of gel particles in the joining region. However, the viscosity of gel at a join between gel objects comprising differing gels will typically be at least 50% of the average viscosity of the gel objects, for example at least 75% or 90% of the average viscosity of the gel objects.

Not all of the physical properties of the gel bond are the same as the physical properties of the bulk of the gel object. The gel objects join at a joining region but remain distinct objects; they retain the shape they had prior to contacting and joining to or gelling to one another, except at the join. Hence the join between gel objects comprises gel which is substantially thinner than the thickness of the gel objects themselves. Typically, the thickness of gel at the join is smaller than the diameter of the smallest gel object falling the join. Typically, the thickness of gel at the join may be less than 50%, e.g. less than 25%, of the size of the smallest dimension of any gel object forming the join. The "thickness of gel at the join" is taken to mean the smallest dimension of the gel polygon in the plane of the join. For example, where two rods are placed parallel to one another and form a join in the region of contact which forms along their length, the thickness of gel at the join is the thickness of gel in the plane which sits in the plane of the join between the two rods and is perpendicular to the line linking their centres.

Some physical properties of the gel bond may differ from the properties of the bulk gel objects, because the volume of gel at the join between gel objects is smaller than the volume of gel in the bulk, as discussed above. Thus properties which have a dependence on the volume of the material will differ between the gel at the join, or gel bond, and in the bulk. For instance, when the gel network is subjected to a mechanical force, the small amount of material in the gel bond between adjacent gel objects will typically deform more easily than the gel objects themselves.

As will be appreciated from the discussion of the strength of the join between gel objects in the gel network of the invention, the joining of the gel objects in the network can lead to a network which is remarkably strong. One advantage of the strength of the network is that it can support surprisingly large networks of up to several centimetres in each dimension. However, that is not the only advantage of joining the gel objects. An additional advantage is that joining the gel objects to one another fixes their orientation within the network. It is therefore possible to create a network with directionally-dependent properties, that is, properties which vary with the axis of the network along which they are measured.

Within the gel network, each gel object is typically joined to at least one other gel object. However, that is not to say that the joining of gel objects is uniform throughout the network. For instance, the gel objects may be joined in a layer-like fashion, such that each object within a layer of the gel network is joined to at least one other object within that layer of the gel network, but there are no joins between gel objects in different layers. Alternatively, each gel object may be joined to at least half of its neighbours within the network, or all of its neighbours within the network, to form a strong and rigid network. Other examples of patterns of joining within a gel network include joining individual objects into long chains, or joining gel objects at the end of a network to form a rolled-up network or tube.

The extent to which neighbouring gel objects within the gel network are joined affects the strength of the network. As mentioned above, a network in which all objects are joined to a substantial proportion or indeed all of their neighbours will be strong and rigid. By contrast, a network in which gel objects are not joined to all of their neighbours may be susceptible to deformation. For instance, a network comprising layers of joined gel objects but having no joins linking one layer to another may allow the layers to move past one another, but not through one another. Such a network may therefore be susceptible to deformation in the plane of the layers but not perpendicular to the plane of the layers. In another example, a network comprising chains of joined gel objects may be twisted or compressed, as each chain or strand can bend at each join to accommodate folding or twisting of the chain. However, the joins are not easily broken and a network comprising such chains could not be pulled apart easily. Such a network is therefore strong under tension but weak under compression, and moreover may provide a suitable model of fibrous tissue or muscle.

It is apparent from this discussion that control of the number and location of joins between gel objects within a network allows the physical properties of the network to be controlled. The number and location of joins between gel objects in the network may be varied to control the network's strength and susceptibility to deformation in three dimensions.

The process of the invention allows the creation of a network of gel objects wherein the location and orientation of each gel object within the network can be precisely controlled. The network of gel objects may therefore be carefully designed, in three dimensions, and hence its properties may be adapted to fit specific needs. A range of situations in which it is advantageous to have the ability to locate species precisely within the network are discussed below.

In some embodiments, the gel network may contain differing chemicals which are intended to be released from the network at different times. It is therefore advantageous to place gel objects containing chemicals which are to be released slowly in the centre of the network, and gel objects containing chemicals which are to be released slowly at the edge of the network.

In another embodiment, the network may be designed to deform in a particular manner on exposure to an external stimulus such as heat or the presence of liquid. Gel objects having differing responses to such stimuli may be arranged in order to control the pattern of deformation on exposure to such a stimulus. For instance, a network analogous to a bimetallic strip may be formed by arranging a layer of gel objects which swell in the presence of hot water above a layer of gel objects which do not swell in hot water. When the object is placed in hot water, the expansion of one layer but not with other will cause the object to curl up.

One of the most important advantages of the ability to precisely control the location and orientation of gel objects within a gel network is that enables the building of complex structures. In particular, it enables the creation of structures which mimic living tissue, typically human tissue or animal tissue, for example human organs. Such complex structures may comprise not only a gel network according to the invention but also other features such as a solid support.

The gel network may comprise materials in addition to the gel objects. For example, the network of joined gel objects may further comprise an extracellular matrix material. The extracellular matrix material may, for instance, be collagen, Matrigel, lamin or fibronectin.

The gel network may comprise a support material. By "support material" is meant a material which covers a part or all of the gel network. For example, the support material may be present on one face of the network, or the gel network may be wholly encased in a support material. In another embodiment, the gel network may have a support material inside the network, such that the network is built around the support material.

The nature of the support material is not particularly limited. The support material may be a rigid material or a deformable material, for example a thermoresponsive material. A thermoresponsive material is one which changes shape as its temperature is varied. The support material may, for instance, comprise a polymer. For example, the coating material may be a gel, e.g. a thermoresponsive gel. In one embodiment, the support material is poly(N-isopropylacrylamide) (PNIPAM).

The support material may have differing properties, e.g. different thermal properties, from the gel network in the absence of the support material. In consequence, a composite object comprising a support material and a gel network may have properties (e.g. thermal properties) which differ from the thermal properties of the gel network in the absence of the support material. An example of such behaviour is seen in FIG. 2, wherein a network of gelatin-methacrylate objects encased in PNIPAM is observed to deform in hot water and cold water. The reason for this deformation is that PNIPAM is a thermoresponsive material, and its deformation is guided by the orientation of the gel objects within it. Thus, in some embodiments, the invention relates to a gel network comprising a support material (for example a thermoresponsive support material) wherein the temperature-controlled deformation of the support material is controlled by the gel network, for example by the orientation of the gel objects within the gel network.

The gel network of the invention may be put to a variety of uses, including, for instance: as a model of biological tissue; as an in vivo implant, for example in drug delivery or in damaged tissue; in an optical device; in an electronic device; and as a novel material.

The Process of the Invention

The invention provides a process for producing a gel network, which gel network comprises a plurality of joined gel objects, which process comprises:

forming a plurality of gel objects in one or more microfluidic channels;

dispensing the gel objects from the one or more microfluidic channels into a region for producing the network; and contacting each gel object with at least one other gel object in said region (for producing the network) to join each gel object to at least one other gel object at a region of contact between the gel objects.

The process may comprise forming at least 10 gel objects in one or more microfluidic channels, i.e. the plurality of gel objects is at least 10 gel objects. The process typically comprises forming at least 50 gel objects in one or more microfluidic channels, i.e. the plurality of gel objects is at least 50 gel objects. The gel network produced by the process of the invention typically therefore comprises at least 50 joined gel objects. The process may for instance comprise forming at least 100 gel objects in the one or more microfluidic channels, i.e. the plurality of gel objects may be at least 100 gel objects. The gel network produced by the process of the invention may therefore comprise at least 100 joined gel objects. In some embodiments, the process comprises forming at least 1,000 gel objects in the one or more microfluidic channels, i.e. the plurality of gel objects is at least 1,000 gel objects. The process may for instance comprise forming at least 100,000 gel objects in the one or more microfluidic channels, for instance it may comprise forming at least 500,000 gel objects in the one or more microfluidic channels, i.e. the plurality of gel objects may be at least 100,000 gel objects, or for instance at least 500,000 gel objects. The gel network produced by the process of the invention may therefore comprise at least 1,000 joined gel objects, for instance at least 100,000 joined gel objects, such as for example at least 500,000 joined gel objects. The plurality of gel objects may for instance be from 50 to 1,000,000 gel objects, for example from 100 to 500,000 gel objects or from 1,000 to 100,000 gel objects. The gel network produced by the process of the invention may therefore comprise from 50 to 1,000,000 joined gel objects, for example from 100 to 500,000 joined gel objects or from 1,000 to 100,000 joined gel objects.

As will be understood by the skilled person, not all of the gel objects in the plurality need be formed in one particular microfluidic channel. The process may comprise forming the plurality of gel objects in more than one microfluidic channel, for instance in two, three or more than three microfluidic channels.

Thus, the process may comprise forming said plurality of gel objects in a first microfluidic channel and in one or more further microfluidic channels. In such embodiments, more than one gel object will still generally be formed in each of the microfluidic channels employed in the process.

Thus, in such embodiments, the process will generally comprise forming a first plurality of gel objects in the first microfluidic channel, and forming a further plurality of gel objects in each further microfluidic channel employed. For example, the process may comprise forming a first plurality of gel objects in a first microfluidic channel, and forming a second plurality of gel objects in a second microfluidic channel. The process may further comprise forming a third plurality of gel objects in a third microfluidic channel.

In any case, the process typically comprises: forming a first gel object and a second gel object in a microfluidic channel; dispensing the first and second gel objects from the microfluidic channel into a region for producing the network; and contacting the first gel object with the second gel object in said region to join the first gel object to the second gel object at a region of contact between the first and second gel objects. The process may further comprise forming one or more further gel objects in the microfluidic channel; dispensing the one or more further gel objects from the microfluidic channel into the region for producing the network; and contacting each of the one or more further gel objects with the first gel object, the second gel object, or a further gel object in said region, to join each further gel object to at least one other gel object at a region of contact between the gel objects.

Typically, in such embodiments, the first, second and further gel objects are at least 50 gel objects in total. The gel network produced by the process of the invention typically therefore comprises at least 50 joined gel objects. The first, second and further gel objects may for instance be at least 100 gel objects in total. The gel network produced by the process of the invention may therefore comprise at least 100 joined gel objects. In some embodiments, the first, second and further gel objects are at least 1,000 gel objects in total. The first, second and further gel objects may for instance total at least 100,000 gel objects, or for instance at least 500,000 gel objects. The gel network produced by the process of the invention may therefore comprise at least 1,000 joined gel objects, for instance at least 100,000 joined gel objects, such as for example at least 500,000 joined gel objects. The first, second and further gel objects may for instance total from 50 to 1,000,000 gel objects, for example from 100 to 500,000 gel objects or from 1,000 to 100,000 gel objects. The gel network produced by the process of the invention may therefore comprise from 50 to 1,000,000 joined gel objects, for example from 100 to 500,000 joined gel objects or from 1,000 to 100,000 joined gel objects.

Forming the Gel Object

According to the process of the invention, gel objects are formed in one or more microfluidic channels. The formation of the gel object involves the gelation of a flowable medium, referred to herein as a "gel precursor material", which comprises a gel-forming agent and a fluid. The fluid is typically a liquid. The natures of the gel-forming agent and the fluid in the gel precursor material described further hereinbefore. The gel objects formed by the process of the invention are also as described above.

Typically, the gel precursor material comprising the gel-forming agent and the fluid is capable of undergoing a phase transformation to form a gel when the temperature of the gel precursor material is reduced below a certain temperature. That is, the gel precursor material comprising gel particles is typically capable of undergoing a sol-gel transition at the sol-gel transition temperature (the temperature at which the transition from flowable, gel precursor material to gel occurs). The sol-gel transition is typically a liquid to solid phase transformation when the gel precursor material is cooled from above the sol-gel transition temperature to below the sol-gel transition temperature. For instance, when the fluid in the gel precursor material is water and the gel-forming agent in the gel precursor material is a hydrogel compound, such that the gel precursor material is an aqueous medium comprising a hydrogel compound, the aqueous medium will gel to form a hydrogel when the temperature of the aqueous medium is reduced below a certain temperature (which will be the gelling temperature of the hydrogel compound in that aqueous medium).

Where the formation of gel objects occurs due to a temperature-controlled sol-gel transition, the temperature of the flowable gel precursor material, and the gel object, may be controlled to determine the extent of gelation.

Typically, in the process of the invention, a reservoir of gel precursor material (which has yet to be added to the microfluidic channel) is maintained at a temperature above the sol-gel transition temperature. This may, for instance be, a temperature of about, or above, room temperature, for instance it may be a temperature which is equal to or greater than 25° C., for instance a temperature which is equal to or greater than 30° C., or for example a temperature which is equal to or greater than 35° C. The temperature at which the reservoir of gel precursor material is maintained may for instance be from 25° C. to 70° C., for instance from 30° C. to 60° C., for example from 35° C. to 50° C. Thus the gel precursor material typically has not gelled before it enters the microfluidic channel. However, it is possible that solid gel objects may be placed into the microfluidic channel and then encapsulated in gel precursor material to form a larger gel object within the microfluidic channel. If solid gel objects are placed in the microfluidic channel and subsequently encapsulated in gel, the solid gel object placed in the channel typically either is solid at the temperature of the microfluidic channel, or has been previously irreversibly solidified, for instance by photoinitiated cross-linking, thermally-initiated cross-linking, or enzyme-initiated cross-linking.

In some embodiments of the invention, a reservoir of gel precursor material (which has yet to be added to the microfluidic channel) is maintained at a temperature below the sol-gel transition temperature. Typically, in these embodiments, the gel precursor material is one which is flowable below the sol-gel transition temperature and which gels at a higher temperature. This type of gel material, which undergoes gelling upon heating, may be referred to as a thermos-gelling material. An example of this type of gel is Pluronic F127 (see Tissue Eng 2005, 11, 974-983). In these embodiments, the reservoir of thermos-gelling material is maintained for instance at from 1° C. to 30° C., for instance from 5° C. to 25° C., for example from 10° C. to 20° C. Thus the gel precursor material typically has not gelled before it enters the microfluidic channel. However, it is possible that solid gel objects may be placed into the microfluidic channel and then encapsulated in gel precursor material to form a larger gel object within the microfluidic channel. If solid gel objects are placed in the microfluidic channel and subsequently encapsulated in gel, the solid gel object placed in the channel typically either is solid at the temperature of the microfluidic channel, or has been previously solidified, for instance by photoinitiated cross-linking.

In some embodiments of the invention, the gel precursor material may undergo a sol-gel transition (typically a liquid to solid phase transformation) when the gel precursor material is exposed to a chelating agent. An example of a gel precursor material which undergoes a sol-gel transition when exposed to a chelating agent is an alginate gel. In the case of an alginate gel, a suitable chelating agent is a divalent metal ion, for instance an alkaline earth metal dication, for example a calcium ion.

A gel object is typically at least partially gelled when it is dispensed from a microfluidic channel. Preferably, though, the gel object is incompletely gelled when it is dispensed from the microfluidic channel. Partial gelling (that is, partial solidification) therefore usually occurs between the gel precursor material entering the microfluidic channel and the gel object being dispensed from the microfluidic channel.

One advantage of ensuring that gel objects are formed in a microfluidic channel is that the gel objects are stable when they exit the microfluidic channel. By "stable" it is meant that the gel objects maintain their shape after they are dispensed from the microfluidic channel. This aspect of the process of the invention is advantageous as it removes the need for surfactants to stabilise the gel objects in the region in which the gel network is formed. Also, as mentioned above, the gel objects that are formed in the one or more microfluidic channels are typically incompletely gelled, which has the advantage that, when the gel objects are subsequently contacted with one another in the region for producing the network, the gel objects fuse together at the regions of contact and further gelling occurs at those regions, to form a gel bond at each of those regions which joins the gel objects together.

If the gel precursor material is capable of undergoing a temperature-controlled sol-gel transformation, the gelling of the gel precursor material in the microfluidic channel, to form the gel objects in the microfluidic channel, may be achieved by controlling the temperature of the microfluidic channel.

Typically, therefore, in the process of the invention, a part of the microfluidic channel (often a part of the microfluidic channel adjacent to the region where the gel object is dispensed) is held at a particular temperature, which is typically a temperature that is below the sol-gel transition temperature of the gel. The particular temperature may, for instance be, a temperature of below room temperature, for instance it may be a temperature of less than 25° C. It may for instance be a temperature equal to or below 20° C., for instance a temperature of from greater than 0° C. to 20° C., such as, for instance, a temperature of from 1° C. to 15° C., or for example a temperature of from 4° C. to 12° C. However, particularly where the gel precursor material is a thermos-gelling material, said part of the microfluidic channel may be held at a temperature that is above the sol-gel transition temperature of the gel. The extent of gelling of the gel object within the microfluidic channel may be controlled by adjusting the temperature of the microfluidic channel, and/or the length of the microfluidic channel, and/or the flow rate of the flowable medium comprising gel particles through the microfluidic channel.

In some embodiments of the invention, the fluid in the gel precursor material is water and the gel-forming agent in the gel precursor material is a hydrogel compound such that the gel precursor material is an aqueous solution comprising a hydrogel compound. In such embodiments, the gel precursor material may have a sol-gel transition temperature (which may for example be a particular temperature within the range of from 25° C. to 35° C.) and so a reservoir of gel precursor material (which has yet to be added to the microfluidic channel) is typically maintained above that temperature, while the microfluidic channel in which the gel objects are formed is maintained below that temperature.

The process of the invention, and in particular the step of forming the gel objects in one or more microfluidic channels, may therefore comprise:
(a) maintaining a gel precursor material (which may be as further defined herein) at a first temperature;
(b) introducing the gel precursor material into the one or more microfluidic channels; and
(c) maintaining the one or more microfluidic channels at a second temperature, which second temperature is different from the first temperature.

The second temperature is usually lower than (i.e. less than) the first temperature. However, as discussed above, if a thermos-gelling gel precursor material is employed, which undergoes gelling upon heating, the second temperature will usually be higher than (i.e. greater than) the first temperature.

The purpose of maintaining the gel precursor material at the first temperature is to prevent the gel precursor material from gelling and thereby keep it in a flowable (typically liquid) state. The purpose of maintaining the one or more one or more microfluidic channels at a second temperature is to initiate gelling of the gel precursor material to form the gel objects.

As mentioned above, the second temperature is usually lower than (i.e. less than) the first temperature. Typically, the first temperature is about, or above, room temperature. For instance the first temperature may be equal to or greater than 25° C., for example equal to or greater than 30° C., or equal to or greater than 35° C. The first temperature may for instance be from 25° C. to 70° C., for instance from 30° C. to 60° C., for example from 35° C. to 50° C.

The second temperature, at which the microfluidic channel or channels (in which the gel objects are formed) is maintained is typically below room temperature. For instance it may be a temperature of less than 25° C., or for example a temperature equal to or below 20° C. The second temperature may for instance be a temperature of from greater than 0° C. to 20° C., such as, for instance, a temperature of from 1° C. to 20° C., from 2° C. to 15° C. or for example from 4° C. to 12° C.

For instance, the first temperature may be equal to or greater than room temperature and the second temperature may be less than room temperature. The first temperature may for instance be equal to or greater than 25° C. and the second temperature may be less than 25° C. The first temperature may for instance be equal to or greater than 30° C. and the second temperature may be equal to or below 20° C. Often, for instance, the first temperature is equal to or greater than 35° C. and the second temperature is equal to or below 20° C. The first temperature is usually less than 90° C. and the second temperature is typically greater than 0° C.

The first temperature may for instance be from 25° C. to 70° C. and the second temperature may be from 1° C. to 20° C. Often, for instance, the first temperature is from 30° C. to 60° C. and the second temperature is from 2° C. to 15° C. The first temperature may for instance be from 35° C. to 50° C. and the second temperature may be from 4° C. to 12° C.

The first temperature may for instance be above 30° C., for instance from 35° C. to 55° C. and the second temperature may be below 30° C., for instance from 2° C. to 25° C., for example 8° C.

In some embodiments, the second temperature is higher than (i.e. more than) the first temperature. In particular, the second temperature is higher than the first temperature where the gel precursor material is a thermos-gelling material (that is, a material which undergoes gelling when heated). Such gels are maintained in a flowable state at low temperature and become less flowable on heating.

Typically, the first temperature is about, or below, room temperature. For instance the first temperature may be equal to or less than 30° C., for example equal to or less than 25° C., or equal to or less than 20° C. The first temperature may for instance be from 1° C. to 30° C., for instance from 5° C. to 25° C., for example from 10° C. to 20° C.

The second temperature, at which the microfluidic channel or channels (in which the gel objects are formed) is maintained is typically above room temperature. For instance it may be a temperature of more than 30° C., or for example a temperature equal to or above 40° C. or 50° C. The second temperature may for instance be a temperature of from 30° C. to 70° C., such as, for instance, a temperature of from 35° C. to 60° C., for example from 40° C. to 50° C.

For instance, the first temperature may be less than room temperature and the second temperature may be more than or equal to room temperature. The first temperature may for instance be less than 30° C. and the second temperature may be equal to or more than 30° C. The first temperature may for instance be equal to or less than 25° C. and the second temperature may be equal to or above 35° C. Often, for instance, the first temperature is equal to or less than 20° C. and the second temperature is equal to or above 40° C. The first temperature is usually greater than 0° C. and the second temperature is typically less than 90° C.

The first temperature may for instance be from 1° C. to 25° C. and the second temperature may be from 30° C. to 70° C. Often, for instance, the first temperature is from 2° C. to 15° C. and the second temperature is from 35° C. to 60° C. The first temperature may for instance be from 4° C. to 12° C. and the second temperature may be from 40° C. to 50° C.

The first temperature may for instance be below 30° C., for instance from 5° C. to 20° C. and the second temperature may be above 30° C., for instance from 35° C. to 50° C., for example 40° C.

The temperature of the microfluidic channel, the flow rate of the gel precursor material and the length of the microfluidic channel may be adjusted to ensure that the gel precursor material undergoes a sol-gel transition when flowing towards the outlet of the microfluidic channel.

For example, in some embodiments of the invention, the gel precursor material is an aqueous solution comprising gelatin. In this embodiment, the gel precursor material comprising gelatin has a sol-gel transition temperature of about 30° C., and so the reservoir of gel precursor material comprising gelatin is typically maintained above 30° C., for instance at a temperature of from 35° C. to 55° C. while the microfluidic channel in which the gelatin gel objects are formed is maintained at a temperature below 30° C., for instance at a temperature of from 2° C. to 25° C., for example 8° C. The temperature of the microfluidic channel, the flow rate of the gel precursor material comprising gelatin and the length of the microfluidic channel are adjusted to ensure that the gelatin undergoes a sol-gel transition when flowing towards the outlet of the microfluidic channel.

However, the formation of gel objects may occur other than by a temperature-controlled sol-gel transition. The gel precursor material may be induced to undergo gelling in the microfluidic channel to form a gel object by any suitable means. For instance, the gelling process may comprise a covalent cross-linking process which may be initiated, for example, by incident light (also called photoinitiation) or by thermal initiation (that is, by heating). An example of a gel which may be induced to undergo a sol-gel transition by heating is Matrigel.

Thus, in some embodiments, the process of the invention, and in particular the step of forming the gel objects in one or more microfluidic channels, may comprise:
(a) maintaining a gel precursor material (which may be as further defined herein) at a first temperature;
(b) introducing the gel precursor material into the one or more one or more microfluidic channels; and
(c) maintaining the one or more one or more microfluidic channels at a second temperature, which second temperature is greater than the first temperature.

Also, in some embodiments, the process of the invention, and in particular the step of forming the gel objects in one or more microfluidic channels, may comprise:
(a) introducing a gel precursor material (which may be as further defined herein) into the one or more one or more microfluidic channels; and
(b) irradiating the one or more one or more microfluidic channels with light suitable for initiating cross-linking within the gel precursor material. The light suitable for initiating cross-linking within the gel precursor material may, for instance, be ultraviolet light or visible light.

For example, blue light can be used to crosslink polymers in combination with a riboflavin initiator.

If the gel precursor material is capable of undergoing a sol-gel transformation induced by contact with a chelating agent, the gelling of the gel precursor material in the microfluidic channel, to form the gel objects in the microfluidic channel, may be achieved by controlling the addition of the chelating agent to the gel precursor material. Typically, the chelating agent is added to the gel precursor material in the microfluidic channel. For example, a chelating agent may be added to the microfluidic channel with a gel precursor material. However, a chelating agent may also be added to droplets of gel precursor material within a microfluidic tube. The extent and rate of gelling of the gel precursor material in the microfluidic channel may be controlled by controlling the amount and/or the concentration of the chelating agent which is added to the gel precursor material. The extent and rate of gelling may be controlled by controlling the time at which a chelating agent is added to the gel precursor material. For example, the degree of gelling in a gel object may be increased by increasing the delay between the time at which a gel precursor material is contacted with a chelating agent and the time at which the gel object thus formed is dispensed.

Thus, in some embodiments, the process of the invention, and in particular the step of forming the gel objects in one or more microfluidic channels, may comprise introducing a chelating agent to the or each microfluidic channel.

In some embodiments, the process of the invention, and in particular the step of forming the gel objects in one or more microfluidic channels, may comprise
(a) introducing a gel precursor material into a microfluidic channel at a gel precursor inlet;
(b) introducing a chelating agent into said microfluidic channel at a chelating agent inlet; and
(c) allowing the gel precursor material to mix with the chelating agent.

The gel precursor inlet and the chelating agent inlet may or may not be at the same position relative to the microfluidic tube. For example, said inlets may introduce gel precursor material and chelating agent into the same place within the microfluidic tube. In some embodiments, the chelating agent inlet is downstream from the gel precursor inlet in the microfluidic tube. In these embodiments, the chelating agent is introduced to gel precursor, for example droplets of gel precursor, already within the microfluidic tube. In some embodiments, the chelating agent inlet is upstream from the gel precursor inlet in the microfluidic tube. In these embodiments, the gel precursor is introduced to chelating agent, for example droplets of chelating agent, already within the microfluidic tube.

The addition of a chelating agent to a microfluidic tube either with a gel precursor or after a gel precursor is illustrated in FIG. 18. In this Figure, the gel precursor material is an alginate reservoir and the chelation agent is a reservoir of calcium ions. The alginate solution, calcium ions and oil are injected into a microfluidic tube.

Figure 18A:
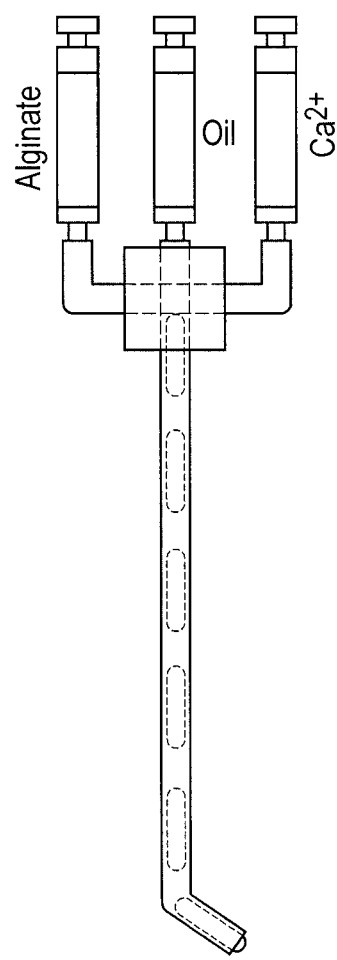

FIG. 18a illustrates an embodiment wherein these three substances are injected into the same place within the microfluidic tube, at a three-way inlet or port. Portions of alginate mixed with chelating agent (calcium ions), interspersed with oil plugs, form in the microfluidic tube. The gelling process occurs as the alginate approaches the end of the tube, and partially or fully gelled objects are dispensed.

Figure 18B:
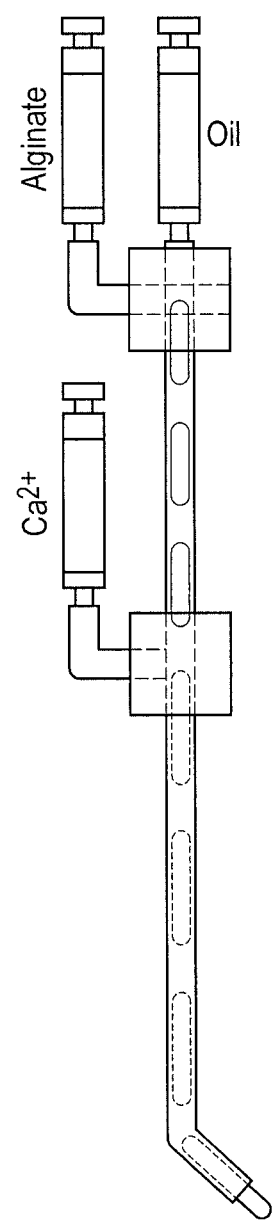

FIG. 18b illustrates an embodiment wherein the gel precursor material (alginate solution) and oil are injected into a microfluidic tube via a two-way inlet or port. Portions of gel precursor (alginate) are formed, interspersed with oil plugs. The portions of gel precursor material pass a further one-way inlet (port) downstream. The chelating agent (calcium ions) are injected here and mix with the alginate, causing gelling.

In some embodiments of the invention, regardless of the means by which a gel precursor material is induced to undergo gelling in a microfluidic channel, the gelling is incomplete when the gel object exits the microfluidic channel. Typically, the gelling process is sufficiently advanced that the gel object is stable in the region in which the network is formed (that is, it maintains its shape). However, the cross-linking process may be incomplete when a gel object is dispensed from the microfluidic channel, so that typically gel objects are able to undergo further cross-linking (that is, further gelling) after they have been dispensed from the microfluidic channel.

Gel objects which are incompletely gelled when they exit the microfluidic channel are capable of undergoing further gelling not only internally within the gel object but also externally, to adjacent gel objects, at a region of contact between the gel objects. The gel objects which are incompletely gelled can therefore gel to one another to form a region of gel between the gel objects which is referred to as a gel bond.

In the process of the invention, forming the plurality of gel objects in one or more microfluidic channels typically comprises: forming a plurality of incompletely-gelled gel objects in the one or more microfluidic channels;
dispensing the gel objects from the one or more microfluidic channels into the region for producing the network usually comprises: dispensing the incompletely-gelled gel objects from the one or more microfluidic channels into the region for producing the network; and
contacting each gel object with at least one other gel object in said region for producing the network usually comprises: contacting each incompletely-gelled gel object with at least one other incompletely-gelled gel object in said region for producing the network, to join each gel object to at least one other gel object at a region of contact between the gel objects.

Typically, contacting each incompletely-gelled gel object with at least one other incompletely-gelled gel object causes each incompletely-gelled gel object to fuse with at least one other incompletely-gelled gel object at a region of contact between the gel objects wherein gelling occurs at the region of fusion to form a gel bond between the gel objects.

Thus, typically, the gel objects are incompletely gelled when they are contacted with one another and the process comprises contacting each gel object with at least one other gel object in said region for producing the network to form a gel bond between each gel object and at least one other gel object at a region of contact between the gel objects.

Usually, in the process of the invention, joining each gel object to at least one other gel object comprises forming a gel bond between each gel object and at least one other gel object at said region of contact between the gel objects.

The gel network may be subjected to further process steps after the dispensing of gel objects. For example, once sufficient gelling between gel objects within a gel network is deemed to have occurred, the gel network may be subjected to a further process step to complete the gelling (that is, the solidification) of the gel objects. The nature of such a step is discussed in more detail below.

The Microfluidic Channel Size, Cross-Section

According to the process of the invention, gel objects are formed in a microfluidic channel. By "microfluidic channel" is typically meant a channel whose internal diameter is from 1 µm to 2000 µm, for instance from 5 µm to 2000 µm, or from 10 µm to 2000 µm, or, say, from 10 µm to 1000 µm. For example, the internal diameter of a microfluidic channel may be from 10 µm to 500 µm, e.g. from 20 µm to 250 µm, for instance from 25 µm to 150 µm.

The shape of the or each microfluidic channel is not particularly limited. A microfluidic channel may have a circular cross-section, in which case the diameter of the channel (as discussed in the preceding paragraph) refers to the diameter of the circular cross section. It may alternatively however have a cross-section which is in the shape of any polygon, for example a square, a rectangle, a triangle, a pentagon, a hexagon and so on. Where the cross-section of a microfluidic channel is not circular, the diameter of the channel (as discussed in the preceding paragraph) refers to the largest distance from one edge of the cross section to another edge of the cross section. Thus, for example, when the cross section of a microfluidic channel is square, the diameter refers to the distance from one corner of the square to the opposite corner of the square (passing through the centre of the square). Usually the or each microfluidic channel employed in the process of the invention has a substantially circular cross-section. Often, the or each microfluidic channel has a circular cross-section.

Each microfluidic channel employed in the process of the invention comprises an inlet. An inlet enables a flowable gel precursor material to enter the microfluidic channel. An inlet also enables a medium which does not mix with the gel or with the gel precursor material to enter the microfluidic channel. The medium which does not mix with the gel or the gel precursor material may be referred to herein as "immiscible medium". The immiscible medium may form alternate plugs with the gel in the or each microfluidic channel.

Each microfluidic channel typically comprises an inlet that allows both the gel precursor material and the immiscible medium into the microfluidic channel. Such an inlet may be a two-way inlet, meaning that the inlet allows two substances to enter the tube. However, the microfluidic channel may also comprise a multiway inlet, e.g. a three-way inlet or a four-way inlet, which allows multiple substances into the microfluidic channel. For example, a three-way inlet allows three substances into the microfluidic channel and a four-way inlet allows four substances into the microfluidic channel. Substances other than the immiscible material that are added to the microfluidic channel typically mix with the gel precursor material.

The immiscible medium is typically a flowable medium, such as a liquid. Typically the immiscible medium is a liquid which is immiscible with the fluid component of the gel-precursor material. For instance, when the gel precursor material is a hydrophilic medium (e.g. an aqueous medium) and therefore the fluid component of the gel precursor material is hydrophilic or is, or comprises, water, then the immiscible medium will be a hydrophobic medium (e.g. an oil-based medium, a liquid composition comprising oil or a non-polar organic solvent). Suitable oils which may be employed as the immiscible material include hydrocarbon oils. $C_{10}$-$C_{20}$ alkanes may for instance be employed. Tetradecane is often employed. The immiscible material is typically an oil. The oil may be a single, pure, compound, or the oil may comprise a mixture of two or more compounds. The oil may for instance comprise silicone oil (for instance poly phenyl methyl siloxane). The oil may consist of a single silicone oil, for instance poly phenyl methyl siloxane. Alternatively, the oil may comprise a mixture of two or more different silicone oils. Any suitable silicone oil may be used. For instance, the oil may comprise silicon oil DC200 (a polymer comprising monomer units of —O—Si(CH$_3$)$_2$—), poly(dimethylsiloxane) (PDMS), hydroxy terminated, or PDMS 200.

Additionally or alternatively, the oil may comprise a hydrocarbon. When the oil comprises a hydrocarbon it may comprise a single hydrocarbon compound, or a mixture of two or more hydrocarbons. A hydrocarbon oil is typically employed, for instance a $C_{10}$-$C_{20}$ alkane. Tetradecane is often employed. Similarly, when the gel precursor material is a hydrophobic medium (for instance when the fluid component of the gel precursor material is an oil), the immiscible medium will be a hydrophilic medium (e.g. an aqueous medium, for instance water or an aqueous solution).

The or each microfluidic channel may comprise multiple inlets. The inlets may be distributed along the or each microfluidic channel. Typically, one or more additional inlets are present in the or each microfluidic channel downstream from an inlet which allows both the gel precursor material and an immiscible medium. These additional inlets are typically one-way inlets (which allow one substance to enter the microfluidic channel). However, they may alternatively be two-way inlets, three-way inlets, four-way inlets and so on. Inlets which add substances downstream from the first inlet typically either add substances which mix with the portions of gel precursor material, or add additional portions of a gel precursor material.

The inlets may be ports.

The or each microfluidic channel further comprises an outlet. The outlet may be defined as an opening in the microfluidic channel which is typically downstream from an inlet in the microfluidic channel. The shape and size of the outlet is not particularly limited; however, it is typically large enough to allow a gel object to exit the microfluidic channel. In some embodiments, the outlet comprises an open end of the microfluidic channel. In some embodiments, the outlet comprises a nozzle.

The microfluidic channel may be temperature-controlled. For example, the microfluidic channel may be placed in a refrigerated environment or in a heated environment.

In some embodiments, a microfluidic channel is a tube, for example a polytetrafluoroethylene (PTFE) tube.

Flow Control

The flow of substances into the microfluidic channel, whether via a two-way inlet, a multiway inlet or via multiple inlets, is controlled by a flow control device. The flow control device typically comprises a computer programme running on a suitable controller such as a computer, optionally in combination with a syringe. The rate at which each substance enters the microfluidic channel may be controlled. This is referred to as the flow rate, and may also be referred to as the injection rate or the input rate. The flow rate may be measured as a function of volume per unit time. The time at which each substance enters the microfluidic channel may be controlled.

In some embodiments, the rate at which both the gel precursor material and the immiscible medium (that is immiscible with the gel and is immiscible with the gel precursor material) are introduced into the microfluidic channel may be controlled in order to ensure that the phases do not mix or emulsify but rather form alternate droplets within the channel. If additional substances, for instance substances which mix with the gel precursor material, are introduced at the same inlet as the gel precursor material then the flow rate of those additional substances is typically also controlled.

In some embodiments, the flow rate of the gel precursor material into the microfluidic channel is chosen to control the size of the portions of said medium within the microfluidic channel, and hence to control the size of the gel objects.

Similarly, in some embodiments, the flow rate of the immiscible medium is chosen in order to control the size of the plugs of immiscible medium between gel objects in the or each microfluidic tube. This is a useful aspect of the invention because control of the size of the plugs (formed by the immiscible medium) between gel objects allows control of the time period that elapses between each gel object being dispensed. In some embodiments of the invention, it is important to allow sufficient time to elapse between dispensing each object in order to allow time for the relative motion of the microfluidic channel and the region in which the gel network of the invention is formed between each dispensing step. Controlling the amount of the time that elapses between dispensing steps may be used to control the distance at which the gel objects are dispensed apart from one another, and therefore to control the relative positioning of the gel objects.

In some embodiments of the invention, a substance or substances are introduced into a microfluidic channel which mix with the gel precursor material. These substances may be introduced via same inlet as the gel precursor material or via a different inlet. Regardless of where the additional substance(s) are introduced into a microfluidic channel, their flow rate into the microfluidic channel may be controlled, for example by a flow control device, in order to control the concentration of the additional substance(s) within the gel objects and hence within the gel network.

In some embodiments of the invention, additional substances are introduced into the microfluidic channel which form part of the gel object but which do not become evenly distributed throughout the gel object. This results in the formation of gel objects whose composition is not uniform throughout the object, for instance gel objects comprising regions of differing compositions. Such gel objects may be as further defined hereinbefore. Typically, such objects are Janus rods. Janus rods are defined and further described hereinbefore.

In some embodiments, gel objects whose composition is not uniform are created by introducing a portion of a second gel precursor material adjacent to a portion of the gel precursor material (which may be termed the "first gel precursor material") within the or each microfluidic channel, wherein the composition of the first and second gel precursor materials are different.

The first gel precursor material may for instance comprise a material, for instance a compound, which is absent from the second gel precursor material, and/or the second gel precursor material may comprise a material, for instance a compound, which is absent from the first gel precursor material. Additionally or alternatively, the first and second gel precursor materials may both comprise a particular material, for instance a particular compound, but at different concentrations. For instance, the concentration of the material (e.g. compound), in the first gel precursor material may be at least twice the concentration of the material (e.g. compound) in the second gel precursor material. The concentration of the material (e.g. compound), in the first gel precursor material may for instance be at least ten times, for example at least 100 times, at least 1,000 times, or at least 1,000,000 times, the concentration of the material (e.g. compound) in the second gel precursor material.

The material (or compound) in question may for instance be a particular gel-forming agent, biological cells, a particular type of biological cell, or a particular small molecule compound. The material may for instance be a therapeutic agent, diagnostic agent, biological compound (for instance a protein or enzyme, for instance a membrane protein, e.g. a membrane pore protein) or biological cells (e.g. mammalian cells, for example mammalian cells selected from human embryonic kidney (HEK) cells, osteoblast cells, chrondrocyte cells and mesenchymal stem cells; or for instance bacteria, for example bacteria which are commonly found in or on the human body, for instance gut bacteria).

Typically the second gel precursor material is added at an inlet downstream from the inlet at which the first gel precursor material was added. Typically, the second gel precursor material does not mix with the immiscible medium which forms plugs between portions of the first gel precursor material. The second gel precursor material is typically immiscible with the plugs.

Also typically, the first gel precursor material has partially gelled in the microfluidic channel at the time at which the adjoining portion of the second gel precursor material enters the microfluidic channel. The addition of the second gel precursor material after the first gel precursor material has partially gelled reduces the likelihood of mixing between the two media.

In some embodiments, the injection of a second gel precursor material adjacent to a portion of a first gel precursor material in the microfluidic channel is controlled by controlling the flow rates of any or all of the substances entering the microfluidic channel. For example, the flow rates of any combination of (i) the first gel precursor material, (ii) the immiscible medium (which does not mix with the first gel precursor material), and (iii) a second gel precursor material are controlled. Typically the flow rates of any or all of the additional substances added to the microfluidic channel are also controlled.

In some embodiments, the injection of a second gel precursor material adjacent to a portion of a first gel precursor material in the microfluidic channel is controlled by controlling the time at which the second gel precursor material enters the microfluidic channel. In these embodiments, the flow rate of the second gel precursor material is typically controlled to be non-zero only when a portion of the first gel precursor material is about to pass, or has just passed, the inlet at which the second gel precursor material is introduced.

Introduction (e.g. injection) of additional portions of gel adjacent to existing portions of gel within a microfluidic channel may typically be used to form gel objects comprising at least two regions of differing composition, for example three or four regions of differing composition. Typically, the regions of differing composition in each such gel object comprise a first region and a second region, the first region having a composition which is different from that of the second region. The first and second regions may be as further defined hereinbefore for the gel objects described hereinbefore.

Thus, in some embodiments, process of the invention may be used to form gel objects comprising at least two regions of differing composition. Typically, the regions of differing composition comprise the same gel. For example, the regions of differing composition may comprise different additives such as different small molecules or different biological cells. The regions of differing composition may however comprise different gel-forming agents.

This method of creating gel objects, which may be performed using a single microfluidic channel, e.g. microfluidic tube, is highly advantageous as it greatly reduces the occurrence of clogging of the microfluidic channel compared to previous methods of producing gel objects. Previous methods of producing gel objects comprising regions of differing compositions have tended to rely on the co-extrusion of laminar flows of different kinds of gel, or gels having different compositions. That approach tends to lead to clogging or uncontrollable variation in the thicknesses of the adjacent flows, and hence to gel objects whose precise composition cannot be controlled.

As has been mentioned, the time at which substances are added to the microfluidic channel may be controlled, typically by a flow control device. This may be exploited to generate complex individual gel objects as discussed above. However, this aspect of the process may also be synchronised with the location at which the gel objects are dispensed in order to create regions of differing composition.

Differing substances may be added to a microfluidic channel at differing times. For example, a first gel precursor material comprising a first type of gel-forming agent may be added for a period of time in order to create a region of the network comprising a first type of gel object.

The flow of this substance may be stopped after a period of time and a gel precursor material comprising a different type of gel-forming agent may be begun, in order to create a region of the network comprising a second type of gel object. Networks may thus be formed which comprise more than one type of gel. Different gels may be employed in different regions of such a network.

The time at which differing substances enter the microfluidic channel may be synchronised with the specific locations at which gel objects are dispensed to create regions within the network of particular types of gel object. For instance, by controlling the time at which differing substances are injected in combination with the location at which gel objects are dispensed it is possible to create, for instance, a network comprising layers of different kinds of gel objects without switching apparatus.

In some embodiments of the invention, the creation of gel objects of differing compositions in a desired sequence in a microfluidic tube or tubes can be adjusted to create a particular pattern of objects within the network. The sequence in which gel objects are created in the microfluidic tube or tubes can be programmed to produce a particular sequence of gel objects in the network. By "programmed" is meant that the gel objects are created in a sequence which has been previously designed. For example, the sequence in which the gel objects are created in the microfluidic tube or tubes can be programmed to produce different populations of gel object in particular regions of the gel network.

As will be appreciated from the above discussion, the process of the present invention allows the generation of a complex network comprising multiple different types of gel object, even gel objects having regions of differing composition, using a single tube. The process of the present invention therefore utilises a very simple apparatus compared to known methods. Moreover, the apparatus is easy and cheap to manufacture.

Additionally, the high degree of automation of the process enables a network to be printed very rapidly, highly reproducibly, and with minimum scope for human error.

In some embodiments, the gel objects can be produced at a rate of up to 100 objects per second ($s^{-1}$). Typically, in the process of the invention, gel objects are produced at a rate of 1 to 100 $s^{-1}$ and usually at a rate of 5 to 50 $s^{-1}$. In embodiments where the process produces fairly rigid gel objects (such as gelatin methacrylate objects), the rate of production is typically 20 to 50 $s^{-1}$. In embodiments where the process produces softer gel objects (such as matrigel objects), the rate of production is typically 1 to 15 $s^{-1}$. However, if a plurality of microfluidic channels are used to produce multiple gel objects simultaneously then much higher rates of production may be achieved.

3D Printing—Positioning of the Gel Objects

The process of the invention enables each gel object to be dispensed, or "printed" in a precise location relative to other objects within the gel network. This is typically achieved by moving a microfluidic channel from which a gel object is dispensed relative to the region for producing the network (i.e. the region outside of the microfluidic channel into which the gel objects are dispensed and the gel network is formed) between dispensing each gel object from said microfluidic channel. The process of the invention typically therefore comprises moving a said microfluidic channel relative to the region for producing the network in between dispensing gel objects from said microfluidic channel. Once dispensed, the gel object typically joins to at least one other gel object within the network and thus the position and orientation of the gel object within the network is fixed.

Moving the microfluidic channel and the region for producing the network relative to one another may be achieved by moving either or both of said channel and said region. Preferably, the microfluidic channel is moved and the region for producing the network is kept stationary. In other embodiments, however, the microfluidic channel is kept stationary and the region for producing the network is moved. Moving the region for producing the network may be achieved for instance by moving a stage which supports the region for producing the network, or for instance by moving a stage which supports a receptacle suitable for containing the region for producing the network.

The position at which each gel object is dispensed (and hence its ultimate location within the network) may be controlled by a computer programme. As has been discussed previously, the position at which each gel object is dispensed may be synchronised with the type of gel object which is being dispensed from each microfluidic channel in order to create a complex network.

The process of the invention is essentially a 3D printing process. The network of the invention is built from the inside out. This allows the creation of gel networks which could not be created other than by a 3D printing process. For instance, the process of the invention can be used to create interlocking rings, and even more complex structures, especially when more than one microfluidic channel is used to allow the simultaneous creation of differing regions of the network.

Typically, each gel object is dispensed adjacent to at least one other gel object in said region for producing the network. The process of the invention generally comprises controlling the position (typically meaning the position in three dimensions) at which each gel object is dispensed relative to other gel objects in said region for producing the network. This determines the position in the network of each gel object relative to the other gel objects. The process of the invention typically also comprises controlling (typically meaning controlling in three dimensions) the orientation of each gel object that is dispensed relative to other gel objects in said region for producing the network. This determines the orientation in the network of each gel object relative to the other gel objects. The gel network may have the shape of an organ or tissue within the human or animal body, and the process typically comprises said controlling, as defined above, in order to produce said gel network having said shape. The gel network may for instance have the shape of a human small or large intestine, or the shape of a section of human small or large intestine.

The printing of a large network may be accelerated by the use of multiple microfluidic channels, so that multiple regions of a gel network may be formed simultaneously.

The Region for Producing the Network

The region for producing the network may be any volume or medium that is suitable for receiving gel objects, i.e. any volume or medium into which the gel objects may be dispensed and contacted with one another to produce a gel network in accordance with the process of the invention. The region for producing the network may also be referred to herein as the "region in which the gel network is formed". The region for producing the gel network typically comprises a fluid medium. Preferably, the medium is a liquid medium, for example a hydrophobic liquid (preferable when the gel objects are hydrogel objects) or a hydrophilic liquid. Typical examples of liquid media which are present in the region in which the gel network is formed include water and oil-based media. Typically, the medium is a hydrophobic liquid such as an oil or a non-polar organic solvent. Suitable oils which may be employed as the liquid in the region for producing the network include hydrocarbon oils. $C_{10}$-$C_{20}$ alkanes may for instance be employed. Tetradecane is often employed. The hydrophobic liquid is typically an oil. The oil may be a single, pure, compound, or the oil may comprise a mixture of two or more compounds. The oil may for instance comprise silicone oil (for instance poly phenyl methyl siloxane). The oil may consist of a single silicone oil, for instance poly phenyl methyl siloxane. Alternatively, the oil may comprise a mixture of two or more different silicone oils. Any suitable silicone oil may be used. For instance, the oil may comprise silicon oil DC200 (a polymer comprising monomer units of —O—Si(CH$_3$)$_2$—), poly(dimethylsiloxane) (PDMS), hydroxy terminated, or PDMS 200. Additionally or alternatively, the oil may comprise a hydrocarbon. When the oil comprises a hydrocarbon it may comprise a single hydrocarbon compound, or a mixture of two or more hydrocarbons. $C_{10}$-$C_{20}$ alkanes may for instance be employed. Tetradecane is often employed.

Where the region in which the gel object is formed comprises a fluid medium, especially a liquid medium, said medium is preferably immiscible with the gel object. If said medium is miscible with gel objects within the gel network, it may penetrate into the bulk of the gel objects, which would generally be undesirable.

The region in which the gel network is formed may comprise a surface, typically a solid surface, on which gel objects may be disposed. Optionally at least one gel object in the gel network is disposed on a surface in the region in which the gel network is formed. For example, in the process of the invention, at least the first gel object dispensed may be disposed on a surface (generally a solid surface) in the region in which the gel network is formed.

Further Process Steps

The process of the invention may comprise a range of additional process steps, some of which are discussed below. It should be noted that the gel network of the invention may optionally be formed by some of these additional process steps.

The process may comprise an additional cross-linking step. For example, the process may comprise an irradiation step (e.g. by ultraviolet light) in order to initiate cross-linking (e.g. polymerisation). In such a case, gel objects within the gel network may comprise a photoinitiator. The gel precursor material (or the gel precursor materials) from which the gel object are formed in the microfluidic channels will typically further comprise a photoinitiator in such cases. Another method by which the additional cross-linking step may be achieved is by thermal initiation of cross-linking, for example thermal initiation of polymerisation. Additionally cross-linking step may be achieved by enzymatic reactions, which will typically further comprise enzymes in such cases (see, for example, J. Lewis et al, PNAS, 113, 3179-3184, 2016). The process of the invention may therefore further comprise a heating or baking step.

Performing an additional cross-linking step may create covalent bonds between the gel particles (typically polymers). Therefore a gel network which has been subjected to an additional cross-linking step is typically therefore strengthened by the process.

Alternatively, an additional cross-linking step may be performed on the gel objects before they are dispensed from the microfluidic channel. However, the cross-linking of gel particles within the gel objects before they are dispensed is typically incomplete so that gelling may occur between gel objects when they are brought into contact.

The process may comprise an incubation step, wherein the gel network (or gel objects) are maintained at a particular temperature for a period of time. For example, the gel network may be incubated at a temperature below the sol-gel transition temperature of the constituent gel or gels after the network is formed in order to promote further gelling. Alternatively, the gel objects may be incubated at a temperature below the sol-gel transition temperature to promote gelling within a microfluidic channel.

The process may comprise a transfer step, wherein the gel network is transferred from one medium to another. For example, where the gel network is produced in a region comprising a liquid medium which is immiscible with the gel objects in the network, the process may comprise a step of transferring the gel network from the liquid medium which is immiscible with the gel objects to an aqueous medium. The nature of the transfer step is not particularly limited. For instance, the transfer may involve moving the gel network out of the liquid medium with tweezers and depositing it into the aqueous medium. Alternatively, the transfer may involve pouring or pipetting the liquid medium off the gel network, and pouring or pipetting the aqueous medium onto the gel network. The aqueous medium is not particularly limited. It may be, for example, water or a buffer solution such as PBS.

As has been mentioned, the gel network of the invention is very robust. It may therefore be manipulated after it has been created. For example, the gel network of the invention may be cut, joined or stapled in order to alter the shape of the network or to combine two or more gel networks.

EXAMPLES

Experimental Details

1. Materials

All chemicals were purchased from commercial suppliers and used without further purification. Deionised water (DIW) was used in all aqueous phases. Gelatin methacrylate (GelMa) was synthesized as described in [JW Nichol, Biomaterials, 2010]. Briefly, 10.0 g gelatin (Type A, G1890, 300 bloom from porcine skin, Sigma-Aldrich, UK) was dissolved at 10.0 wt % into Dulbecco's phosphate buffered saline (DPBS; GIBCO, Sigma-Aldrich, UK) at 60° C.; 0.8 ml methacrylic anhydride (MA, Sigma-Aldrich, UK) was added at the rate of 0.5 ml/min to the gelatin solution under continuously stirring at 45° C. and further reacted for 1 h. The mixture was dialyzed against DIW using dialysis tubing (12-14 kDa cutoff, Sigma-Aldrich, UK) for 4 days at 40° C. DIW was changed for every 12 hours. The solution was lyophilized, redissolved in DPBS at 8.0 wt %, aliquoted and stored at −20° C. until further use.

2. Printing Setup

The printing setup consisted of two parts: one was the microdroplet formation and gelation in DMT and the other was the 3D printing guided by a triple axis micromanipulator (Sensapex, Oulu, Finland). GelMa DPBS solution was warmed up to ~40° C. in a 1 ml BRAUN Inject-F plastic syringe by a Halogen heater, and conducted via a piece of PTFE tubing (560 μm ID, 1 mm OD Cole-Parmer, UK) to a handmade 3-way PDMS adaptor, driven by a flow rate-controlled neMESYS syringe pump (Cetoni, Korbussen, Germany); oil was pumped to the connector in the same way. A third PTFE tubing (200 μm ID, 400 μm OD, VWR, UK) was connected to the adaptor, and both phases merged and formed GelMa droplets carried by oil that wetted the emulsification tubing. The emulsification tubing was chilled in a wine cooler set at 8° C., where printing was performed. GelMa/oil flow rates were controlled independently by the pump software. Sizes/morphologies of GelMa droplets varying from microspheres to elongated moieties were obtained by adjusting flow rates and flow rate ratios of oil-to-GelMa phases. When incubated at low temperature, droplets underwent a sol-gel transition when approaching the tubing outlet. The GelMa building blocks were patterned into 3D networks in oil contained in a petri dish (or a beaker for printing tubes), and phase transferred to water (or to DPBS buffer or cell culture medium) by pipetting. Typically, oil is pipetted out and water or aqueous solution pipetted in to the petri dish or beaker. Parallel networks were printed by moving the tubing outlet stepwise or constantly at various speeds, driven by the manipulator commanded by a Labview coded user interface; the tubing outlet was deflected by a tweezer to obtain an acute angle with the substrate, as shown in FIG. 1a, in order to orient microrods exiting the tubing. Circular/tubular networks were made by rotating the petri dish or beaker at a constant angular speed, driven by a homemade motorised rotator. Throughout these Examples the oil phase was tetradecane and the PTFE tubings forming and carrying droplets were 200 μm in internal diameter (ID), unless noted elsewhere. The rods were composed of 6.0 wt % GelMa in DPBS unless otherwise noted. Throughout the experiment, the tubing incubation length at 8° C. was approximately 20 cm long, whereas for formation of Janus rods, the tubing was around 30 cm long. The sum of the volume flow rates in most cases were maintained at 500-2000 ul/hr. GelMa was coloured by food dyes (Ateco Food Coloring Kit, US) at approximately 1:1000 dilution.

The angular velocity during patterning ranged from 0.37 to 6.3 rad s$^{-1}$.

The Matrigel rods were fabricated in PTFE collection tubing with an internal diameter of 300 μm, and the tube was around 1.2 m long for fabricating homogeneous rods and 3.0 m long for Janus/ternary rods.

3. Crosslinking

Thermal stability of GelMa was improved by UV crosslinking. [JW Nichol, Biomaterials, 2010] Briefly, 0.5 wt % 2-hydroxy-1-(4-(hydroxyethoxy)phenyl)-2-methyl-1-propanone (Irgacure 2959, CIBA Chemicals) were added to GelMa solution as a photoinitiator prior to injection. The coloured printed networks were transferred to water loaded with 0.5 wt % 2959, purged in $N_2$ for 30 min and exposed to a full power UV lamp (M365L2-C5, 700 mA, 15 V, Thorlabs, UK) at the distance of 5 cm for 5 min (non-coloured network was UV crosslinked for 1 min). The crosslinked network was then refreshed with water. Photo-crosslinking rendered the GelMa rods stable at 37° C.

4. Array Encased in PNIPAM

The GelMa microrod array was printed first; solution mixture of Nisopropylacrylamide (NIPAM; monomer, 8.0 wt % in PBS), Polyethylene (glycol) Diacrylate (PEGDA, MW=700; crosslinker), Ammonium persulfate (APS; thermosinitiator) and Tetramethylethylenediamine (TEMED; accelerator) at weight ratio of 200:20:1:10 was added dropwise to the array until fully covering it. The sheet was incubated at ambient for 20 min for polymerisation.

5. Imaging

Bright field images of higher magnification were captured by an Imaging MicroPublisher 5.0 RTV camera (QImaging, BC, Canada) mounted on an Olympus SZX10 stereomicroscope (Olympus SZX10, Tokyo, Japan), Micropublisher 5.0 RTV. Low magnification images were captured using a high-quality digital microscope (AM4113T, Dino-Lite, The Netherlands). Fluorescent images were obtained at room temperature on a Leica TCS SP5 STED (Leica Microsystems) inverted confocal laser-scanning microscope or a Leica DFC7000T colour microscope camera (Leica Microsystems (UK) Ltd, UK) mounted on an inverted Leica DMi8 microscope (Leica Microsystems (UK) Ltd, UK). All images were processed in the NIH ImageJ software. Confocal fluorescence images were processed by z-project in ImageJ.

6. Simulation

Simulation of flow conditions in tubing was done in the commercial finite element software COMSOL Multiphysics®, using the time-dependent two-phase flow, moving mesh module to simulate plugs and laminar single phase flow module to simulate SPF (single phase flow pattern). The surface tension between the aqueous-oil phase was measured as 0.015 mN/m by pendent drop method on an IT concept tracker, and the oil-PTFE contact angle was set as 44°, according to the literature [N Schelero et al., Soft Matter, 2011, 7, 10694.; E Dickinson et al., Colloids Surfaces, 1985, 14, 135-141; F MacRitchie, Chemistry at Interfaces, Academic Press, 2012, 1st ed, p 16].

The density of the tetradecane oil and the GelMa phases were measured to be 0.762 and 1.024 g cm$^{-3}$ respectively.

7. Cell Culture

Human embryonic kidney cells (HEK293T) were cultured in Dulbecco's Modified Eagle's Medium (DMEM; Sigma-Aldrich, UK), supplemented with 10% (v/v) fetal bovine serum (FBS, Sigma-Aldrich, UK) and 2 mM GlutaMax™-I (Gibco, Life technologies). NIH3T3/GFP was supplied from Cell Biolabs Inc., USA (Catalog number: AKR-214); the GFP gene was introduced into parental NIH 3T3 cells (ATCC® CRL-1658™) using lentivirus. NIH3T3/GFP cells were cultured in DMEM supplemented with 10% (v/v) bovine calf serum (ATCC®, US), 2 mM L-glutamine, 0.1 mM MEM Non-Essential Amino Acids (NEAA) and 10 μg ml-blasticidin. Cells were cultured at 37° C. and 5% $CO_2$, and passaged when they achieved 80-90% confluency. NIH3T3 cells were harvested by trypsinization (0.25% (w/v) Trypsin—0.53 mM EDTA solution). Viable cells were identified by Trypan blue exclusion (GIBCO, Life technologies), and counted in a hemocytometer. Normal human skeletal myoblasts (HSkM) was bought from Cell Biolabs Inc., USA (Catalog number: A12555). HSkM cells were cultured in DMEM supplemented with 2% (v/v) horse serum (Catalog number: 16050-130). CCD-18Co cells (ATC CRL-1459), colon myofibroblasts, were cultured in DMEM (supplemented with 10% FBS).

Printed tissue network was phase-transferred and cultured in DMEM supplemented with 10% FBS or 2% horse serum, 0.1 mM MEM non-essential amino acids (Gibco, Life technologies), 2 mM Glutamax, and 1% penicillin-streptomycin (Gibco, Life technologies, 100 U mL$^{-1}$ and 100 μg mL$^{-1}$ resp.) to suppress bacterial growth, at 37° C. and 5% $CO_2$.

Cell viability was characterised by staining cells with 2 μM calcein AM (Molecular Probes™, Invitrogen) and 4 μM propidium iodide (Sigma-Aldrich, UK) in culture medium, and incubated for 20 min before imaging. Images were obtained at 488 nm and 514 nm excitation and 520±20 nm and 620±40 nm emission for green (living cells) and red (dead cells), respectively. HEK293T cells were stained red with CellTracker™ Red CMPTX dye (Molecular Probes, Life Technologies, UK) for fluorescent imaging. Briefly, dye vials were warmed to room temperature, and dissolved in DMSO to a final concentration of 10 mM. The solution was diluted to 10 μM in serum-free medium and warmed to 37° C. as the working solution. HEK293T cells were harvested, centrifuged and resuspended in the CellTracker™ working solution. The suspension was incubated at 37° C. for 30 min, the cells were centrifuged and the CellTracker™ solution was pipetted out. Cell density was measured by haemocytometer. Then cells were loaded into GelMa solution at specific concentrations. Images were obtained at 488 nm and 514 nm excitation and 520±20 nm and 620-40 nm emission for cells stained green and red, respectively.

Networks cultured with CCD18Co cells were fixed in 4% (w/v) paraformaldehyde in PBS for 20 min at room temperature, washed twice with PBS. The networks were then rinsed in 10% (w/v) glycerol in PBS for 10 min and then washed twice with PBS. Alexa Fluor® 647 Phalloidin (A22287, ThermoFisher Scientific, UK) was added at 1:500 dilution in PBS, and incubated for 3 h at 37° C.; DAPI was added at 1:1000 in PBS and incubated for 20 min at room temperature before imaging.

The Experimental Setup

The process of the invention has been performed using a setup as sketched in FIG. 1(a). The setup comprises droplet-based microfluidics tubing (DMT). DMT is a modified microfluidics system that integrates droplet formation, conduction and gelation in a single piece of tubing. Carrier oil (which form plugs) and a flowable medium comprising gel particles (referred to hereafter as droplets) are injected into the tube and form alternating portions that avoid droplet-droplet or plug-plug contact, which waives the necessity for surfactants in DMT. In the following Examples, the flowable medium comprising gel particles consists of gelatin methacrylate (GelMa hereafter) in phosphate-buffered saline (PBS) solution. The carrier oil is tetradecane oil.

As is shown in FIG. 1(a), the GelMa and oil are stored separately in two syringes are pumped through conducting PTFE tubings (inner diameter ID=560 μm) into the emulsification PTFE tubing (ID=200 μm, 20 cm long), where monodisperse GelMa droplets form (at 30 to 37° C.) and gradually gel into rods when incubated in a wine cooler set at 8° C. when approaching the tubing outlet. A handmade 3-way polydimethylsiloxane (PDMS) adaptor connects the three tubings. The outlet is attached to a triple-axis micromanipulator; the axis movement is controlled by a program coded in Labview.

Microrods are patterned layerwise in tetradecane oil. Parallel or circular microrod arrays are patterned by either moving the tubing outlet or rotating the oil container. The tubing outlet, indicated by the arrowhead in FIG. 1(a), determines the microrod orientation from a stationary outlet. The tubing outlet is tilted at an angle of 30 to 45° with respect to the oil container, which determines the microrod orientation upon exiting the outlet. Networks printed in oil can be phase transferred to water by simply pipetting water or aqueous medium such as buffer to the oil container. The phase transfer of a circular network from oil to water is illustrated in FIG. 7.

Figure 1B:
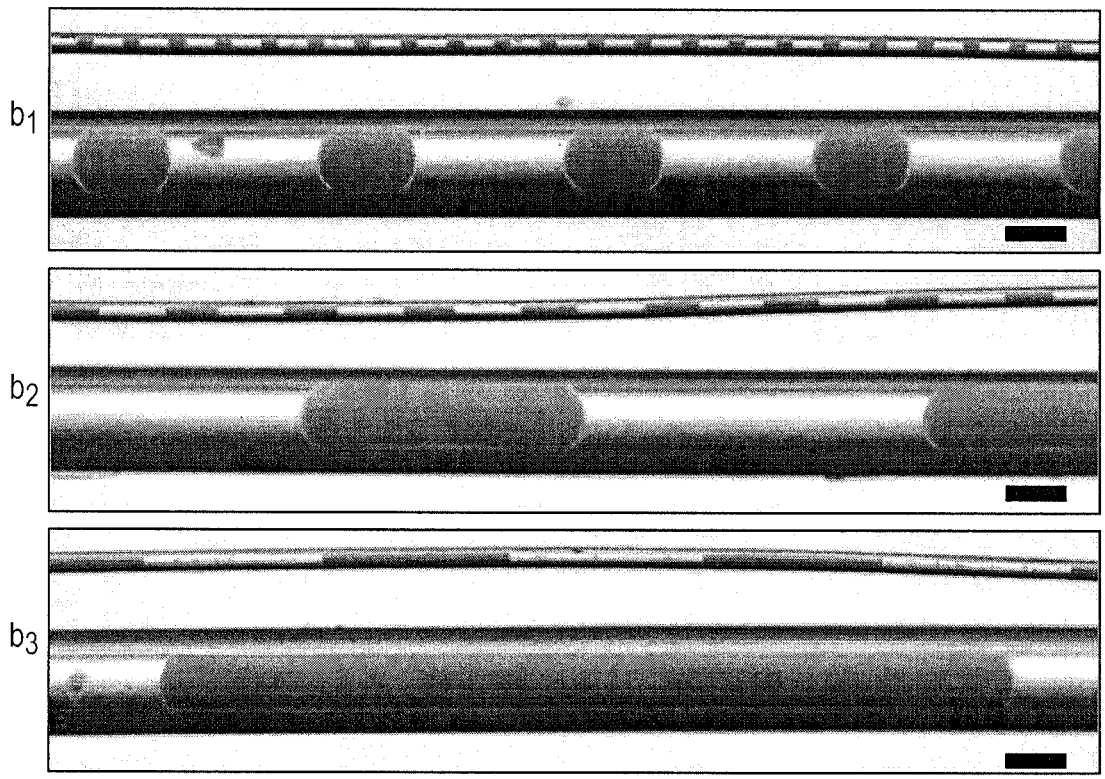

DMT allowed spatial and temporal control of GelMa microdroplets/objects, both before and after gelling, as they were equally spaced by oil plugs and adopted single file flow in the tubing, thus avoiding channel clogging as well. (FIG. 1b) GelMa was coloured with food dye to increase the colour contrast of droplets with oil and the tubing wall. The transverse diameters (D) of droplets were identical to the tubing ID, thus droplet size was represented by the aspect ratio α, defined as the ratio of the droplet length to its diameter.

Figure 1C:
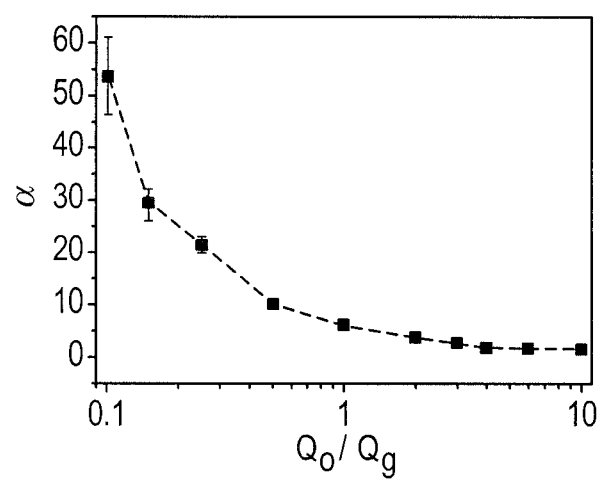

The aspect ratio was tailored by varying the volumetric flow rate ratio of the oil to GelMa phases ($Q_o/Q_g$); the dependence of α on $Q_o/Q_g$ is shown in FIG. 1c: at $Q_o/Q_g<1$, α decreased significantly with $Q_o/Q_g$, but at $Q_o/Q_g>2$, the dependence was substantially reduced. Monodisperse GelMa microspheres and microrods (D=200 μm) formed in 200 μm ID tubing are shown in FIG. 1d. Microrods of higher feature resolutions (D=100 μm and 50 μm) were obtained by using 100 μm and 50 μm ID tubings, respectively. (FIG. 1e). As the building blocks were intentionally controlled not to completely gel when exiting the tubing, they instantly formed fused interfaces when in contact in oil on the substrate; the interface gelled in oil and bound the constituent units, as shown in FIG. 1f of a microsphere chain and a microrod network. The fused interfaces provided mechanical strengths to overcome shear and gravity and were sufficient to support 3D networks patterned in the centimetre size range. The structural integrity of the constituent rods was sustained after the interfaces of the rods fused.

The dwell times of the microrods were controlled so that complete gelation did not occur before the rods exited the tubing. The objects then quickly fused at their interfaces after landing on the substrate, to form a microsphere chain or a microrod network (FIG. 1f). The fused interfaces provided mechanical strength against shear forces and gravity, and were sufficient to support 3D networks in the centimetre size range. In architectures patterned with gel microrods, the difficulty of building blocks sliding away from their initial placement, which often occurs when microspheres are patterned, is minimized. The structural integrity of the constituent rods was sustained after interface fusion. GelMa networks are stable at below 30° C.; photopolymerization of the methacrylate groups after phase-transfer to aqueous medium renders the gel networks stable at 37° C.

Patterning Parallel Microrod Array and Array-Guided Shape Transformation

Microrods exiting the tubing were initially oriented as determined by the tubing but the orientation was affected by hydrodynamic torques induced by movement of the tubing outlet. The relationship between the printing path (the line along which the tubing outlet moves) and the eventual pattern created by the rods dispensed therefrom is illustrated in FIG. 8. This Figure illustrates a parallel printing path. GelMa rods can be oriented in parallel by translocation of the tubing outlet while keeping the recipient container stationary. That is, the orientation of the microrods was determined by the horizontal positioning of the tilted tubing outlet when the translocation was slow and the shear forces low. At higher translocation speeds, shear forces reorient the microrods exiting the outlet and prior to landing on the substrate.

FIG. 2 shows parallel arrays of GelMa microrods patterned in oil (FIGS. 2*a* and 2*c*), and after being phase-transferred to water (FIGS. 2*b* and 2*d*), under different modules of the tubing movement. 3D networks were obtained by overprinting along the original path. The direction of each microrod is represented by angle φ, defined as the angle between the longitudinal axis of the rods and the printing path. FIGS. 2*a'*-2*d'* plot the normalised frequency of φ in associated images on the left, exhibiting either a single normal distribution peaked at 60° (FIGS. 2*a'* and 2b') or double normal distributions peaked at 800 and 1000, respectively (FIGS. 2*c'* and 2*d'*). Single population networks were patterned by stepwisely moving the tubing outlet at small step sizes, such as the tubing outlet moving at 0.15 mm per step per 0.2 sec; by contrast, double population, or herringbone, networks were patterned by constantly moving the tubing outlet at higher velocities, which varied φ due to different magnitudes of the induced hydrodynamic torques. At velocity v=2.0 mm/s, the array peaked at 80° and 100° (FIG. 2*c*), whereas at v=5.0 mm/s, the peaks became more separated to 60° and 110°, respectively (FIG. 9*a*). The average angle of each parallel microrod array was identical to the horizontal orientation of the tilted tubing outlet. The printed networks were sustained after being phase-transferred from oil to water, without significant change in the frequency distribution of φ. (FIGS. 2*a'* to 2*d'*)

Figure 2F:
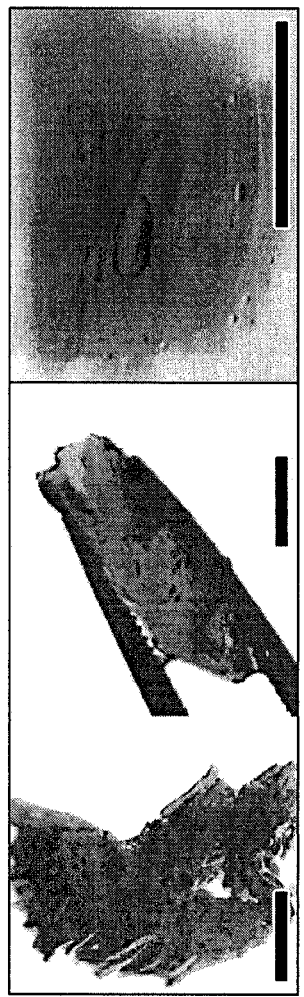
FIG. 2 illustrates the control which may be exerted over the patterns or microrods in an array, and further illustrates collective guided shape transformations of the patterned network.
Figure 2E:
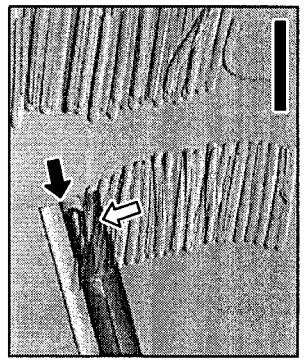

Patterning microrods of higher feature resolutions (D=100 μm and 50 μm) into parallel arrays were achieved and are shown in FIG. 10. The microrod arrays bounded by fused interfaces between the constituent gel objects were sufficiently robust to be handled with a tweezer. In FIG. 2*e*, the array was lifted up by a tweezer and suspended on tubing; in FIG. 2*f*, the parallel array was rolled up in oil, picked up by a tweezer and resuspended in water, all the while maintaining the structural integrity of the constituent rods.

Figure 2H:
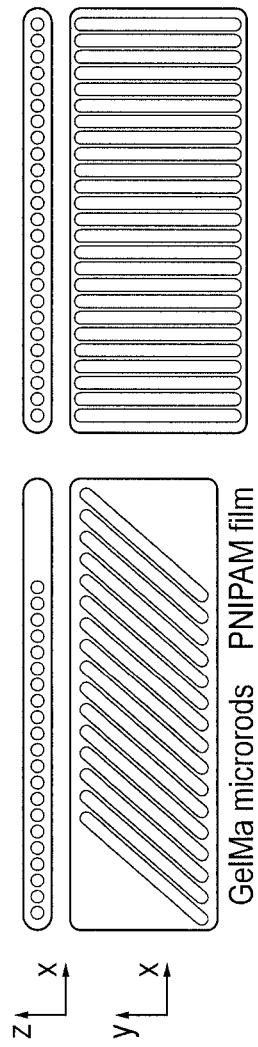
Figure 2G:
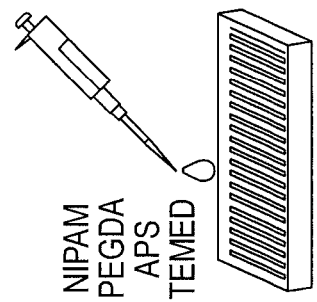
Figure 2I:
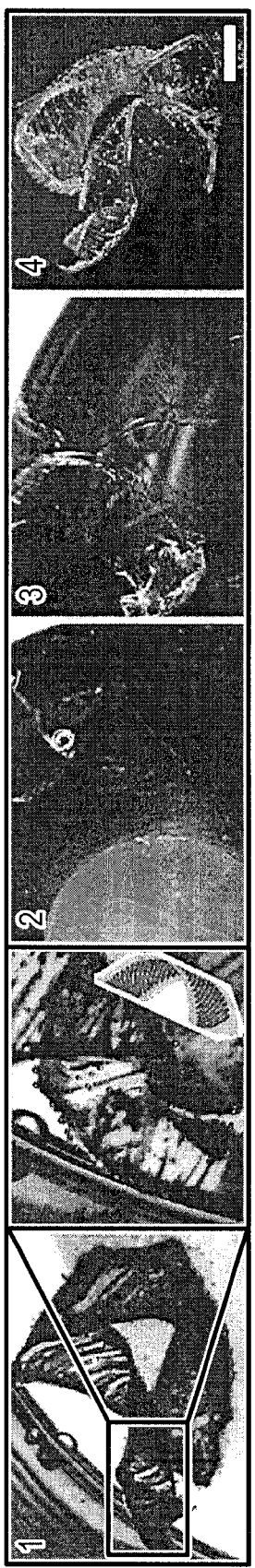
Figure 2K:
Figure 2J:
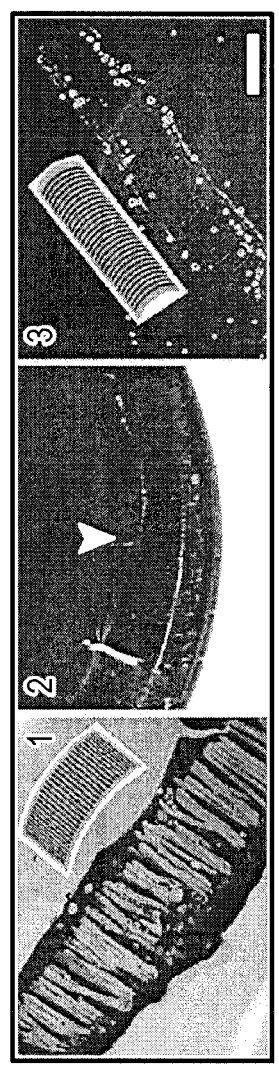

Shape transformations of gel sheets have been found to be steered by heterogeneity in small scale stiffness. As illustrated in FIGS. 2*g* and 2*h*, the patterned arrays were enclosed by poly(N-isopropylacrylamide) (PNIPAM), forming hybrid thermo-responsive sheets. In FIG. 2*i*, when the microrods were arrayed at φ=45° C., the hybrid sheet relaxed in cold water (below the lower critical solution temperature (LCST, 32° C.) of PNIPAM) and transformed to the helical shape in hot water (above LCST) due to the higher stiffness of embedded GelMa (3.6 kPa) rods than PNIPAM at LCST (1.5 kPa) [B. Sierra-Martin et al., Phys Rev E, 2011, 84, 011406]. The transformation was reversible. When q=90° as shown in FIG. 2*j*, the microrod array resisted twisting and the sheet arced along the longitudinal axis. After relaxing in cold water, the sheet slightly bent along the transversal axis when reshaped in hot water. The herringbone microrod array overcame the twisting effect above LCST thus the sheet in FIG. 2*k* failed to gain the helical configuration.

Patterning Circular Microrod Arrays

Microrods were patterned circularly by rotating the oil container, mostly a petri dish, at a constant velocity. This constant velocity is an angular velocity, ω. FIG. 3*a* shows 2D circular patterns of various hydrodynamic radii at certain angular velocities, where the microrod orientation varied with the hydrodynamic radius. The microrod orientation varied with the radius of the circular array, r, because the shear force on the ejected rods is proportional to the tangential velocity v (v=r·ω) at the tubing outlet with respect to the oil container (FIGS. 3*a* and 11). FIG. 3*b* defines the direction in the circular pattern represented by angle θ, as the angle from the radial vector of a rod to the longitudinal axis of the rod. Under this definition, microrods in each circle are oriented identically; θ is determined by both the orientation of the tilted tubing outlet as well as the hydrodynamic torque, which is proportional to the tangential velocity v. The hydrodynamic torque is the shear force on the ejected rods. In FIG. 3*c*, which shows rigid microrods with α=7, θ decays with v until reaching 90°; the dependence fits the Jeffrey's equation (FIG. 11; GB Jeffery, Proc R Soc London, 1922, 102, 161-179; Papathanasiou and Guell, Flow induced alignment in composite materials, Woodhead, Cambridge, 1997, p 46) and is presented as:

$$\theta = \pi/2 - \arctan(a \cdot \tan(b \cdot v - c))$$

where a, b, c are constants.

Aspect ratio also affects orientation as the hydrodynamic torque is related to the superficial area of the microrods. The experimental paradigm in FIG. 3*d* shows that θ has significantly negative dependence on both α and v. High aspect ratio rods (e.g. α>10) are flexible and do not fit the equation (1), but their orientation follows the decay trend.

Figure 3G:
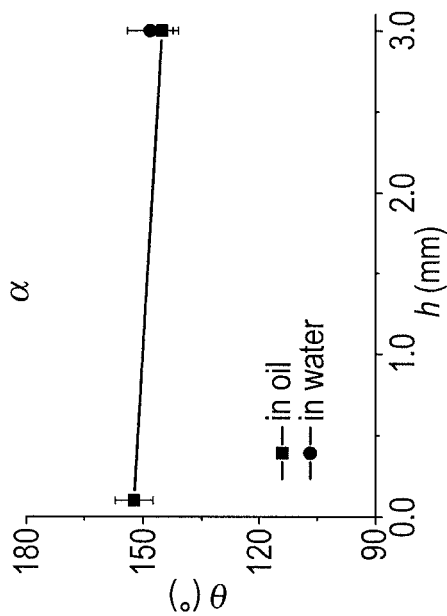
Figure 3F:
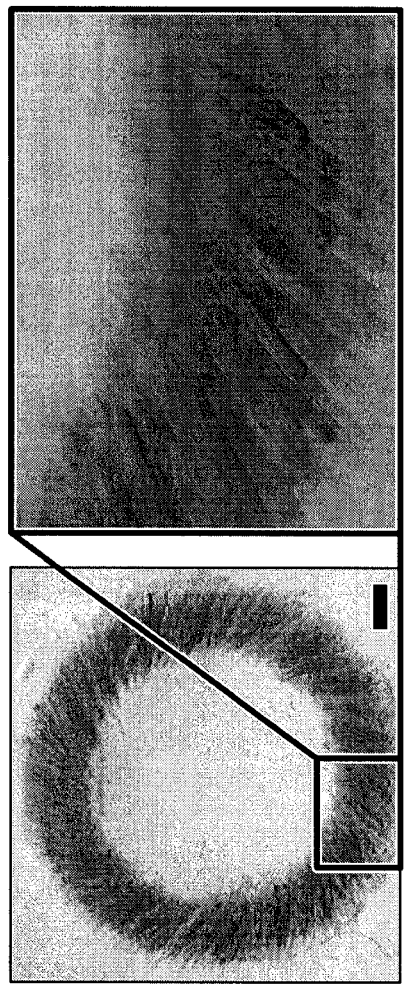
Figure 3J:
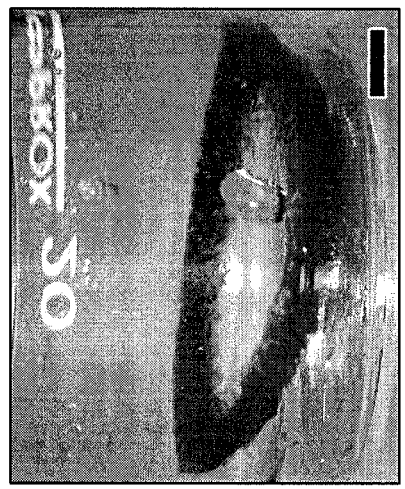
Figure 3I:
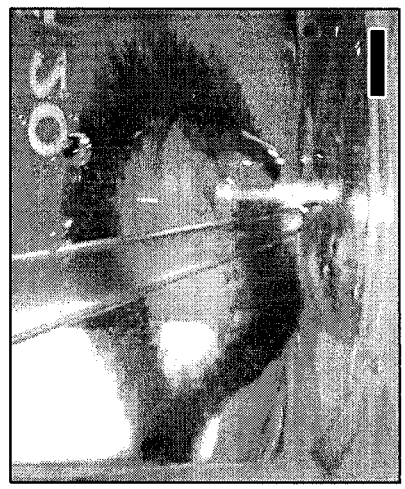
Figure 3H:
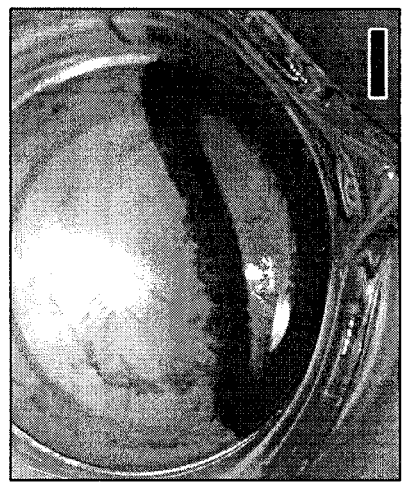

The 2D circular patterning can be extended to 3D printing by stacking microrod arrays above one another. FIG. 3*e* shows a 3D circular microrod array approximately 3 mm in height in oil and the zoom-in of the wall. The circular network was sustained after being phase-transferred to water by pipetting. (FIG. 3*f*) FIG. 3*g* gives the angle θ of the circular network in oil and water: θ changed insignificantly (<5%) from the bottom layer to the top layer, and was identical in both oil and water. FIGS. 3*h* to 3*j* sequentially show the circular microrod array in water; scraped off the substrate and suspended against the beaker wall; deformed by a tip; and having regained the circular shape after free floating in water. More circular network printing are provided in FIG. 9.

Individual microrods can be picked up and redeposited by pipetting to dope another network, which can potentially be used as in vitro co-culture models. (FIG. 12)

Programmed Patterning of Different Types of Microrods

Most organs/tissues comprise different types of tissues/cells, which motivates the development of patterning different types of microrods according to a programmed design. A third syringe stored with oil was connected to a long conducting tubing (ID=570 μm) and a dye reservoir; concentrated dye solutions were partitioned into multiple single-colour objects (8 cm long) in the tubing by short air plugs (1 mm long), as sketched in FIG. 4*a*. The length of the tubing varied depends on the number of gel+dye objects partitioned. All tubings were connected with a handmade 4-way PDMS adaptor.

A concentric circular network composed of 5 colour microrods were sequentially patterned from the inner to outer circles according to the sequence of partitioned dye objects (FIG. 4*b*); in principle, there is no limitation in the number of microrod types being patternable. The multi-colour network was sustained in phase-transfer. Lamellar patterning was achieved by fixing the tubing outlet horizontally but levelling it up synchronously with the increase in the pattern height. (FIG. 4*f*)

As the colour reservoirs were partitioned with short air plugs, ill-shaped microrods were generated when the air plugs were injected into the emulsification junction and presented in the printed network. However, such rods are very low in fraction and would not affect the overall properties.

Patterning Janus Microrods

Figure 5A:
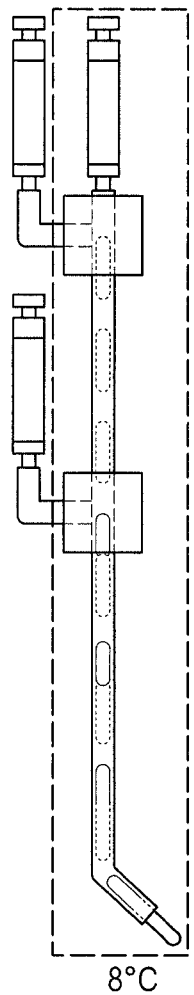
Figure 5B:
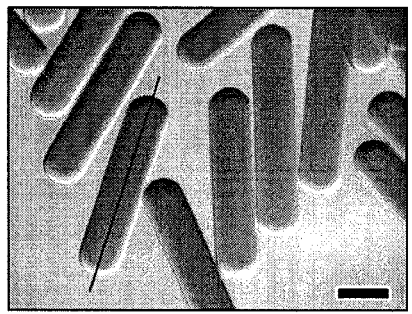
Figure 5B:
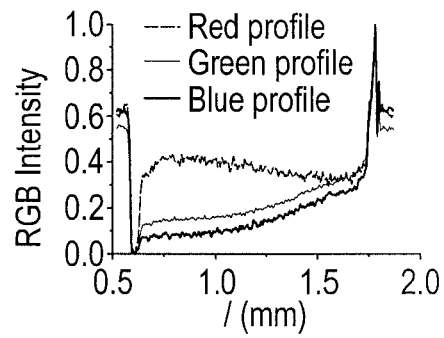
Figure 5C:
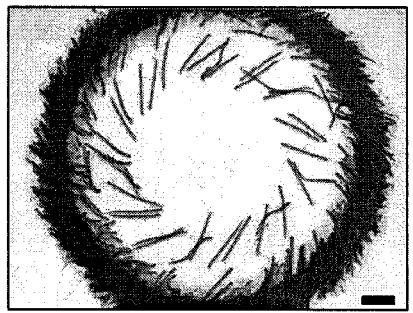
Figure 5C:
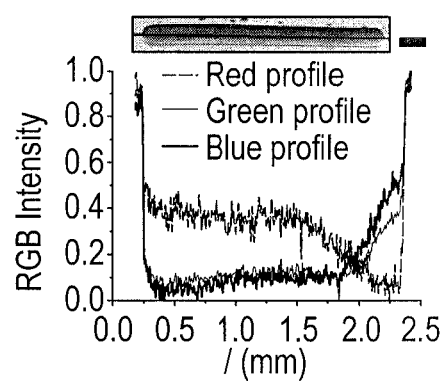
Figure 5D:
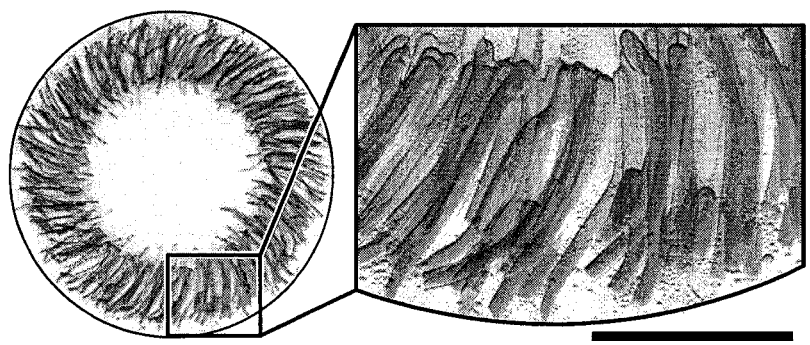

Janus microrods have asymmetric compositions. They are comprised of adjoined individual rods with distinctive chemical and physical properties as well as directionality, [2013 A. Walther, et al. Chem Rev, 2013, 113, 5194-5261; Z. Nie et al., J Am Chem Soc, 2005, 127, 8058-8063.]. The patterning of Janus microrods is promising in creating complex tissues by encapsulating different cell types in separate compartments of a gel object. Janus microrods were fabricated in DMT by sequentially injecting two GelMa phases into the emulsification tubing: GelMa coloured red was introduced at the first emulsification junction, forming red plugs first and gradually gelling at 8° C. incubation; GelMa coloured green was injected secondly at the halfway point of the tubing and merged with the gelled red plug, forming red/green Janus rods after secondary incubation. (FIGS. 5a and 5b, α=5) FIG. 5c shows a circular 3D network (h=1.5 mm) patterned from blue/red Janus rods (α=14). The RGB profiles in FIGS. 5b' and 5c' exhibit high contrast of colour combinations along a cross section taken along the black line drawn through an individual object. When the carrier oil was loaded with 0.2 wt % Span 80 surfactant to impede instantaneous fusion of the green and red constituents, sharp green/red interfaces were found in the obtained Janus rods. (FIG. 5d)

Tubes of Microrod Arrays as In Vitro Small Intestine Model

Developing in vitro small intestine models has attracted extensive attention in the past decade. Intestinal organoids differentiated from single stem cells in the absence of a non-epithelial cellular niche [T. Sato, et al, Nature, 2009, 459, 262-266; J R Spence, et al, Nature, 2011, 470, 105-110] resembled many aspects of intestine tissue, and has been tested in intestine therapy [S Yui, et al, Nat Med, 2012, 18, 618-623.]. However, such organoids lacked spatial and morphological controllability and failed to fully resemble intestine functions. For instance, the organoids budded outwards due to the absence of muscle layer compression; secondly, the absence of immune and mesenchymal cells in organoids limited their potentials as intestine disease model. [CA Lindemans, et al, Nature, 2015, 528, 560-564.] By grafting in vitro grown human intestinal organoids with the supportive mesenchyme in mice, the in vivo matured model gained more intestinal functionality, such as the responsiveness to physiological stimuli; however, this approach is particularly time-consuming (over 5 months in total) and the obtained model lacks reproducibility in morphology. [CL Watson, et al, Nat Med, 2014, 20, 1310-1316.]

Soft-lithography or mold casting either engineered planar villi-like structures or tubular epithelium in the absence of villi. [J H Sung, et al, Lab Chip, 2011, 11, 389-392; Y Chen, et al, Sci Rep, 2015, 5, 13708.]

Figure 6D:
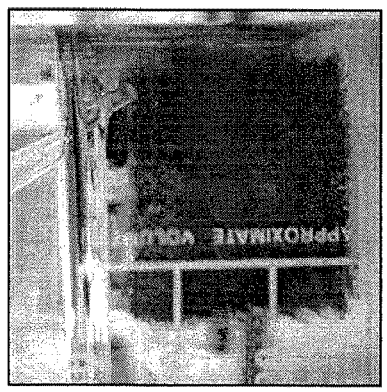
Figure 6H:
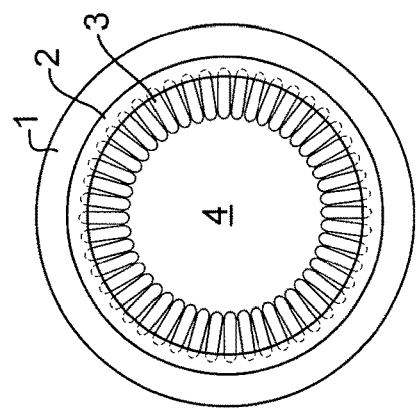
Figure 6C:
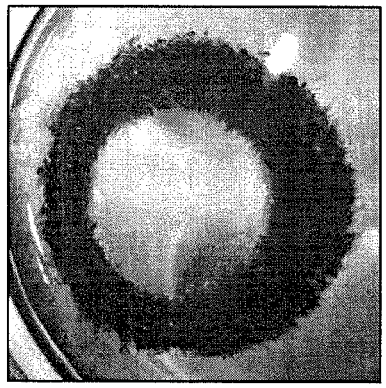
Figure 6G:
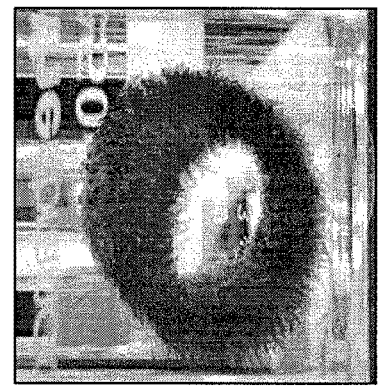
Figure 6B:
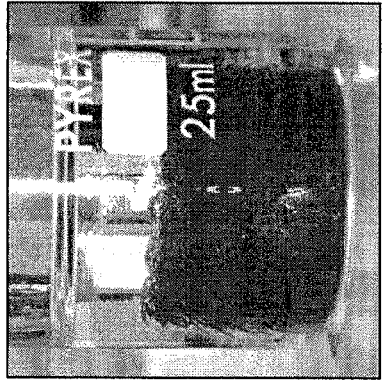
Figure 6F:
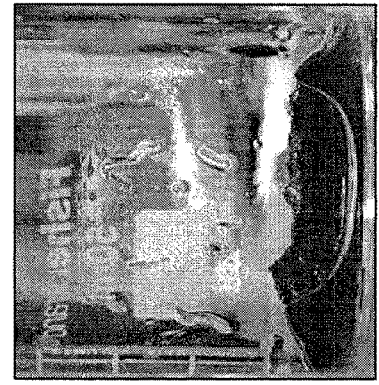
Figure 6A:
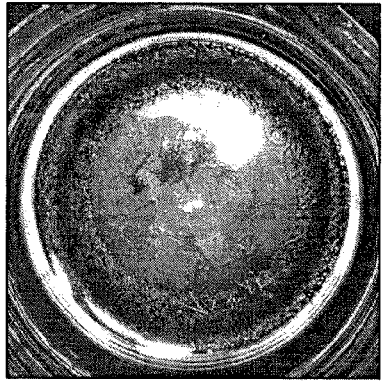
Figure 6E:
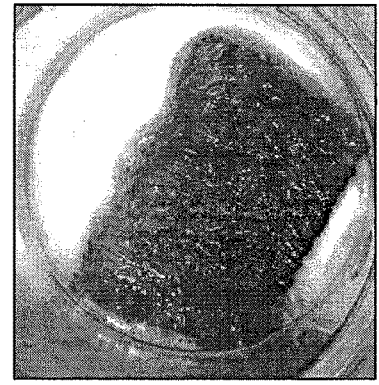

In an attempt to create an in vitro small intestine models consisting of interior villi and the circumferential muscle layers [A E Shyer, et al, Science, 342, 212-218; 2011 Tortora, Principles of anatomy & physiology], GelMa microrods were patterned into tubes in the centimetre size range, matching the dimension of human intestinal lumen. This was achieved by depositing hundreds of layers of microrods vertically. FIGS. 6a-6d show the top-view and side-view of a printed tube (approximately 2 cm in height and 2 cm in diameter) in oil and suspending in water after phase-transfer. These dimensions are similar to those of the lumen of the human small intestine. The tube was resilient; it collapsed in the absence of buoyant force from water but instantaneously restored the tubular shape when being flushed and resuspended by water. (FIGS. 6e-6g)

Figure 6L:
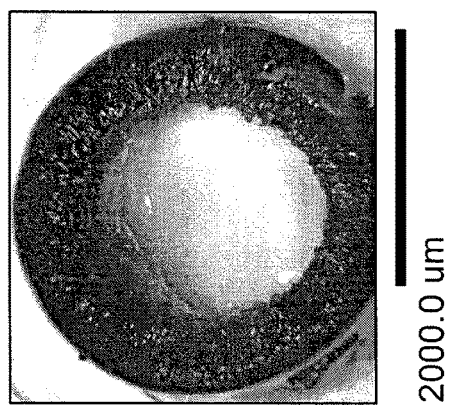
Figure 6K:
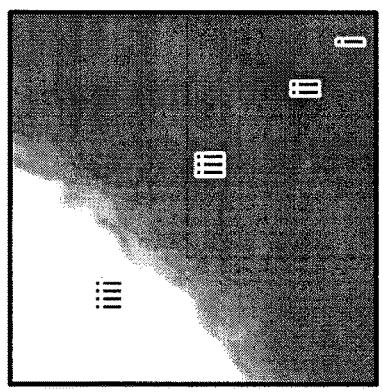
Figure 6J:
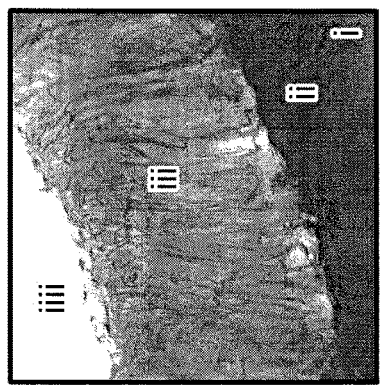
Figure 6I:
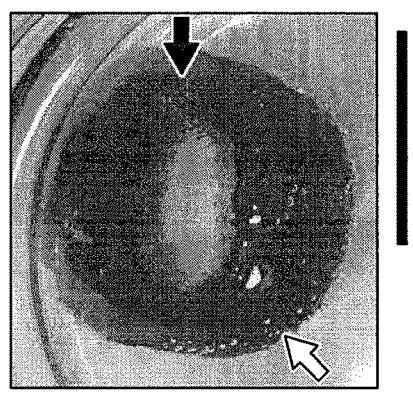
Figure 7C:
Figure 7B:
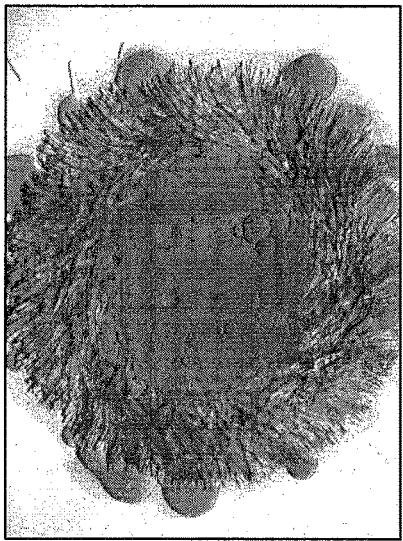
Figure 7A:
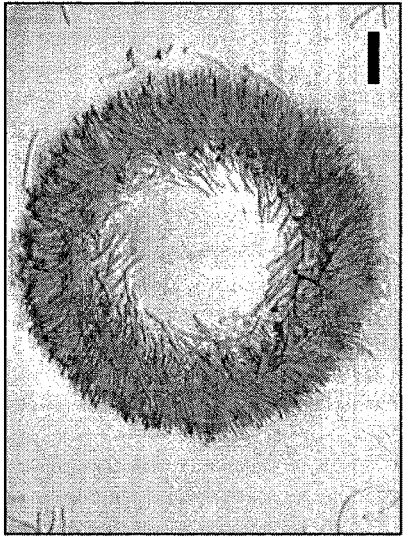
Figure 7E:
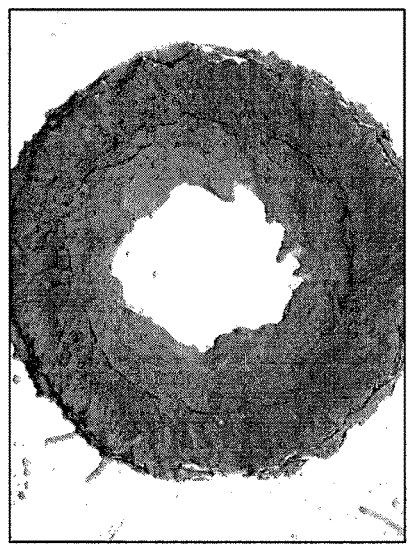
Figure 7D:
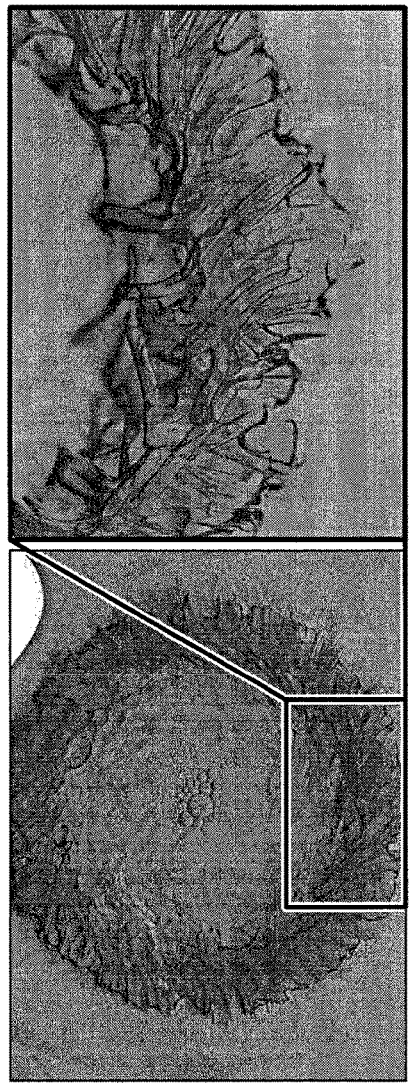

The cross-sectional structure of human small intestine consists of four layers: from 1 to 4, the layers represent the thick smooth muscle layer, the transition layer of muscle layer and epithelium, the intestinal villi and the intestinal lumen. (FIG. 6h) To resemble this layered structure, the soft tube was moulded with a thick circumferential layer of GelMa, as shown in FIG. 6i: prior to photocrosslinking, the tube was incubated in oil at 8° C.; GelMa solution stained red and warmed at approximately 30° C. was added to the gap between the tube and the beaker wall. The fast gelling red GelMa penetrated a thin layer into the blue network but gelled with the remaining network intact. Regions of both sides of the hybrid tube are expanded in FIGS. 6j and 6k, where a thin layer of blue rods rooted in red gel is shown. The four regions in FIGS. 6j and 6k are identical to the four layers of the diagram in FIG. 6h. The hybrid network had the mechanical strength to maintain its shape and stood in the absence of buoyant force. (FIG. 6l)

It is envisaged that the process of the invention may be used for the engineering of tissues characterized by elongated repeating units such as the gastrointestinal tract, muscle, ligament and tendon. For example, each villus in the human small intestine can be represented by a cell-bearing gel microrod unit (D=50–200 μm; L=0.5–2 mm); therefore, the lumen of the human small intestine might be engineered by assembling gel microrods into a tubular array (D~2 cm) (FIGS. 5 and 6).

Extending DMT Printing

ECM (extracellular matrix) materials such as collagen can be homogeneously blended into GelMa microrods to improve the 3D cell growth environment. The homogeneity of the mixed-composition microrods is illustrated in FIG. 13 by the homogeneous distribution of green fluorescence in rods. Due to the fast mixing in the microfluidic tubing, blending collagen into GelMa was not affected by the distinct gelling properties of the two phases. [A deMello, Nature, 2006, 442, 394-402.] The ability to mix ECM components into GelMa can potentially overcome the challenges related to the lacking of certain ECM inducing irregular gene expression in tissue reconstruction. [E Gustafsson, et al, Ann N Y Acad Sci, 2003, 995, 140-150]

DMT fabrication of gel microrods can be extended to much softer materials such as Matrigel, which is the optimal cell growth matrix in vitro. FIG. 14 illustrates the fabrication of homogeneous and Janus Matrigel rods by replacing the GelMa phase in previous sections with Matrigel and increasing the incubation temperature to 37° C.

Hydrodynamic Analysis

Mechanical stresses are critical in cell manipulation, and therefore a hydrodynamic simulation was performed in Comsol Multiphysics to explore the microenvironment in GelMa objects of various viscosities moving at a set average velocity ($v_a=3\times10^{-3}$ m/s) in the tubing. The oil viscosity $\mu_o=2\times10^{-3}$ Pa·s, and plug viscosity $\mu_g$ varied from 0.01 to 100 Pa·s, corresponding to the inner-to-outer viscosity ratio across the plug interface $\lambda=5$ to $5\times10^4$, and covering the range of GelMa prior to gelation at the concentrations which were explored. The flow in the tubing is axisymmetric and the 2D Axisymmetric Component in Comsol was implemented to reduce the computational cost and time, as illustrated in FIG. 16a. FIG. 16b compares velocity fields in the tubing: (b1) single phase flow (SPF) of GelMa, (b2) object flow at $\mu_g=0.01$ Pa·s (FIG. 15) and (b3) plug flow at $\mu_g=100$ Pa·s.

SPF flow topology did not vary from $\mu_g$=0.001 to 100 Pa·s. All velocity magnitudes, u, were normalised by $v_a$, i.e. $u/v_a$. At low viscosity ($\mu_g$=0.01 Pa·s), the GelMa object exhibited the typical internal circulation pattern found in microdroplets, whereas at high viscosity ($\mu_g$=100 Pa·s), this inner circulation was substantially reduced.

FIG. 16e shows the frequency distribution of the normalised velocity magnitudes in SPF and GelMa plugs of varying viscosities. It was found that the magnitude of internal circulation decreases with $\mu_g$, and after $\mu_g$ reaching 0.1 Pa·s, corresponding to $\lambda$=50, the internal circulation becomes significantly reduced; the droplet inner flow becomes uniform and approaches $u/v_a$=1.0. This finding is in accordance with the literature. [P. Urbant, Microfluid Nanofluid (2008) 4:533-542; B-J. Jin, J. Micromech. Microeng. 20 (2010) 035003]

Based on the velocity fields in FIGS. 16b and 16e, in-plane shear and extensional strain rates were calculated from $\varepsilon = \eta \bar{u}/\partial z + \partial \bar{v}/\partial x$ and $\eta = \partial \bar{u}/\partial x + \partial \bar{v}/\partial z$, respectively. $\bar{u}$ and $\bar{v}$ are the longitudinal and transverse velocity components, respectively. Both components were normalised by $v_a/r$, i.e. $\varepsilon \cdot r/v_a$ and $\eta \cdot r/v_a$, where r is the inner radius of the tubing (r=100 μm), and plotted in FIGS. 16c and 16f (normalised frequency distribution of $\varepsilon \cdot r/v_a$), and FIGS. 16d and 16g (normalised frequency distribution of $\eta \cdot r/v_a$), accordingly. Both shear components have higher magnitudes in low viscosity plugs but decrease with increasing object viscosity, and approaches zero at $\mu_g$=100 Pa·s; SPF flow has high level of extensional strains. Shear stresses are proportional to fluid viscosity; lower viscosity objects have a less detrimental effect on encapsulated cells, and the absence of significant shear stresses in high viscosity objects demonstrates the suitability of GelMa objects in encapsulating cells.

FIGS. 15 and 16 show that strain rates are lower in individual gel objects than in continuous single-phase flow, and the reduction in strain rates is more significant the higher the viscosity of the object. After the gel-to-oil viscosity ratio exceeds 50, interior circulation in the gel object is mostly suppressed and the strain rates approach zero. It can therefore be concluded that cells inside GelMa objects are protected from intense shear stresses and that the printing process of the present invention is compatible with cell manipulation.

Incorporation of Biological Cells

FIG. 17 illustrates the incorporation of biological cells into gel objects. NIH3T3 cells were cultured within the body of GelMe objects, and on their surfaces. The cells used expressed green fluorescent protein GFP (NIH-3T3/GFP). The images in FIG. 17 show the green fluorescent protein, illustrating that the cells survived both in and on the gel objects. Images (a-d) show GelMa rods having cells therein. Cells were initially loaded into 6.0 wt % GelMa at $5\times10^6$/ml, and imaged at (a, b) day 4 and (c, d) day 15 in culture. Images (e-f) show GelMa rods having cells thereon. Cells were seeded onto photocrosslinked 6.0 wt % GelMa network at $1\times10^7$/ml in culture medium, supplemented with 10% v/v Matrigel, and cultured for 2 days.

Different types of cells were successfully cultured in oriented GelMa microrods. These included human embryonic kidney cells (HEK293T), shown in FIGS. 19a and 19b; green fluorescent protein (GFP)-transfected NIH 3T3 cells (NIH3T3/GFP), shown in FIGS. 19c and 19d; and human colon myofibroblasts (CCD18Co), shown in FIGS. 19f and 19g. Also included were primary cells including human skeletal myoblasts (HSkM), FIG. 19e.

The cells were loaded in GelMa prior to droplet formation in DMT at $0.7-1.0\times10^7$ cells mL$^{-1}$. The microrods were photopolymerized after transfer to medium. The HEK293T cells proliferated as expanded clusters, which deformed the boundaries of the rods at day 9 in culture (FIG. 19b, deformation indicated by arrow). It is speculated that the deformation was caused by the local degradation of GelMa by cell secreted matrix metalloproteinases (MMP).

Bright field images showed that microrods containing NIH3T3/GFP fibroblasts retained their structure over the course of 15 days, thereby maintaining the structural integrity of the printed tissue network. GFP fluorescence suggests that the fibroblasts migrated and elongated by locally degrading the matrix (FIGS. 19c and 19d).

NIH3T3/GFP and primary HSkM cells showed elongation along the long axes of microrods. The anisotropy was apparent by eye. Anisotropy values for the numbered images were: (1) 0.19 and (2) 0.11 (FIGS. 19d and 19e respectively). CCD18Co cells were cultured in a softer isolated microrod (4.0% (w/v) GelMa). These cells were labelled with DAPI (this is apparent in the colour versions of FIGS. 19f and 19g where the nuclei appear blue) and Alexa Fluor® 647 phalloidin (F-actin, appearing in magenta in FIGS. 19f and 19g). These cells showed F-actin filaments oriented in parallel with the long axis of the microrod (anisotropy (3)=0.36, FIG. 19f). The orientation of F-actin in a stiffer isolated microrod (6.0% (w/v) GelMa) was reduced (anisotropy (4)=0.17, FIG. 19g). The anisotropy of F-actin in microrod arrays was lower than that in a isolated microrod of the same stiffness, not apparent by eye (anisotropy=(5) 0.07 and (6) 0.04, FIG. 19g), because the filaments crossed microrod boundaries.

All cell types retained high viability in the printed structures, from initially ~85% viable increasing to 90%-95% viable (FIG. 19h), with the increase attributed to cell division. Observation of typical cellular behaviours including migration and proliferation in culture after printing demonstrates that the shear stress in the tubing, the exposure to oil, the process of phase transfer and photocrosslinking are compatible with 3D cell culture. Furthermore the structural integrity of individual GelMa microrods and printed arrays were maintained over the course of two weeks (see the image after fifteen days in FIG. 19d). Local degradation of the GelMa matrix allowed cellular crosstalk and migration (FIG. 19).

Heterogeneous cell-bearing rods were produced by loading GelMa phases with different cell types: NIH3T3/GFP cells and HEK293T, the latter stained with CellTracker™ Red dye. By adjusting the flow rate ratio of second (red)-to-first (green) phases to 2:3, ternary co-culture rods were obtained, red at both ends and green in the middle (FIGS. 19i-19l). Such gel shapes might provide geometrically confined 3D environments for studying cell migration.

A more detailed bright-field image of a GelMa microrod array loaded with CCD18-Co cells is shown in FIG. 21. The rods shown correspond to those in FIG. 19g. CCD18-Co cells were initially loaded at $7\times10^6$ cells mL$^{-1}$ into GelMa (6.0% (w/v)) in PBS, and cultured for 9 days. The network was fixed with 4.0% (w/v) paraformaldehyde in PBS prior to imaging.

Also grown in GelMa microrods were human intestinal Caco-2 cells. The results are shown in FIG. 22. Caco-2 cells were initially seeded at $5\times10^6$ mL$^{-1}$ suspended in Minimum Essential Medium (MEM) medium onto lyophilised rods (6.0% (w/v) GelMa) and imaged after 3 weeks in culture.

(a): Bright-field image of a GelMa microrod array grown with Caco-2.
(b) Fluorescence image of Caco-2 cells immunostained with ZO-1 (tight junction protein-1) and conjugated to FITC after fixation. The dashed lines mark the interfaces between microrods.
(c) Fluorescence image of Caco-2 cells stained with 2 μM calcium-AM prior to fixation.
(d, e) A tube array after being lyophilised: (d) Bright-field imaging; (e) SEM imaging.

The lyophilised tube array maintained the structural integrity of individual rods as well as the entire network, but generated enough space among rods to allow cell penetration when being rehydrated by cell suspension.

(f) Fluorescence images of Caco-2 cells stained with DAPI (1:1000 dilution) on the rehydrated tube array, focused on two different heights.
(g) Bright-field and (h) z-projection fluorescence images of a GelMa microrod array after fixation, immunostained with Alexa Fluor® 647 Phalloidin.
(i) z-projection image of an isolated microrod from the rod array, stained with Alexa Fluor® 647 Phalloidin.

Rectangular images in (h, i) show the fluorescence profiles along the yellow lines in the associated images across the thickness of the rods.

The procedures for immunostaining cells before imaging to obtain the images in FIG. 22 are as follows. GelMa microrod arrays were fixed in 4.0% (w/v) paraformaldehyde in PBS for 20 min at room temperature, washed twice with PBS. The networks were then rinsed in 10.0% (w/v) glycerol in PBS for 10 min and then washed twice with PBS. Purified mouse anti-human ZO-1 (610966, BD Biosciences, UK) primary antibody was added at 1:300 dilution in PBS and incubated overnight at 4° C. After washing twice with PBS, goat anti-mouse IgM FITC (STAR86F, Bio-Rad, UK) secondary antibody was added at 1:500 dilution in PBS and incubated for 2 h at 37° C. For immunostaining of F-actin, Alexa Fluor® 647 Phalloidin (A22287, ThermoFisher Scientific, UK) was added at 1:500 dilution in PBS, and incubated for 3 h at 37° C. DAPI was added at 1:1000 in PBS and incubated for 20 min at room temperature before imaging. The tubular arrays were rinsed twice with PBS before imaging.

ZO-1, tight junction protein-1, is an intestinal epithelial marker. Alexa Fluor® 647 phalloidin is a high-affinity F-actin probe conjugated to far-red fluorescent Alexa Fluor® 647 dye. Immunostaining of ZO-1 and Alexa Fluor® 647 Phalloidin as well as DAPI staining were performed on different samples.

Matrigel Microrods Comprising Biological Cells

The use of natural extracellular matrix (ECM) components in place of GelMa, in whole or in part, is useful in creating a 3D tissue culture environment. The ECM composition influences the survival, development, migration, proliferation, morphology and function of cells embedded in it. The fabrication of DMT-printed gel microrods is shown here to be extended to softer materials such as Matrigel, which can form a favourable cell growth matrix.

Matrigel has been explored widely in cell biology and tissue engineering, because it resembles the matrix found in various tissues. However, due to its low stiffness (450 Pa), the fabrication of 3D Matrigel micro-shapes with tailored aspect ratios has been challenging. The ability of the process according to the present invention to produce Matrigel microrods is a significant advance.

Figure 20B:
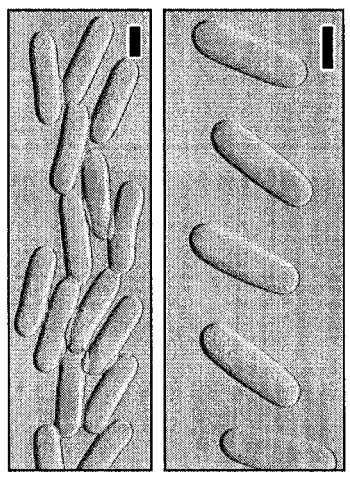
Figure 20A:
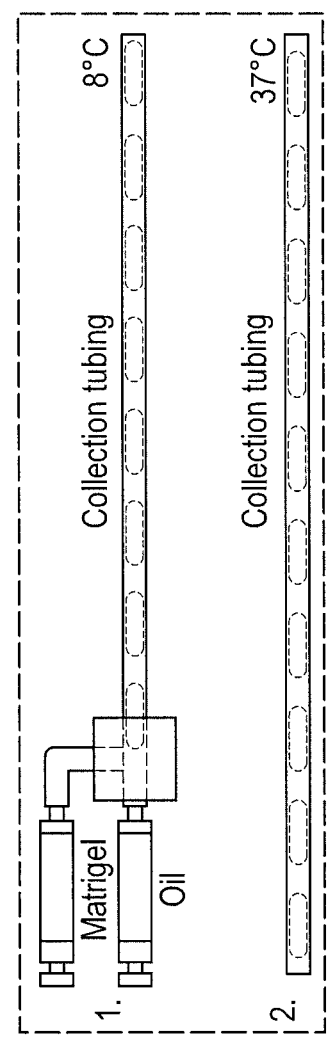
Figure 20D:
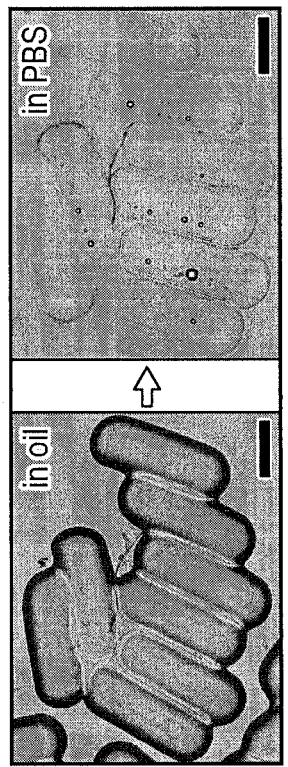
Figure 20C:
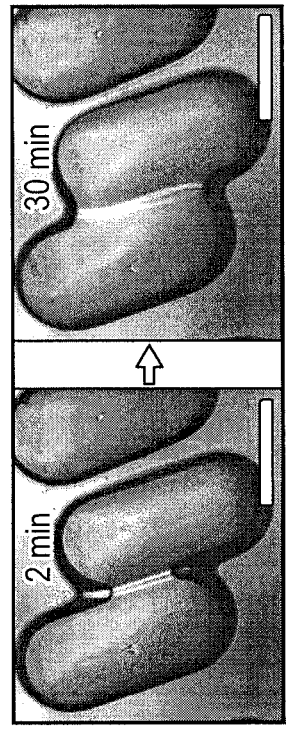
Figure 20E:
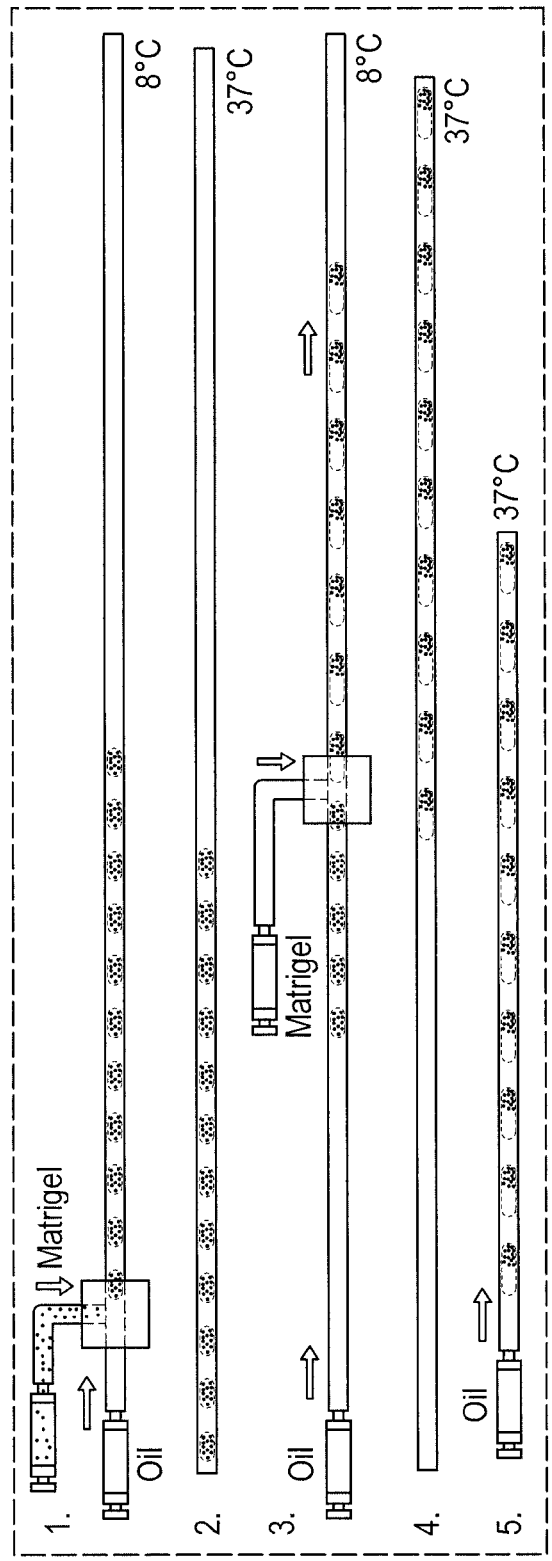
Figure 20G:
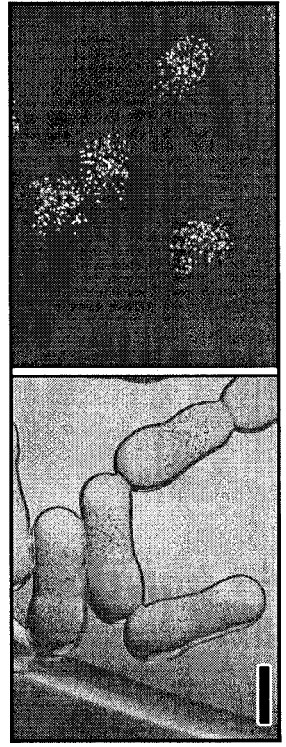
Figure 20F:
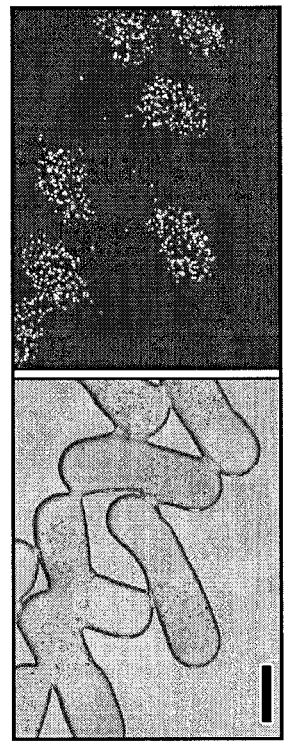

Homogeneous and heterogeneous (Janus and ternary) Matrigel microrods were fabricated by replacing the GelMa solution with Matrigel, and changing the incubation temperatures prior to and after Matrigel plug formation to 8° C. and 37° C., respectively (FIGS. 20a-20g). The structure of Matrigel microrods were maintained after extrusion into oil (FIG. 20c) and further transfer to PBS (FIG. 20d). Janus and ternary Matrigel microrods were formed by first forming one section (Matrigel loaded with fluorescent microspheres), and gelling, followed by injecting the second section (pure Matrigel) (FIG. 20e). The volume flow rate ratio of the microsphere-loaded Matrigel and the pure Matrigel were 1:1 (Janus microrods, FIG. 20f) and 2:3 (ternary microrods, FIG. 20g), respectively. NIH3T3/GFP cells were suspended in Matrigel prior to plug formation at 8° C. After incubation at 37° C. for 1 hour, the cell-laden Matrigel rods were extruded out of the tubing into oil and then suspended in the culture medium. Cellular migration to the rod periphery was observed after 3 days in culture, to form an annular distribution with web-like connections (FIG. 20h). Again, cells crossed the boundaries between neighbouring rods (FIG. 20i, yellow arrows). Cell-bearing Matrigel microrod array were patterned in oil, fused the rod-rod interface and transferred to medium (FIGS. 20j-20k). Continuous cellular network was obtained after 3 days in culture (FIG. 20l).

Cell Orientation in Microrods 3D tissue growth is regulated by the matrix geometry and stiffness. The process of the invention advantageously provides a gel network with controlled geometry and stiffness. For instance, the process of the invention is able to pattern microstructures, following natural geometries, and to tune stiffness to an optimal level. This is illustrated in FIGS. 19 and 20.

Individual human myofibroblasts compartmentalized in individual GelMa rods exhibited coordinated elongation, but cell-cell alignment is suppressed in microrod arrays or in more rigid microrods (FIGS. 19f and 19g). The transmicrorod cellular colonization is attributed to the intercellular communication established across the adjacent microrods. Stromal cells in individual soft Matrigel rods formed annular distributions by migrating to rod peripheries (FIG. 20h).

Phase Transfer of Networks

The transfer of two networks from oil to an aqueous phase was done by pipetting. The process is illustrated in FIG. 23. The phase transfer steps are as follows.
1. tetradecane was first pipetted out of the petri dish.
2. 1.5 mL of the volatile fluorinated oil HFE7200 (3M™ Novec™, USA, b.p. 76° C.; viscosity μ=0.61 cps at 25° C.) was added to the Petri dish to dissolve the tetradecane residues in the network.
3. The HFE7200 was pipetted out and the procedure was repeated 3 times.
4. Evaporate HFE7200 residues in air for 5 minutes.
5. Add buffer (PBS) to the networks.
6. Photopolymerize the networks.

Network integrity was maintained after phase-transfer. The bubbles seen in images (b) and (d) were generated by shear forces caused by pipetting. $Q_o=300$ μL h$^{-1}$; $Q_g=1000$ μL h$^{-1}$.

The invention claimed is:

1. A process for producing a gel network, which gel network comprises a plurality of joined gel objects, which process comprises:
   forming a plurality of incompletely-gelled gel objects in one or more microfluidic channels by;
   (a) providing a gel precursor material capable of undergoing a temperature-controlled sol-gel transition at a sol-gel transition temperature, (b) maintaining the gel precursor material at a first temperature above the sol-gel transition temperature, (c) introducing the gel precursor material into the one or more one or more microfluidic channels, and (d) maintaining at least a part of the one or more microfluidic channels at a second temperature, which second temperature is below the sol-gel transition temperature;

dispensing the incompletely-gelled gel objects from the one or more microfluidic channels into a region for producing the network; and contacting each incompletely-gelled gel object with at least one other incompletely-gelled gel object in said region to join each gel object to at least one other gel object at a region of contact between the gel objects, wherein contacting each incompletely-gelled gel object with at least one other incompletely-gelled gel object causes each incompletely-gelled gel object to fuse with at least one other incompletely-gelled gel object at a region of contact between the gel objects wherein gelling occurs at the region of fusion to form a gel bond between the gel objects.

2. A process according to claim 1, which process comprises:

forming a first incompletely-gelled gel object and a second incompletely-gelled gel object in a microfluidic channel;

dispensing the first and second incompletely-gelled gel objects from the microfluidic channel into a region for producing the network; and contacting the first incompletely-gelled gel object with the second incompletely-gelled gel object in said region and thereby joining the first incompletely-gelled gel object to the second incompletely-gelled gel object at a region of contact between the first and second incompletely-gelled gel objects;

wherein contacting the first incompletely-gelled gel object with at the second incompletely-gelled gel object causes said incompletely-gelled gel objects to fuse with each other at a region of contact between the gel objects wherein gelling occurs at the region of fusion to form a gel bond between the gel objects;

and which optionally further comprises;

forming one or more further incompletely-gelled gel objects in the microfluidic channel;

dispensing the one or more further gel objects from the microfluidic channel into the region for producing the network; and contacting each of the one or more further incompletely-gelled gel objects with the first incompletely-gelled gel object, the second incompletely-gelled gel object, or a further incompletely-gelled gel object in said region, and thereby joining each further gel object to at least one other gel object at a region of contact between the gel objects;

wherein contacting each of the one or more further incompletely-gelled gel objects with the first incompletely-gelled gel object, the second incompletely-gelled gel object, or a further incompletely-gelled gel object causes each incompletely-gelled gel object to fuse with at least one other incompletely-gelled gel object at a region of contact between the gel objects wherein gelling occurs at the region of fusion to form a gel bond between the gel objects.

3. A process according to claim 1 wherein the gel network comprises at least 50 joined gel objects.

4. A process according to claim 1 wherein the region for producing the gel network comprises a liquid medium which is immiscible with the gel objects and/or with a flowable gel precursor material from which the gel objects are formed.

5. A process according to claim 1 which further comprises moving a microfluidic channel relative to the region for producing the network in between dispensing incompletely-gelled gel objects from said microfluidic channel;

and/or which comprises controlling the orientation of each incompletely-gelled gel object that is dispensed relative to other gel objects in said region for producing the network.

6. A process according to claim 1 wherein each incompletely-gelled gel object is dispensed adjacent to at least one other incompletely-gelled gel object in said region for producing the network.

7. A process according to claim 1 which comprises forming the incompletely-gelled gel objects in the one or more microfluidic channels from a flowable gel precursor material, which flowable gel precursor material comprises a gel-forming agent and a fluid, optionally wherein
(i) the flowable gel precursor material comprises biological cells; and/or
(ii) the region for producing the network comprises a hydrophobic liquid and the gel precursor material is a hydrogel precursor material which comprises said gel-forming agent and water.

8. A process according to claim 1 wherein:

forming each incompletely-gelled gel object in a microfluidic channel comprises forming said incompletely-gelled gel object and an adjacent plug in the microfluidic channel; and dispensing a incompletely-gelled gel object from a microfluidic channel comprises dispensing said incompletely-gelled gel object and dispensing an adjacent plug from said microfluidic channel;

optionally wherein the plug is a liquid which is immiscible with the gel object and immiscible with a gel precursor material from which the gel object is formed.

9. A process according to claim 1 wherein the gel objects are hydrogel objects.

10. A process according to claim 1 which further comprises incubating the network of joined gel objects for an incubation period, wherein during the incubation period the network of joined gel objects is stored at a temperature below the sol-gel transition temperature.

11. A process according to claim 1 which further comprises a cross-linking step.

12. A process according to claim 1 wherein the gel objects are rod-shaped; optionally wherein the rod-shaped gel objects are from 10 μm to 2000 μm in diameter and from 10 μm to 10 mm in length.

13. A process according to claim 1 wherein each gel object has a volume of from $1.0 \times 10^{-7}$ μl to 10 μl or from $1.0 \times 10^{-3}$ μl to 1 μl; and/or wherein the gel network has a volume of from 1 mm$^3$ to 500 cm$^3$, from 0.5 cm$^3$ to 200 cm$^3$, from 5 cm$^3$ to 100 cm$^3$, or from 10 cm$^3$ to 80 cm3.

14. A process according to claim 1 wherein the gel objects comprise gel objects which have regions of differing composition, wherein each gel object which has regions of differing composition comprises: a first region and a second region, the first region having a composition which is different from that of the second region;

optionally wherein the first region comprises a material which is absent from the second region, or wherein the first and second regions comprise a material at different concentrations, optionally wherein the material is a therapeutic agent, a diagnostic agent, a protein, an enzyme, a nucleic acid, a biological cell or a gel-forming agent.

15. A process for producing a gel network, which gel network comprises a plurality of joined gel objects, which process comprises:

forming a plurality of incompletely-gelled gel objects in one or more microfluidic channels by
(a) providing a gel precursor material capable of undergoing a temperature-controlled sol-gel transition at a sol-gel transition temperature,
(b) maintaining the gel precursor material at a first temperature below the sol-gel transition temperature,
(c) introducing the gel precursor material into the one or more one or more microfluidic channels, and
(c) maintaining at least a part of the one or more microfluidic channels at a second temperature, which second temperature is above the sol-gel transition temperature;

dispensing the incompletely-gelled gel objects from the one or more microfluidic channels into a region for producing the network; and contacting each incompletely-gelled gel object with at least one other incompletely-gelled gel object in said region to join each gel object to at least one other gel object at a region of contact between the gel objects, wherein contacting each incompletely-gelled gel object with at least one other incompletely-gelled gel object causes each incompletely-gelled gel object to fuse with at least one other incompletely-gelled gel object at a region of contact between the gel objects wherein gelling occurs at the region of fusion to form a gel bond between the gel objects.

16. The process according to claim 15 which further comprises incubating the network of joined gel objects for an incubation period, wherein during the incubation period the network of joined gel objects is stored at a temperature above the sol-gel transition temperature.

* * * * *

UNITED STATES PATENT AND TRADEMARK OFFICE
CERTIFICATE OF CORRECTION

PATENT NO. : 11,624,047 B2
APPLICATION NO. : 16/305655
DATED : April 11, 2023
INVENTOR(S) : John Hagan Pryce Bayley and Shaohua Ma It is certified that error appears in the above-identified patent and that said Letters Patent is hereby corrected as shown below:

In the Claims

In Claim 13, Column 54, Line 58, delete "80 cm3." and insert -- 80 $cm^3$. --.

Signed and Sealed this
Fourth Day of July, 2023

Katherine Kelly Vidal
*Director of the United States Patent and Trademark Office*